(12) United States Patent
Kitajewski et al.

(10) Patent No.: US 7,662,919 B2
(45) Date of Patent: Feb. 16, 2010

(54) NOTCH-BASED FUSION PROTEINS AND USES THEREOF

(75) Inventors: Jan Kitajewski, Ridgewood, NJ (US); Carrie Shawber, Washington Township, NJ (US); Yasuhiro Funahashi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/114,962

(22) Filed: Apr. 26, 2005

(65) Prior Publication Data

US 2006/0030694 A1 Feb. 9, 2006

Related U.S. Application Data

(60) Provisional application No. 60/566,877, filed on Apr. 29, 2004.

(51) Int. Cl.
*C07K 14/00* (2006.01)
*C07K 17/00* (2006.01)
*A61K 38/00* (2006.01)
*A61K 39/00* (2006.01)

(52) U.S. Cl. .................. 530/350; 530/391.1; 514/12; 424/178.1

(58) Field of Classification Search ................ None
See application file for complete search history.

(56) References Cited

U.S. PATENT DOCUMENTS 5,428,130 A * 6/1995 Capon et al. ............... 530/350
6,379,925 B1 * 4/2002 Kitajewski et al. ......... 435/69.1

6,689,744 B2    2/2004  Gao et al.
6,703,221 B1 *  3/2004  Chan et al. ................. 435/69.1
6,716,974 B1    4/2004  Maciag et al.
2003/0194804 A1 10/2003 Lamb et al.

FOREIGN PATENT DOCUMENTS

WO    WO 2005/111072 A2    11/2005

OTHER PUBLICATIONS

Shimizu et al., (JBC Nov. 12, 1999 274(46):32961-32969.*
Varnum-Finney et al., Blood. Mar. 1, 2003;101(5):1784-9. Epub Oct. 31, 2002.*
Kojika et al., Exp Hematol 2001 29:1041-1052.*
De La Costa, Immunol Lett. Jan. 15, 2006;102(1):1-9. Epub Jul. 18, 2005.*

(Continued)

*Primary Examiner*—Cherie M Woodward
(74) *Attorney, Agent, or Firm*—John P. White; Cooper & Dunham LLP

(57) ABSTRACT

This invention provides a method for treating a subject having a tumor and a method for inhibiting angiogenesis in a subject, both comprising administering to the subject an effective amount of a composition of matter comprising the extracellular domain of a Notch receptor protein operably affixed to a half-life-increasing moiety. This invention also provides a composition of matter comprising the extracellular domain of Notch4 receptor protein operably affixed to a half-life-increasing moiety. This invention further provides an article of manufacture. Finally, this invention provides a replicable vector which encodes a polypeptide comprising the extracellular domain of a Notch receptor protein operably affixed to a half-life-increasing moiety, a host vector system which comprises such replicable vector and a method of producing such polypeptide.

6 Claims, 42 Drawing Sheets

OTHER PUBLICATIONS

Shimizu et al., JBC Nov. 12, 1999 274(46):32961-32969.*
UniProt Protein NOTC4_Human, pp. 1-14. Mar. 27, 2002.*
Artavanis-Tsakonas, S. et al. (1995) "Notch signaling," *Science* 268:225-232.
Artavanis-Tsakonas, S. et al. (1999) "Notch Signaling:Cell Fate Control and Signal Integration in Development," *Science* 284(5415):770-776.
Autiero, M. et al. (2003) "Role of P1GF in the intra- and intermolecular cross talk between the VEGF receptors Flt1 and Flk1," *Nat. Med.* 9(7):936-943.
Bailey, A.M. et al. (1995) "Suppressor of Hairless directly activates transcription of *Enhancer of split* Complex genes in response to Notch receptor activity," *Genes Dev.* 9:2609-2622.
Bettenhausen, B. et al. (1995) "Transient and restricted expression during mouse embryogenesis of *D111*, a murine gene closely related to *Drosophila Delta*," *Development* 121:2407-2418.
Bergers, G. et al. (2000) "Matrix metalloproteinase-9 triggers the angiogenic switch during carcinogenesis," *Nat. Cell. Biol.* 2(10):737-744.
Blaumueller, C.M. et al. (1997) "Intracellular cleavage of Notch leads to a heterodimeric receptor on the plasma membrane," *Cell* 90:281-291.
Caronti, B. et al. (1998) "Cerebral autosomal dominant arteriopathy with subcortical infarcts and leucoencephalopathy (CADASIL). Neuropathological and in vitro studies of abnormal elastogenesis," *Acta. Neurol. Scand.* 98:259-267.
Das, I. et al. (2004) "Notch oncoproteins depend on gamma-secretase/presenilin activity for processing and function," *J. Biol. Chem.* 279(29):30771-30780.
Desmond, D.W. et al. (1998) "CADASIL in a North American family: clinical, pathologic, and radiologic findings," *Neurology* 51:844-849.
Dunwoodie, S.L. et al. (1997) "Mouse *D113*: a novel divergent *Delta* gene which may complement the function of other *Delta* homologues during early pattern formation in the mouse embryo," *Development* 124:3065-3076.
Eastman, D.S. et al. (1997) "Synergy between suppressor of Hairless and Notch in regulation of *Enhancer of split m-gamma and m-delta* expression," *Mol. Cell. Biol.* 17:5620-5628.
Fortini, M.E. et al. (1993) "*Notch*: neurogenesis is only part of the picture," *Cell* 75:1245-1247.
Funahashi, Y. et al. (1999) "Establishment of a quantitative mouse dorsal air sac model and its application to evaluate a new angiogenesis inhibitor," *Oncol. Res.* 11(7):319-329.
Gale, N.W. et al. (2004) "Haploinsufficiency of delta-like 4 ligand results in embryonic lethality due to major defects in arterial and vascular development," *PNAS* 101(45):15949-15954.
Gale, N.W. et al. (1999) "Growth factors acting via endothelial cell-specific receptor tyrosine kinases: VEGFs, Angiopoietins, and ephrins in vascular development," *Genes Dev.* 13:1055-1066.
Gallahan, D. et al. (1997) "The mouse mammary tumor associated gene *INT3* is a unique member of the *NOTCH* gene family (*NOTCH4*)," *Oncogene* 14:1883-1890.
Gerhardt, H. et al. (2003) "VEGF guides angiogenic sprouting utilizing endothelial tip cell filopodia," *J. Cell Biol.* 161(6):1163-1177.
Greenwald, I. (1998) "LIN-12/Notch signaling: lessons from worms and flies," *Genes Dev.* 12:1751-1762.
Henderson, A.M. et al. (2001) "The basic helix-loop-helix transcription factor HESR1 regulates endothelial cell tube formation," *J. Biol. Chem.* 276:6169-6176.
Hicks, C. et al. (2000) "Fringe differentially modulates Jagged1 and Delta1 signalling through Notch1 and Notch2," *Nat. Cell Biol.* 2:515-520.
Hiratsuka, S. et al. (2002) "MMP9 induction by vascular endothelial growth factor receptor-1 is involved in lung-specific metastasis," *Cancer Cell* 2(4):289-300.
Hsieh, J.J. et al. (1996) "Truncated mammalian Notch1 activates CBF1/RBPJk-repressed genes by a mechanism resembling that of Epstein-Barr virus EBNA2," *Mole. Cell. Biol.* 16:952-959.
Hsieh, J.J. et al. (1997) "Epstein-Barr virus immortalization: Notch2 interacts with CBF1 and blocks differentiation," *J. Virol.* 71:1938-1945.
Itokawa, T. et al. (2002) "Antiangiogenic effect by SU5416 is partly attributable to inhibition of Flt-1 receptor signaling," *Mol. Cancer Ther.* 1(5):295-302.
Jarriault, S. et al. (1995) "Signaling downstream of activated mammalian Notch," *Nature* 377:355-358.
Joutel, A. et al. (2000) "The ectodomain of the *Notch3* receptor accumulates within the cerebrovasculature of CADASIL patients," *J. Clin. Invest.* 105:597-605.
Joutel, A. et al. (1996) "Notch3 mutations in CADASIL, a hereditary adult-onset condition causing stroke and dementia," *Nature* 383:707-710.
Koolwijk, P. et al. (1996) "Cooperative effect of TNF-alpha, bFGF, and VEGF on the formation of tubular structures of human microvascular endothelial cells in a fibrin matrix. Role of urokinase activity," *J. Cell Biol.* 132(6):1177-1188.
Kopan, R. et al. (1996) "Signal transduction by activated mNotch: importance of proteolytic processing and its regulation by the extracellular domain," *Proc. Natl. Acad. Sci. USA* 93:1683-1688.
Krebs, L.T. et al. (2000) "Notch signaling is essential for vascular morphogenesis in mice," *Genes Dev.* 14:1343-1352.
Lardelli, M. et al. (1994) "The novel Notch homologue mouse Notch3 lacks specific epidermal growth factor-repeats and is expressed in proliferating neuroepithelium," *Mech. Dev.* 46:123-136.
Lawson, N. D. et al. (2001) "Notch signaling is required for arterial-venous differentiation during embryonic vascular development," *Development* 128:3675-3683.
Leong, K.G. et al. (2002) "Activated Notch4 inhibits angiogenesis: role of beta1-integrin activation," *Mol. Cell. Biol.* 22(8):2830-2841.
Lewis, J. (1998) "Notch signalling and the control of cell fate choices in vertebrates," *Semin. Cell. Dev. Biol.* 9:583-589.
Lieber, T. et al. (1993) "Antineurogenic phenotypes induced by truncated Notch proteins indicate a role in signal transduction and may point to a novel function for Notch in nuclei," *Genes Dev.* 7:1949-1965.
Lindner, V. et al. (2001) "Members of the Jagged/Notch gene families are expressed in injured arteries and regulate cell phenotype via alterations in cell matrix and cell-cell interaction," *Am. J. Pathol.* 159:875-883.
Lindsell, C.E. et al. (1995) "Jagged: A mammalian ligand that activates Notch1," *Cell* 80:909-917.
Liu, Z.J. et al. (2003) "Regulation of Notch1 and Dll4 by vascular endothelial growth factor in arterial endothelial cells: implications for modulating arteriogenesis and angiogenesis," *Mol. Cell Biol.* 23(1):14-25.
Logeat, F. et al. (1998) "The Notch1 receptor is cleaved constitutively by a furin-like convertase," *Proc. Natl. Acad. Sci. USA* 95:8108-8112.
Lyman, D. et al. (1993) "Further evidence for function of the Drosophila Notch protein as a transmembrane receptor," *Proc. Natl. Acad. Sci. USA* 90:10395-10399.
Matsuno, K. et al. (1997) "Suppressor of Hairless-independent events in Notch signaling imply novel pathway elements," *Development* 124:4265-4273.
Montesano, R. et al. (1987) "Phorbol esters induce angiogenesis in vitro from large-vessel endothelial cells," *J. Cell. Physiol.* 130(2):284-291.
Nakagawa, O. et al. (2000) "Members of the HRT family of basic helix-loop-helix proteins act as transcriptional repressors downstream of Notch signaling," *PNAS* 97:13655-13660.
Noseda, M. et al. (2004) "Notch activation induces endothelial cell cycle arrest and participates in contact inhibition: role of p21Cip1 repression," *Mol. Cell Biol.* 24(20):8813-8822.
Oberg, C. et al. (2001) "The Notch intracellular domain is ubiquitinated and negatively regulated by the mammalian Sel-10 homolog," *J. Biol. Chem.* 276:35847-35853.
Owens, G.K. (1995) "Regulation of differentiation of vascular smooth muscle cells," *Physiol. Rev.* 75:487-517.
Pepper, M.S. (2001) "Role of the matrix metalloproteinase and plasminogen activator-plasmin systems in angiogenesis," *Arterioscler. Thromb. Vasc. Biol.* 21(7):1104-1117.

Rebay, I. et al. (1993) "Specific truncations of Drosophila Notch define dominant activated and dominant negative forms of the receptor," *Cell* 74:319-329.

Robey, E. (1997) "Notch in vertebrates," *Curr. Opin. Genet. Dev.* 7:551-557.

Roehl, H. et al. (1996) "Roles of the RAM and ANK domains in signaling by the C.elegans GLP-1 receptor," *EMBO J.* 15:7002-7012.

Rogers, S. et al. (1986) "Amino acid sequences common to rapidly degraded proteins: The PEST hypothesis," *Science* 234:364-368.

Sasai, Y. et al. (1992) "Two mammalian helix-loop-helix factors structurally related to Drosophila hairy and Enhancer of split," *Genes Dev.* 6:2620-2634.

Seiki, M. (2003) "Role of pericellular proteolysis by membrane-type 1 matrix metalloproteinase in cancer invasion and angiogenesis," *Cancer Metastasis Rev.* 22:129-143.

Shawber, C. et al. (1996) "Jagged2: a serrate-like gene expressed during rat embryogenesis," *Dev. Biol.* 180:370-376.

Shawber, C. et al. (1996) "Notch signaling inhibits muscle cell differentiation through a CBF1-independent pathway," *Development* 122:3765-3773.

Shawber, C.J. et al. (2004) "Notch function in the vasculature: insights from zebrafish, mouse and man," *BioEssays* 26(3):225-234.

Shimizu, K. et al. (2002) "Integrity of intracellular domain of Notch ligand is indispensable for cleavage required for release of the Notch2 intracellular domain," *Embo J.* 21:294-302.

Shutter, J.R. et al. (2000) "Dll4, a novel Notch ligand expressed in arterial endothelium," *Genes Dev.* 14:1313-1318.

Small, D. et al. (2001) "Soluble Jagged 1 represses the function of its transmembrane form to induce the formation of the Src-dependent chord-like phenotype," *J. Biol. Chem.* 276(34):32022-32030.

Struhl, G. et al. (1993) "Intrinsic activity of the Lin-12 and Notch intracellular domains in vivo," *Cell* 74:331-345.

Swiatek, P.J. et al. (1994) "*Notch1* is essential for postimplantation development in mice," *Genes Dev.* 8:707-719.

Tamura, K. et al. (1995) "Physical interaction between a novel domain of the receptor Notch and the transcription factor RBP-Jkappa/Su(H)," *Curr. Biol.* 5:1416-1423.

Taylor, K.L. et al. (2002) "Notch activation during endothelial cell network formation in vitro targets the basic HLH transcription factor HESR-1 and downregulates VEGFR-2/KDR expression," *Microvasc. Res.* 64(3):372-383.

Tietze, K. et al. (1992) "Enhancer of splitD, a dominant mutation of Drosophila, and its use in the study of functional domains of a helix-loop-helix protein," *Proc. Natl. Acad. Sci. USA* 89:6152-6156.

Uyttendaele, H. et al. (2001) "Vascular patterning defects associated with expression of activated Notch4 in embryonic endothelium," *PNAS* 98:5643-5648.

Uyttendaele, H. et al. (1996) "Notch4/int-3, a mammary proto-oncogene, is an endothelial cell-specific mammalian Notch gene," *Development* 122:2251-2259.

Vervoort, M. et al. (1997) "Cell fate determination in Drosophila," *Curr. Opin. Neurobiol.* 7:21-28.

Villa, N. et al. (2001) "Vascular expression of Notch pathway receptors and ligands is restricted to arterial vessels," *Mech. Dev.* 108:161-164.

Weinmaster, G. (1997) "The Ins and Outs of Notch Signaling," *Mol. Cell. Neurosci.* 9:91-102.

Weinmaster, G. (1998) "Notch signaling: direct or what?," *Curr. Opin. Genet. Dev.* 8:436-442.

Weinmaster, G. et al. (1992) "*Notch 2*: a second mammalian *Notch* gene," *Development* 116:931-941.

Weinmaster, G. et al. (1991) "A homolog of Drosophila Notch expressed during mammalian development," *Development* 113:199-205.

Wettstein, D.A. et al. (1997) "The Xenopus homolog of Drosophila Suppressor of Hairless mediates Notch signaling during primary neurogenesis," *Development* 124:693-702.

Wu, G. et al. (1998) "Evidence for functional and physical association between *Caenorhabditis elegans* SEL-10, a Cdc4p-related protein, and SEL-12 presenilin," *Proc. Natl. Acad. Sci. USA* 95:15787-15791.

Wu G. et al. (2001) "SEL-10 is an inhibitor of Notch signaling that targets Notch for Ubiquitin-mediated protein degradation," *Mol. Cell. Biol.* 21:7403-7415.

Xue, Y. et al. (1999) "Embryonic lethality and vascular defects in mice lacking the Notch ligand Jagged1," *Hum. Mol. Genet.* 8:723-730.

Yamamoto, M. et al. (1998) "Inhibition of membrane-type 1 matrix metalloproteinase by hydroxamate inhibitors: an examination of the subsite pocket," *J. Med. Chem.* 41(8):1209-1217.

Greenwald, I. (1994) "Structure/function studies of lin-12/Notch proteins," *Curr. Opin. Genet. Dev.* 4: 556-562.

Lawson N. D. et al. (2002) Sonic hedgehog and vascular endothelial growth factor act upstream of the Notch pathway during arterial endothelial differentiation *Dev. Cell* 3:127-136.

\* cited by examiner

Activation of Notch signaling in HUVEC infected with adenoviral encoding VEGF-165

Notch ectodomain (Notch Decoy) inhibit activation of Notch signaling induced by VEGF stimulation in adenovirus-infected HUVEC
(a) time
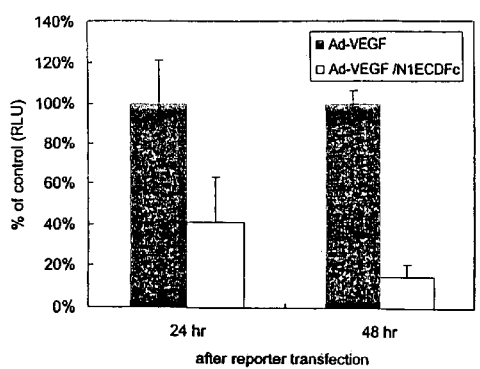
(b) MOI
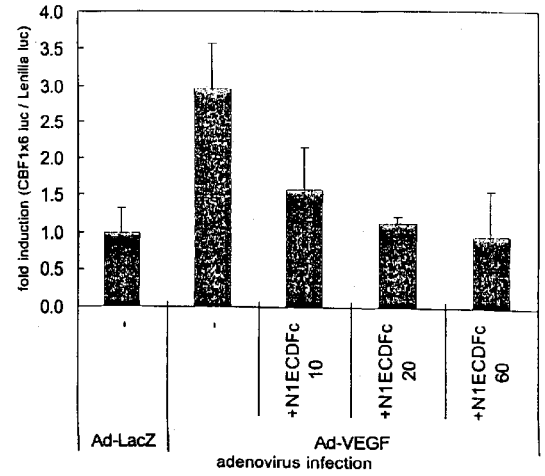
Figure 7

Figure 10

```
   1 mprllapllc ltllpalaar glrcsqpsgt clnggrceva ngteacvcsg afvgqrcqdp
  61 spclstpckn agtcyvvdhg givdyacscp lgfsgplclt planaclanp crnggtcdll
 121 tlteykcrcp pgwsgkscqq adpcasnpca nggqclpfes syicgcppgf hgptcrqdvn
 181 ecsqnpglcr hggtchneig syrcacrath tgphcelpyv pcspspcqng gtcrptgdtt
 241 hecaclpgfa gqnceenvdd cpgnnckngg acvdgvntyn crcppewtgq yctedvdecq
 301 lmpnacqnag tchnshggyn cvcvngwtge dcsdniddca saacfqgatc hdrvasfyce
 361 cphgrtgllc hlndacisnp cnegsncdtn pvngkaictc prgytgpacs qdvdecalga
 421 npcehagkcl ntlgsfecqc lqgytgprce idvnecisnp cqndatcldq igefqcicmp
 481 gyegvycein tdecasspcl hngrcvdkin eflcqcpkgf sghlcqydvd ecastpckng
 541 akcldgpnty tcvctegytg thcevdidec dpdpchiglc kdgvatftcl cqpgytghhc
 601 etninechsq pcrhggtcqd rdnyylclcl kgttgpncei nlddcasnpc dsgtcldkid
 661 gyecacepgy tgsmcnvnid ecagspchng gtcedgiagf tcrcpegyhd ptclsevnec
 721 nsnpcihgac rdglngykcd capgwsgtnc dinnnecesn pcvnggtckd mtsgyvctcr
 781 egfsgpncqt ninecasnpc lnqgtciddv agykcncplp ytgatcevvl apcatspckn
 841 sgvckesedy esfscvcptg wqgqtceidi necvkspcrh gascqntngs yrclcqagyt
 901 grncesdidd crpnpchngg sctdgvnaaf cdclpgfqga fceedineca tnpcqnganc
 961 tdcvdsytct cptgfngihc enntpdctes scfnggtcvd ginsftclcp pgftgsycqy
1021 dvnecdsrpc lhggtcqdsy gtykctcpqg ytglncqnlv rwcdsapckn ggkcwqtntq
1081 yhcecrsgwt gfncdvlsvs cevaaqkrgi dvtllcqhgg lcvdeedkhy chcqagytgs
1141 ycedevdecs pnpcqngatc tdylggfsck cvagyhgsnc seeineclsq pcqnggtcid
1201 ltntykcscp rgtqgvhcei nvddchppld pasrspkcfn ngtcvdqvgg ytctcppgfv
1261 gercegdvne clsnpcdprg tqncvqrvnd fhcecraght grrcesving crgkpcrngg
1321 vcavasntar gficrcparf egatcendar tcgslrclng gtcisgprsp tclclgsftg
1381 pecqfpassp cvgsnpcynq gtceptsesp fyrclcpakf ngllchildy sft 1433
```

LINKER SEQUENCE
DLGPG

Figure 11

```
   1 mpalrpaalr allwlwlcga gpahalqcrg gqepcvnegt cvtyhngtgy crcpegflge
  61 ycqhrdpcek nrcqnggtcv tqamlgkatc rcapgftged cqystshpcf vsrpcqnggt
 121 chmlswdtye ctcqvgftgk qcqwtdvcls hpcengstcs svanqfscrc pagitgqkcd
 181 adinecdipg rcqhggtcln lpgsyrcqcp qrftgqhcds pyvpcapspc vnggtcrqtg
 241 dftsechclp gfegsncern iddcpnhkcq nggvcvdgvn tyncrcppqw tgqfctedvd
 301 ecllqpnacq nggtctnrng gygcvcvngw sgddcsenid dcafasctpg stcidrvasf
 361 sclcpegkag llchlddaci snpchkgalc dtnplngqyi ctcpqaykga dctedvdeca
 421 mansnpceha gkcvntdgaf hceclkgyag prcemdinec hsdpcqndat cldkiggftc
 481 lcmpgfkgvh celevnecqs npcvnngqcv dkvnrfqclc ppgftgpvcq ididdcsstp
 541 clngakcidh pngyecqcat gftgtlcden idncdpdpch hgqcqdgids yticnpgym
 601 gaicsdqide cysspclndg rcidlvngyq cncqpgtsgl nceinfddca snpclhgacv
 661 dginryscvc spgftgqrcn ididecasnp crkdatcind vngfrcmcpe gphhpscysq
 721 vneclsspci hgnctgglsg ykclcdagwv gincevdkne clsnpcqngg tcnnlvngyr
 781 ctckkgfkgy ncqvnideca snpclnqgtc lddvsgytch cmlpytgknc qtvlapcspn
 841 pcenaavcke apnfesftcl capgwggqrc tvdvdecvsk pcmnngichn tqgsymcecp
 901 pgfsgmdcee dindclanpc qnggscvdkv ntfsclclpg fvgdkcqtdm neclsepckn
 961 ggtcsdyvns ytctcpagfh gvhcennide ctesscfngg tcvdginsfs clcpvgftgp
1021 fclhdinecs snpclnsgtc vdglgtyrct cplgytgknc qtlvnlcsps pcknkgtcaq
1081 ekarprclcp pgwdgaycdv lnvsckaaal qkgvpvehlc qhsgicinag nthhcqcplg
1141 ytgsyceeql decasnpcqh gatcsdfigg yrcecvpgyq gvnceyevde cqnqpcqngg
1201 tcidlvnhfk cscppgtrgl lceeniddca gaphclnggq cvdriggysc rclpgfager
1261 cegdinecls npcssegsld ciqlknnyqc vcrsaftgrh cetfldvcpq kpclnggtca
1321 vasnvpdgfi crcppgfsga rcqsscgqvk crrgeqcvht asgphcfcpn hkdcesgcas
1381 npcqhggtcy pqrqppyysc rcsppfwgsh cesytapts  1419
```

LINKER SEQUENCE
DLGPG

Figure 12

```
   1 mglgargrrr rrrlmalppp pppmralpll lllaglgaaa ppcldgspca nggrcthqqp
  61 sleaaclclp gwvgercqle dpchsgpcag rgvcqssvva gtarfscrcl rgfqgpdcsq
 121 pdpcvsrpcv hgapcsvgpd grfacacppg yqgqscqsdi decrsgttcr hggtclntpg
 181 sfrcqcplgy tgllcenpvv pcapspcrng gtcrqssdvt ydcaclpgfe gqncevnvdd
 241 cpghrclngg tcvdgvntyn cqcppewtgq fctedvdecq lqpnachngg tcfnllgghs
 301 cvcvngwtge scsqniddca tavcfhgatc hdrvasfyca cpmgktgllc hlddacvsnp
 361 chedaicdtn pvsgraictc ppgftggacd qdvdecsiga npcehlgrcv ntqgsflcqc
 421 grgytgprce tdvneclsgp crnqatcldr igqftcicma gftgtycevd idecqsspcv
 481 nggvckdrvn gfsctcpsgf sgsmcqldvd ecastpcrng akcvdqpdgy ecrcaegfeg
 541 tlcernvddc spdpchhgrc vdgiasfsca capgytgirc esqvdecrsq pcryggkcld
 601 lvdkylcrcp pgttgvncev niddcasnpc tfgvcrdgin rydcvcqpgf tgplcnvein
 661 ecasspcgeg gscvdgengf hclcppgslp plclpanhpc ahkpcshgvc hdapggfrcv
 721 cepgwsgprc sqslapdace sqpcqaggtc tsdgigfrct capgfqghqc evlspctpsl
 781 cehgghcesd pdrltvcscp pgwqgprcqq dvdecagasp cgphgtctnl pgnfrcichr
 841 gytgpfcdqd iddcdpnpcl hggscqdgvg sfscscldgf agprcardvd eclsspcgpg
 901 tctdhvasft cacppgyggf hceidlpdcs psscfnggtc vdgvssfscl crpgytgthc
 961 qyeadpcfsr pclhggicnp thpgfectcr egftgsqcqn pvdwcsqapc qnggrcvqtg
1021 aycicppgws grlcdiqslp cteaaaqmgv rleqlcqegg kcidkgrshy cvcpegrtgs
1081 hcehevdpct aqpcqhggtc rgymggyvce cpagyagdsc ednidecasq pcqnggscid
1141 lvarylcscp pgtlgvlcei neddcdlgps ldsgvqclhn gtcvdlvggf rcncppgytg
1201 lhceadinec rpgachaaht rdclqdpggh frcvchpgft gprcqialsp cesqpcqhgg
1261 qcrhslgrgg gltftchcvp pfwglrcerv arscrelqcp vgipcqqtar gprcacppgl
1321 sgpscrvsra spsgatnasc asapclhggs clpvqsvpff rcvcapgwgg prcetpsaa 1379
```

Linker Sequence
No linker sequence

Figure 13

```
   1 mqpqllllll lplnfpvilt rellcggspe pcanggtclr lsrgqgicqc apgflgetcq
  61 fpdpcrdtql cknggscqal lptppssrsp tspltphfsc tcpsgftgdr cqthleelcp
 121 psfcsngghc yvqasgrpqc scepgwtgeq cqlrdfcsan pcanggvcla typqiqcrcp
 181 pgfeghtcer dinecflepg pcpqgtschn tlgsyqclcp vgqegpqckl rkgacppgsc
 241 lnggtcqlvp eghstfhlcl cppgftgldc emnpddcvrh qcqngatcld gldtytclcp
 301 ktwkgwdcse dideceargp prcrnggtcq ntagsfhcvc vsgwggagce enlddcaaat
 361 capgstcidr vgsfsclcpp grtgllchle dmclsqpchv naqcstnplt gstlcicqpg
 421 ysgstchqdl decqmaqqgp spcehggsci ntpgsfnclc lpgytgsrce adhneclsqp
 481 chpgstcldl latfhclcpp glegrlceve vnectsnpcl nqaachdlln gfqclclpgf
 541 tgarcekdmd ecsstpcang grcrdqpgaf yceclpgfeg phcekevdec lsdpcpvgas
 601 cldlpgaffc lcrpgftgql cevplctpnm cqpgqqcqgq ehrapclcpd gspgcvpaed
 661 ncpchhghcq rslcvcdegw tgpecetelg gcistpcahg gtchpqpsgy nctcpagymg
 721 ltceevtac hsgpclnggs csirpegysc tclpshtgrh cqtavdhcvs asclnggtcv
 781 nkpgtffclc atgfqglhce ektnpscads pcrnkatcqd tprgarclcs pgytgsscqt
 841 lidlcarkpc phtarclqsg psfqclclqg wtgalcdfpl scqkaamsqg ieisglcqng
 901 glcidtgssy fcrcppgfqg klcqdnvnpc epnpchhgst cvpqpsgyvc qcapgyegqn
 961 cskvldacqs qpchnhgtct srpggfhcac ppgfvglrce gdvdecldrp chpsgtaach
1021 slanafycqc lpghtgqrce vemdlcqsqp csnggsceit tgpppgftch cpkgfegptc
1081 shkalscgih hchngglclp spkpgspplc aclsgfggpd cltppappgc gppspclhng
1141 tctetpglgn pgfqctcppd spgprcqrpg 1170
```

LINKER SEQUENCE
DLGPG

Figure 14A

```
   1 atgacaggct tccagggctg ccaggccctg ctgcatctgg ccaaggccgt ggttcgcttg
  61 agatgctccc agccaagtgg gacctgcctg aatggaggga ggtgcgaagt ggccaacggc
 121 actgaagcct gtgtctgcag cggagcgttc gtgggccagc gatgccagga ccccagccct
 181 tgcctcagca caccatgtaa gaatgctgga acgtgctatg ttgtggacca tggcggcatc
 241 gtggactatg cctgcagttg cccctgggt ttctctgggc ccctctgcct gacacctctg
 301 gccaatgcct gcctggccaa cccctgccgc aacggggga cctgtgacct gctcactctc
 361 acagaataca agtgccggtg cccgccaggg tggtcaggaa agtcatgtca gcaagccgac
 421 ccctgtgcct ccaacccctg tgccaatggt ggccagtgcc tgccctttga gtcttcatac
 481 atctgtggct gcccgccgg cttccatggc cccacctgca gacaagatgt taacgagtgc
 541 agccagaacc ctgggttgtg ccgtcatggc ggcacgtgcc acaatgagat tggctcctat
 601 cgctgtgcct gccgtgccac ccacactggt ccccactgcg agctgccta cgtgccctgc
 661 agcccctcac cctgccagaa cggaggcacc tgccgcccta cggggacac cacccacgag
 721 tgtgcctgcc tgccaggctt tgctggacag aactgtgaag aaaatgtgga tgactgccca
 781 ggaaacaact gcaagaacgg gggtgcctgt gtggacggtg tgaataccta caattgccgc
 841 tgcccaccgg agtggacagg tcagtactgc acagaggatg tggacgagtg tcagctcatg
 901 cccaacgcct gccagaatgg cggaacctgc cacaactccc acggtggcta caactgcgtg
 961 tgtgtcaatg gctggactgg tgaggactgc agtgagaaca ttgatgactg tgccagtgcc
1021 gcctgttttc agggtgccac ctgccatgac cgtgtggctt ccttctactg cgagtgtcca
1081 catgggcgca caggcctgct gtgccacctg aacgatgcgt gtatcagcaa ccctgcaac
1141 gagggctcca actgcgacac caaccctgtc aacggcaagg ccatctgcac ttgcccctcg
1201 gggtacacgg ggccagcctg cagccaggac gtggatgagt gcgctctagg tgccaacccg
1261 tgtgagcacg cgggcaagtg cctcaacaca ctgggctctt cgagtgtca gtgtctacag
1321 ggctacactg ggccccgctg tgagattgat gtcaacgagt gcatctccaa cccatgtcag
1381 aatgatgcca cgtgcctgga ccagattggg gagtttcagt gtatatgtat gccaggttat
1441 gagggtgtat actgtgagat caacacggac gagtgtgcca gcagcccctg tctacacaat
1501 ggccgctgcg tggacaagat caacgagttc ctgtgtcagt gtcccaaagg cttcagcggg
1561 cacctgtgcc agtatgacgt ggatgagtgc gccagcacac catgcaagaa cggcgccaag
1621 tgcctggatg ggcccaacac ctacacctgc gtgtgcacag aaggttacac ggggacccac
1681 tgcgaggtgg acattgacga gtgtgaccct gaccctgtc actatggttt gtgcaaggat
1741 ggtgtggcca cctttacctg cctctgccag ccaggctaca caggccatca ctgtgagacc
1801 aacattaatg agtgtcacag ccagccgtgc cgccatggcg gcacctgcca ggaccgtgac
1861 aactactacc tctgcttatg cctcaagggg accacaggac caactgtga gatcaatctg
1921 gatgactgtg cgagcaaccc ctgtgactct ggcacgtgtc tggacaagat cgatggctac
1981 gagtgtgcgt gcgagccagg ctacacaggg agcatgtgta atgtcaacat tgacgaatgt
2041 gcgggcagcc cctgccacaa cggggcacc tgtgaggatg gcatcgccgg cttcacttgc
2101 cgctgccccg agggctacca cgaccctacg tgcctgtctg aggtcaacga gtgcaacagt
2161 aacccctgca tccatggagc ttgccgggat ggcctcaatg gatacaaatg tgactgtgcc
2221 cctgggtgga gtgggacaaa ctgtgacatc aacaacaatg agtgtgagtc caaccccttgt
2281 gtcaacggtg gcacctgcaa agacatgacc agtggctacg tatgcacctg ccgagaaggc
2341 ttcagtggcc taactgcca gaccaacatt aacgaatgtg cttccaaccc ctgcctgaac
2401 cagggcacct gcattgatga tgtcgctggg tacaaatgca actgccctct gccctataca
2461 ggagccacat gtgaggtggt gttggcccca tgtgccacca gccctgcaa aaacagtggg
2521 gtatgcaagg agtctgagga ctatgagagc ttttcctgtg tctgtcccac aggctggcaa
2581 ggtcaaacct gcgagatcga catcaatgag tgtgtgaaaa gcccgtgtcg ccatggtgcc
2641 tcttgccaga acaccaatgg cagctaccgc tgcctctgcc aggctggcta cacgggtcgc
2701 aactgcgaga gtgacatcga tgactgccga cccaacccat gtcacaacgg gggttcctgc
2761 actgacgggg tcaacgcggc cttctgcgac tgcctgcccg gcttccaggg tgccttctgt
2821 gaggaggaca tcaacgaatg cgccagcaat ccatgccaaa atggcgccaa ctgcactgac
2881 tgcgtggaca gctacgtca ccctgcccc acgggcttca tggcatcca ttgcgagaac
2941 aacacacctg actgtaccga gagctcctgt ttcaatggtg cacctgtgt ggatggtatc
3001 aactccttca cctgtctgtg cccacctggc ttcacgggca gctactgca gtatgacgtc
3061 aatgagtgtg actcacggcc tgtctgcat ggtggcacct gcaagacag ctatggtacc
3121 tataagtgta cctgcccaca gggctacact ggtctcaact gccagaacct tgtgcgctgg
3181 tgtgactcag ctccctgcaa gaatggcggc aagtgctggc agaccaacac acagtaccac
3241 tgcgagtgcc gcagcggctg gactggcttc aactgcgacg tgctcagtgt gtcctgcgag
```

*Figure 14B*

```
3301 gtggctgcac agaagcgagg catcgatgtc actctcctat gccagcacgg agggctctgt
3361 gtggatgagg aagacaagca ttactgccac tgccaggcag gatacacggg cagctactgt
3421 gaggacgagg tggacgagtg ctcacctaat ccctgccaga acggagccac ctgcactgac
3481 tatctcggtg gctttcctg caagtgtgtg gctgggtacc atggctctaa ctgctctgag
3541 gagatcaacg agtgcctatc ccaaccctgc cagaatgggg gtacctgcat tgatctgacc
3601 aacacctaca agtgctcctg ccccaggggc acacagggtg tacactgtga gatcaacgtc
3661 gatgactgcc atcctcccct agaccctgct tcccgaagcc ccaaatgctt caataatggc
3721 acctgcgtgg accaggtggg tggctatacc tgcacctgcc cgccaggctt cgtcggggag
3781 cggtgcgagg gcgatgtcaa tgagtgtctc tccaacccct gtgacccacg tggcacccag
3841 aactgcgtgc agcgtgttaa tgacttccac tgcgagtgcc gggctggcca cactggacgc
3901 cgctgtgagt cggtcattaa tggctgcagg ggcaaaccat gcaggaatgg aggtgtctgt
3961 gctgtggcct ccaacaccgc ccgtggattc atctgtaggt gccctgcggg cttcgagggt
4021 gccacttgtg aaaatgacgc ccgcacttgt ggcagtttgc gctgcctcaa cggtggtacg
4081 tgcatctcag gcccacgcag tcccacctgc ctatgcctgg gctccttcac tggccctgaa
4141 tgccagttcc cagccagcag ccctgtgtg ggtagcaacc cctgctacaa tcagggcacc
4201 tgtgagccca catccgagag ccctttctac cgctgtctat gccctgccaa attcaacggg
4261 ctgctgtgcc acatcctgga ctacagcttc aca 4293
```

*Figure 15A*

```
 511 atgcccgctc tgcgtcccgc cgcgctgcgg
 541 gcgctgctgt ggctctggct gtgcggcgcg ggccccgcgc acgctttgca gtgtcgaggt
 601 ggtcaagagc cctgtgtaaa tgaggggacc tgtgttacct accacaacgg cacaggctac
 661 tgccgatgtc cagagggctt cttgggagaa tattgtcaac atcgagaccc ttgtgagaag
 721 aaccgctgtc agaatggtgg tacttgtgtg acgcaggcca tgttgggaaa agccacctgt
 781 cgatgtgctc cagggttcac agggaggac tgccaatact cgacctctca cccctgtttt
 841 gtttcccgcc cctgtcagaa tggaggtacc tgccacatgc tcagctggga cacctatgag
 901 tgcacctgtc aagttggctt cacaggaaag cagtgtcagt ggacagatgt ctgtctgtct
 961 catccctgtg aaaatggaag cacctgtagc tctgtggcca accagttctc ctgcagatgt
1021 cctgcaggca tcacaggcca gaagtgtgac gccgacatca atgaatgtga cattccagga
1081 cgctgccaac atggtggcac ctgcctcaac cttcctgggt cctaccgatg ccaatgccct
1141 cagcggttca caggccagca ctgtgacagc ccttacgtgc cctgtgcacc ctcaccctgc
1201 gtcaatggag gcacctgccg tcagactgga gacttcactt ctgaatgcca ttgcctgcca
1261 ggctttgaag ggagcaactg cgagcggaat atcgacgact gccctaacca caagtgtcag
1321 aatggagggg tgtgtgtgga tggcgtcaat acttacaact gccgctgccc ccctcagtgg
1381 actgggcagt ctgcacaga agacgtggat gagtgtctgc tgcagcccaa tgcttgtcag
1441 aatggaggca cttgcaccaa ccgcaacgga ggctacggct gcgtgtgcgt gaacggctgg
1501 agtggggatg actgcagcga gaacatcgat gactgtgcct tcgcttcctg cacgccaggc
1561 tccacctgta ttgaccgtgt ggcctccttc tcctgccttt gtccagaggg aaaggcaggg
1621 ctcctgtgtc atctggatga tgcctgtatc agcaaccctt gtcacaaggg ggcgctgtgt
1681 gataccaacc ccctgaatgg gcagtacatt tgcacctgcc cacaggcgta caagggcgct
1741 gactgcacag aagacgtgga tgagtgtgct atggccaaca gtaaccttg tgagcatgca
1801 ggaaagtgtg tgaatacaga tggcgccttc cactgcgagt gtctgaaggg ctacgcaggg
1861 cctcgctgtg agatggacat caacgagtgt cactcagacc cctgtcagaa cgacgccacc
1921 tgcctggata agattggagg cttcacctgt ctctgcatgc cgggtttcaa aggtgtgcat
1981 tgtgaactgg aggtgaatga atgccagagc aacccgtgtg taaacaatgg gcagtgtgtg
2041 gacaaagtca atcgcttcca gtgtctgtgt ccccctggtt tcacaggacc agtgtgccag
2101 atcgacattg acgactgctc cagtactccc tgcctgaatg gggccaagtg catcgatcac
2161 ccgaatggct atgaatgcca gtgtgccaca ggattcactg gcacactgtg tgatgagaac
2221 atcgacaact gtgacccgga tccttgccac catggccagt gccaggatgg gattgactcc
2281 tacacctgca tctgcaaccc cgggtacatg ggagccatct gtagtgacca gattgatgaa
2341 tgctacagca gcccctgcct gaatgatgga cgctgcatcg acctggtgaa cggctaccag
2401 tgcaactgcc aaccgggtac ctcaggcctt aattgtgaaa ttaattttga tgactgtgcc
2461 agcaaccctt gtctgcacgg agcctgtgtg gacggcatca accgttacag ttgtgtgtgc
2521 tctccgggat tcacagggca gaggtgcaac atagacattg atgagtgtgc ctccaacccc
2581 tgtcgcaagg atgcgacgtg catcaatgac gtgaatggtt tccggtgtat gtgccctgag
2641 ggaccacacc atcccagctg ctactcacag gtgaacgagt gtttgagcag tccctgcatc
2701 catggaaact gtactggagg tctcagtggc tataagtgcc tctgcgatgc aggctgggtt
2761 ggtatcaact gcgaagtgga caaaaatgag tgtcttctca cccgtgcca gaatggaggg
2821 acatgtaata acctggtgaa tggctacagg tgtacatgca gaagggggtt caaggctat
2881 aactgccagg tgaacataga tgagtgtgcc tcgaacccgt gtctgaacca agggacctgc
2941 ctcgatgacg tcagtggcta cacctgccac tgcatgctgc cttacacagg caagaattgt
3001 caaacggtgt ggcgccctg ctcccctaac ccgtgtgaga acgctgcagt ttgtaaagag
3061 gcacccaact tgagagctt cacctgcctg tgtgccctg gctggcaagg tcagcgctgt
3121 acagttgacg ttgatgagtg tgtctccaag ccgtgtatga acaatggcat ctgccataat
3181 actcagggca gctacatgtg cgagtgccct ccggcttca gtggtatgga ctgtgaggag
3241 gacatcaatg actgccttgc caaccctgc cagaacggag gctcctgtgt ggacaaagtg
3301 aacaccttct cctgcctgtg ccttcctggc ttcgtagggg acaagtgcca aacagacatg
3361 aatgaatgtc tgagcgagcc ctgtaagaat gggggaccct gctctgacta cgtcaacagc
3421 tacacctgca cgtgccctgc gggcttccat ggagtccact gtgaaaacaa catcgatgag
3481 tgcactgaga gctcctgttt caatggcggc acgtgtgttg atggggatcaa ctcttttctct
3541 tgcttatgcc ctgtgggttt cactggtccc ttctgcctcc atgatatcaa tgagtgcagc
3601 tctaacccgt gcctgaattc gggaacgtgt gttgatggcc tgggtacctac ccgatgcacc
3661 tgtcccttgg gctacactgg gaaaaactgt cagaccctgg tgaacctctg cagcccctct
3721 ccatgtaaaa acaaaggaac ttgtgctcag gaaaaggcaa ggccacgctg cctgtgtccg
3781 cctggatggg atggcgcata ctgtgatgtg ctcaatgtgt cctgtaaggc ggcagccttg
```

Figure 15B

```
3841 cagaaaggag tacctgttga acacttgtgc cagcactcgg gtatctgtat caatgctggc
3901 aacacgcatc actgccagtg cccctgggc tacacgggga gctactgcga ggaacagctt
3961 gacgagtgtg cgtccaatcc atgccagcat ggtgccacct gcagtgactt catcggagga
4021 tacagatgtg agtgtgttcc agggtatcag ggtgtcaact gtgagtatga agtggacgag
4081 tgccagaacc agccctgtca gaacggaggc acctgcatcg acctcgtgaa ccatttcaag
4141 tgctcgtgcc caccaggcac ccggggcctg ctttgtgaag agaacattga tgactgtgct
4201 ggggcccccc actgccttaa tggtggccag tgtgtggacc ggattggagg ctacagttgt
4261 cgctgtttgc ctggctttgc tggggagcgg tgtgagggg acatcaatga atgcctgtcc
4321 aatccttgca gctcagaggg cagcctggac tgcattcagc tcaaaaataa ctaccagtgt
4381 gtctgccgca gcgccttcac aggccgacac tgcgaaacct tcctagatgt gtgtcccag
4441 aagccttgcc tgaatggagg gacttgtgct gtggctagca acgtgcctga tggcttcatt
4501 tgtcgttgtc ccccagggtt ctccggggca agatgccaga gcagctgtgg acaagtgaag
4561 tgcagaagag gggagcagtg tgtgcacacc gcctcgggac cccactgctt ctgcccgaac
4621 cacaaggact gcgagtcagg ttgcgctagt aacccctgcc agcacggagg cacctgctac
4681 cctcagcgcc agcctcctta ctactcttgc cgctgctccc caccgttctg gggcagccac
4741 tgcgagagct acacagcccc caccagc 4767
```

*Figure 16A*

```
  60                                                                          a
  61 tggggctggg ggcccggggc cgccgccgcc gtcgtcgcct gatggccttg ccaccgccac
 121 caccgcccat gcgggcgctg cccctgctgc tgctgctagc ggggctgggg gctgcagcac
 181 cccccttgtct ggatggaagc ccatgtgcaa atggaggtcg gtgcacccac cagcagccct
 241 ccctggaggc tgcttgcctg tgcctgccag gctgggtggg tgagcggtgc cagctggaag
 301 acccttgcca ctcaggccct tgtgctggcc gaggcgtttg ccagagttca gtggtggcgg
 361 gcaccgcccg attctcctgt cgttgtctcc gtggcttcca aggcccagac tgctcccagc
 421 cagacccctg cgtcagcagg ccctgtgttc atggtgcccc ctgctcagtg gggccggatg
 481 gccgatttgc ctgtgcctgc ccacctggct accagggtca aagctgccaa agtgacatag
 541 atgagtgccg atctggtaca acttgccgtc atggtggtac ctgtctcaat acacctggat
 601 ccttccgctg ccagtgtcct cttggttata cagggctgct gtgtgagaac cccgtagtgc
 661 cctgtgcccc ttccccgtgt cgtaatggtg gcacctgtag gcagagcagt gatgtcacat
 721 atgactgtgc ttgccttcct ggcttcgagg gccagaactg tgaagtcaac gtggatgact
 781 gtcctggaca tcggtgtctc aatgggggaa cgtgtgtaga cggtgtcaat acttacaact
 841 gccagtgccc tccggagtgg acaggccagt tctgtacaga agatgtggat gagtgtcagc
 901 tgcagcccaa tgcctgccac aatggggggta cctgcttcaa cctactgggt ggccacagct
 961 gtgtatgtgt caatggctgg acgggtgaga gctgcagtca gaatatcgat gactgtgcta
1021 cagccgtgtg tttccatggg gccacctgcc atgaccgtgt ggcctctttc tactgtgcct
1081 gccctatggg gaagacaggc ctcttgtgtc atctggatga tgcatgtgtc agcaaccccct
1141 gccatgagga tgctatctgt gacacaaacc ctgtgagtgg ccgggccatc tgcacctgcc
1201 cacctggctt cactggaggg gcatgtgacc aggatgtgga tgagtgctcg attggtgcca
1261 acccctgtga acatttgggt cggtgtgtga atacacaggg ctcattcttg tgccaatgtg
1321 gccgtggcta tactggacct cgctgtgaga ctgatgtcaa tgagtgtctc tccgggccct
1381 gccgcaacca ggccacgtgt cttgaccgaa ttggccagtt tacttgcatc tgcatggcag
1441 gcttcacagg gacctactgt gaggtggaca tcgacgaatg tcagagcagc ccatgtgtca
1501 atggtggtgt ctgcaaggac agagtcaatg gcttcagctg cacctgccca tcaggattca
1561 gtgggtccat gtgtcagctg gatgtggatg agtgtcaag cactccctgc cggaatggtg
1621 ccaagtgtgt ggaccagcct gacggctatg agtgtcgctg tgcagagggc tttgagggca
1681 ctttgtgtga gcgaaacgtg gatgactgct ctccggatcc ctgccaccac gggcgctgtg
1741 tcgatggcat tgctagcttc tcgtgtgctt gtgcccagg ctatacgggc atacgctgtg
1801 agagccaggt ggatgagtgc cgcagccagc cctgtcgata tggggcaaa tgtctagact
1861 tggtggacaa gtacctctgc cgttgtcctc ccggaaccac aggtgtgaac tgtgaagtca
1921 acattgatga ctgtgccagt aaccccctgta cctttggagt ttgccgtgat ggcatcaacc
1981 gttatgactg tgtctgtcag cctggattca cagggcccct ctgcaacgtg gagatcaatg
2041 agtgtgcatc cagcccatgt ggagagggtg gctcctgtgt ggatggggaa aatggcttcc
2101 actgcctctg tccacctggc tccctgcctc cactttgcct acctgcgaac catccctgtg
2161 cccacaagcc ctgtagtcat ggagtctgcc atgatgcacc aggcgggttc cgctgtgttt
2221 gtgagcccgg gtggagtggc cctcgctgta gccagagcct ggctccagat gcctgtgagt
2281 cccagccctg ccaggctggt ggcacctgca ccagtgatgg aataggctttt cgctgcacct
2341 gtgcccctgg attccagggc catcagtgtg aggtgctgtc cccctgtact ccaagcctct
2401 gtgagcacgg aggccactgt gagtctgacc ctgaccggct gactgtctgt tcctgtcccc
2461 caggctggca aggcccacga tgccagcagg atgtggatga atgtgccggt gcctcaccct
2521 gcggccccca tggtacctgc accaacctgc cagggaattt caggtgcatc tgccacaggg
2581 gatacactgg ccccttctgt gatcaagaca ttgacgactg tgaccccaac ccgtgcctcc
2641 atggtggctc ctgccaggat ggcgtgggct ccttttcctg ttcttgcctc gacggctttg
2701 ctggtcctcg ctgtgcccga gatgtggacg aatgtctgag cagccctgt ggcctggca
2761 cctgtactga tcacgtggcc tccttcacct gtcctgtcc acctggttat ggaggcttcc
2821 actgtgagat tgacttgccg gactgcagcc ccagttcctg cttcaatgga gggacctgtg
2881 tggatggcgt gagctccttc agctgtctgt gtcgccccgg ctacacaggc acacactgcc
2941 aatacgaggc tgacccctgc ttttcccggc cctgtctgca cggggcatc tgcaaccca
3001 cccacccagg atttgaatgc acctgccggg agggcttcac tgggagtcag tgtcagaacc
3061 cagtggactg gtgcagccag gcaccctgtc agaatggggg tcgctgtgtc cagactgggg
3121 cttactgcat ttgtccacct ggatggagtg gccgcctgtg cgacatacaa agcctgccct
3181 gcacggaggc cgcagcccag atgggggtga ggttggagca gctgtgtcag gaaggtggaa
3241 agtgcataga caagggccgc tccactact gtgtgtgtcc agagggccgt acgggtagtc
3301 actgtgaaca cgaggtggat ccctgcacgg cccagccttg ccagcacggg ggcacttgcc
```

Figure 16B

```
3361 gtggttacat gggggggctat gtgtgtgagt gtccagctgg ctatgctggt gacagttgtg
3421 aggataatat agatgagtgt gcttcccagc cctgccagaa cggaggctcc tgtatcgatc
3481 ttgtggcccg ctatctctgt tcctgtcccc ctggcacact gggagttctc tgtgagatca
3541 atgaggacga ctgtgaccta ggcccatcct tggactcagg cgttcagtgc ctacacaatg
3601 gcacctgtgt ggacctggtg ggtggcttcc gctgtaactg tcccccagga tacacaggtc
3661 tgcactgtga ggcagacatc aatgagtgtc gcccgggtgc ctgccatgca gcgcatactc
3721 gggactgcct acaagatcca ggtgggcatt tccgctgcgt ctgccatcct ggcttcacag
3781 ggcctcgctg tcagattgct ctgtcccct gtgagtccca gccatgtcag catggaggcc
3841 agtgccgtca cagcctaggc cgtggaggtg ggctgacctt cacctgtcac tgtgtcccgc
3901 cattctgggg tctgcgttgt gagcgggtgg cacgctcttg ccgagagctg cagtgcccag
3961 tgggtatccc atgccagcag acagcccgtg gaccacgctg cgcttgtcct ccggggctgt
4021 ccgggccctc ctgccgggtt tctagggcgt caccctcagg agctactaac gccagctgcg
4081 cctctgcccc ttgtctgcat ggggctcat gcctacctgt acagagtgtc cctttcttcc
4141 gctgtgtgtg cgctccgggc tggggcggcc cgcgttgtga gacccctcc gcagcc 4196
```

Figure 17A

```
 117                                                                atgc
 121 agccccagtt gctgctgctg ctgctcttgc cactcaattt ccctgtcatc ctgaccagag
 181 agcttctgtg tggaggatcc ccagagccct gtgccaacgg aggcacctgc ctgaggctat
 241 ctcagggaca agggatctgc cagtgtgccc ctggatttct gggtgagact tgccagtttc
 301 ctgacccctg cagggatacc caactctgca agaatggtgg cagctgccaa gccctgctcc
 361 ccacaccccc aagctcccgt agtcctactt ctccactgac ccctcacttc tcctgcacct
 421 gcccctctgg cttcaccggt gatcgatgcc aaacccatct ggaagagctc tgtccacctt
 481 ctttctgttc caacggggt cactgctatg ttcaggcctc aggccgccca cagtgctcct
 541 gcgagcctgg gtggacaggt gagcaatgcc agctccgaga cttctgctca gccaacccct
 601 gtgccaacgg aggcgtgtgc ctggccacat accccagat ccagtgccgc tgtccacctg
 661 ggttcgaggg tcacacctgt gaacgcgaca tcaacgagtg cttcctggag ccgggaccct
 721 gccctcaggg cacctcctgc ataacacct tgggttccta ccagtgtctc tgccctgtgg
 781 ggcaggaagg tccccagtgc aagctcagga agggagcctg ccctcctgga agctgtctca
 841 atggggcac ctgccagctg gtcccagagg gacactccac ctttcatctc tgcctctgtc
 901 cccaggttt cacggggctg gactgtgaga tgaacccaga tgactgtgtc aggcaccagt
 961 gtcagaacgg ggccacctgt ctggatgggc tggataccta cacctgcctc tgccccaaga
1021 catggaaggg ctgggactgc tctgaagata tagatgaatg tgaagcccgg ggtccccctc
1081 gctgcaggaa cggtggcacc tgccagaaca cagctggcag cttttcactgt gtgtgcgtga
1141 gtggctgggg cggtgcaggt tgtgaggaga acctggatga ctgtgcagct gccacctgtg
1201 ccccgggatc cacctgcatc gaccgtgtgg gctctttctc ctgcctctgc ccacctggac
1261 gcacaggcct cctgtgccac ctggaagaca tgtgtttgag tcagccgtgc cacgtgaatg
1321 cccagtgcag caccaaccct ctgacaggct ccaccctctg catatgccag cctggctact
1381 caggatccac ctgtcaccaa gatctggatg agtgccaaat ggcccagcaa ggacccagtc
1441 cctgcgaaca tggcggctcc tgcatcaaca ccctggctc cttcaactgc ctctgcctgc
1501 ctggttacac gggctcccgc tgtgaagctg accacaatga gtgcctgtca cagccctgcc
1561 acccaggcag cacctgcctg gacctgcttg caaccttcca ctgcctctgc ccaccaggct
1621 tggaagggag gctctgtgag gtggaggtca atgagtgcac ctctaatccc tgcctgaacc
1681 aagctgcctg ccatgacctg ctcaacggct tccagtgcct ctgccttcct ggattcaccg
1741 gcgcccgatg tgagaaagac atggacgagt gtagcagcac ccctgtgcc aatgggggc
1801 gctgccgaga ccagcctgga gccttctact gcgagtgtct cccaggcttt gaagggccac
1861 actgtgagaa agaagtggac gaatgtctga gtgaccctg ccccgtggga gccagctgcc
1921 ttgatctccc cggagcattc ttctgcctct gccgtcctgg tttcacaggt caactttgtg
1981 aggttccctt gtgcaccccc aacatgtgcc aacctggaca gcaatgccaa ggtcaggaac
2041 acagagcccc ctgcctctgc cctgacggaa gtcctggctg tgttcctgcc gaggacaact
2101 gccccctgtca ccatggccat tgccagagat ccttgtgtgt gtgtgatgag ggctggactg
2161 gaccagaatg cgagacagaa ctgggtggct gcatctccac acctgtgcc catgggggga
2221 cctgccaccc acagccgtct ggctacaact gtacctgccc tgcaggctac atgggttga
2281 cctgtagtga ggaggtgaca gcttgtcact cagggccctg tctcaatggt ggctcttgca
2341 gcatccgtcc tgagggctat tcctgcacct gccttccaag tcacacaggt cgccactgcc
2401 agactgccgt ggaccactgt gtgtctgcct cgtgcctcaa tggggtacc tgtgtgaaca
2461 agcctggcac ttttcttctgc ctctgtgcca ctggcttcca ggggctgcac tgtgaggaga
2521 agactaaccc cagctgtgca gacagcccct gcaggaacaa ggcaacctgc caagacacac
2581 ctcgaggggc ccgctgcctc tgcagccctg gctatacagg aagcagctgc cagactctga
2641 tagacttgtg tgcccggaag ccctgtccac acactgctcg atgcctccag agtgggccct
2701 cgttccagtg cctgtgcctc cagggatgga cagggctct ctgtgacttc ccactgtcct
2761 gccagatggc cgcaatgagc caaggcatag agatctctgg cctgtgccag aatggaggcc
2821 tctgtattga cacgggctcc tcctatttct gccgctgccc tcctggattc caaggcaagt
2881 tatgccagga taatatgaac ccctgcgagc caatccctg ccatcacggg tctacctgtg
2941 tgcctcagcc cagtggctat gtctgccagt gtgcccagg ctatgaggga cagaactgct
3001 caaagtact tgaagcttgt cagtcccagc cctgccacaa ccacggaacc tgtacctcca
3061 ggcctggagg cttccactgt gcctgcctc caggcttcgt gggactgcgc tgtgagggag
3121 atgtggatga gtgtctggac cggccctgtc acccctcggg cactgcagct tgccactctt
3181 tagccaacgc cttctactgc cagtgtctgc ctgggcacac aggccagcgg tgtgaggtgg
3241 agatggacct ctgtcagagc caaccctgct ccaatggagg atcctgtgag atcacaacag
3301 ggccacccc tggcttcacc tgtcactgcc ccaagggttt tgaaggcccc acctgcagcc
```

Figure 17B

```
3361 acaaagccct ttcctgcggc atccatcact gccacaatgg aggcctatgt ctgccctccc
3421 ctaagccagg gtcaccacca ctctgtgcct gcctcagtgg ttttgggggc cctgactgtc
3481 tgacacctcc agctccaccg ggctgcggtc cccctcacc ctgcctgcac aatggtacct
3541 gcactgagac ccctggttg ggcaacccgg gctttcaatg cacctgccct cctgactctc
3601 cagggccccg gtgtcaaagg ccaggg.3626
```

Linker sequence

```
GAT CTG GGC CCG GGC
 D   L   G   P   G
```

*Figure 18A*

```
   1 atgccgccgc tcctggcgcc cctgctctgc ctggcgctgc tgcccgcgct cgccgcacga
  61 ggcccgcgat gctcccagcc cggtgagacc tgcctgaatg gcgggaagtg tgaagcggcc
 121 aatggcacgg aggcctgcgt ctgtggcggg gccttcgtgg gcccgcgatg ccaggacccc
 181 aacccgtgcc tcagcacccc ctgcaagaac gccgggacat gccacgtggt ggaccgcaga
 241 ggcgtggcag actatgcctg cagctgtgcc ctgggcttct ctgggcccct ctgcctgaca
 301 cccctggaca atgcctgcct caccaacccc tgccgcaacg ggggcacctg cgacctgctc
 361 acgctgacgg agtacaagtg ccgctgcccg cccggctggt cagggaaatc gtgccagcag
 421 gctgacccgt gcgcctccaa cccctgcgcc aacggtggcc agtgcctgcc cttcgaggcc
 481 tcctacatct gccactgccc acccagcttc atggcccca cctgccggca ggatgtcaac
 541 gagtgtggcc agaagcccgg gctttgccgc cacggaggca cctgccacaa cgaggtcggc
 601 tcctaccgct gcgtctgccg cgccacccac actggcccca actgcgagcg ccctacgtg
 661 ccctgcagcc cctcgccctg ccagaacggg ggcacctgcc gcccacggg cgacgtcacc
 721 cacgagtgtg cctgcctgcc aggcttcacc ggccagaact gtgaggaaaa tatcgacgat
 781 tgtccaggaa acaactgcaa gaacgggggt gcctgtgtgg acggcgtgaa cacctacaac
 841 tgccgctgcc cgccagagtg gacaggtcag tactgtaccg aggatgtgga cgagtgccag
 901 ctgatgccaa atgcctgcca gaacggcggg acctgccaca caccacgg tggctacaac
 961 tgcgtgtgtg tcaacggctg gactggtgag gactgcagcg agaacattga tgactgtgcc
1021 agcgccgcct gcttccacgg cgccacctgc catgaccgtg tggcctcctt ctactgcgag
1081 tgtcccccatg gccgcacagg tctgctgtgc cacctcaacg acgcatgcat cagcaacccc
1141 tgtaacgagg gctccaactg cgacaccaac cctgtcaatg caaggccat ctgcacctgc
1201 ccctcggggt acacgggccc ggcctgcagc caggacgtgg atgagtgctc gctgggtgcc
1261 aaccccctgcg agcatgcggg caagtgcatc aacacgctgg gctccttcga gtgccagtgt
1321 ctgcagggct acacgggccc ccgatgcgag atcgacgtca acgagtgcgt ctcgaacccg
1381 tgccagaacg acgccacctg cctggaccag attggggagt ccagtgcat ctgcatgccc
1441 ggctacgagg tgtgcactg cgaggtcaac acagacgagt gtgccagcag ccctgcctg
1501 cacaatggcc gctgcctgga caagatcaat gagttccagt gcgagtgccc cacgggcttc
1561 actgggcatc tgtgccagta cgatgtggac gagtgtgcca gcaccccctg caagaatggt
1621 gccaagtgcc tggacggacc caacacttac acctgtgtgt gcacggaagg gtacacgggg
1681 acgcactgcg aggtggacat cgatgagtgc gaccccgacc cctgccacta cggctcctgc
1741 aaggacggcg tcgccacctt cacctgcctc tgccgcccag gctacacggg ccaccactgc
1801 gagaccaaca tcaacgagtg ctccagccag ccctgccgcc acggggcac ctgccaggac
1861 cgcgacaacg cctacctctg cttctgcctg aaggggacca caggacccaa ctgcgagatc
1921 aacctggatg actgtgccag cagcccctgc gactcgggca cctgtctgga caagatcgat
1981 ggctacgagt gtgcctgtga gccgggctac acagggagca tgtgtaacat caacatcgat
2041 gagtgtgcgg gcaaccctg ccacaacggg ggcacctgcg aggacggcat caatggcttc
2101 acctgccgct gccccgaggg ctaccacgac cccacctgcc tgtctgaggt caatgagtgc
2161 aacagcaacc cctgcgtcca cggggcctgc cgggacagcc tcaacgggta caagtgcgac
2221 tgtgaccctg ggtggagtgg gaccaactgt gacatcaaca acaatgagtg taatccaac
2281 ccttgtgtca acggcggcac ctgcaaagac atgaccagtg gctacgtgtg cacctgccgg
2341 gagggcttca gcggtccaa ctgccagacc aacatcaacg agtgtgcgtc caacccatgt
2401 ctgaaccagg gcacgtgtat tgacgacgtt gccgggtaca agtgcaactg cctgctgccc
2461 tacacaggtg ccacgtgtga ggtggtgctg gccccgtgtg ccccagccc ctgcagaaac
2521 ggcggggagt gcaggcaatc cgaggactat gagagcttct cctgtgtctg ccccacgggc
2581 tggcaagcag ggcagacctg tgaggtcgac atcaacgagt gcgttctgag cccgtgccgg
2641 cacggcgcat cctgccagaa cacccacggc ggctaccgct gccactgcca ggccggctac
2701 agtgggcgca actgcgagac cgacatcgac gactgccggc caacccgtg tcacaacggg
2761 ggctcctgca cagacggcat caacacggcc ttctgcgact gcctgcccgg cttcggggc
2821 actttctgtg aggaggacat caacgagtgt gccagtgacc cctgccgcaa cggggccaac
2881 tgcacggact gcgtggacag ctacacgtgc acctgccccg caggcttcag cgggatccac
2941 tgtgagaaca acacgcctga ctgcacagag agctcctgct caacggtgg cacctgcgtg
3001 gacggcatca actcgttcac ctgcctgtgt ccacccggct caccgggcag ctactgccag
3061 cacgatgtca atgagtgcga ctcacagccc tgcctgcatg gcggcacctg tcaggacggc
3121 tgcggctcct acaggtgcac ctgccccag ggctacactg ccccaactg ccagaacctt
3181 gtgcactggt gtgactcctc gccctgcaag aacggcggca atgctggca gacccacacc
3241 cagtaccgct gcgagtgccc cagcggctgg accggccttt actgcgacgt gcccagcgtg
3301 tcctgtgagg tggctgcgca gcgacaaggt gttgacgttg cccgcctgtg ccagcatgga
```

Figure 18B

```
3361 gggctctgtg tggacgcggg caacacgcac cactgccgct gccaggcggg ctacacaggc
3421 agctactgtg aggacctggt ggacgagtgc tcacccagcc cctgccagaa cggggccacc
3481 tgcacggact acctgggcgg ctactcctgc aagtgcgtgg ccggctacca cggggtgaac
3541 tgctctgagg agatcgacga gtgcctctcc cacccctgcc agaacggggg cacctgcctc
3601 gacctcccca acacctacaa gtgctcctgc ccacggggca ctcagggtgt gcactgtgag
3661 atcaacgtgg acgactgcaa tcccccgtt gacccgtgt cccggagccc caagtgcttt
3721 aacaacggca cctgcgtgga ccaggtgggc ggctacagct gcacctgccc gccgggcttc
3781 gtgggtgagc gctgtgaggg ggatgtcaac gagtgcctgt ccaatccctg cgacgcccgt
3841 ggcacccaga actgcgtgca gcgcgtcaat gacttccact gcgagtgccg tgctggtcac
3901 accgggcgcc gctgcgagtc cgtcatcaat ggctgcaaag gcaagccctg caagaatggg
3961 ggcacctgcg ccgtggcctc caacaccgcc cgcgggttca tctgcaagtg ccctgcgggc
4021 ttcgagggcg ccacgtgtga aatgacgct cgtacctgcg gcagcctgcg ctgcctcaac
4081 ggcggcacat gcatctccgg cccgcgcagc cccacctgcc tgtgcctggg cccttcacg
4141 ggccccgaat gccagttccc ggccagcagc cctgcctgg gcggcaaccc ctgctacaac
4201 caggggacct gtgagcccac atccgagagc cccttctacc gttgcctgtg ccccgccaaa
     4261 ttcaacgggc tcttgtgcca catcctggac tacagcttc 4299
```

Figure 19A

```
  13            atgcccgc cctgcgcccc gctctgctgt gggcgctgct ggcgctctgg
  61 ctgtgctgcg cggccccgc gcatgcattg cagtgtcgag atggctatga accctgtgta
 121 aatgaaggaa tgtgtgttac ctaccacaat ggcacaggat actgcaaatg tccagaaggc
 181 ttcttggggg aatattgtca acatcgagac ccctgtgaga agaaccgctg ccagaatggt
 241 gggacttgtg tggcccaggc catgctgggg aaagccacgt gccgatgtgc ctcagggttt
 301 acaggagagg actgccagta ctcaacatct catccatgct ttgtgtctcg accctgcctg
 361 aatggcggca catgccatat gctcagccgg gatacctatg agtgcacctg tcaagtcggg
 421 tttacaggta aggagtgcca atggacggat gcctgcctgt ctcatccctg tgcaaatgga
 481 agtacctgta ccactgtggc caaccagttc tcctgcaaat gcctcacagg cttcacaggg
 541 cagaaatgtg agactgatgt caatgagtgt gacattccag acactgcca gcatggtggc
 601 acctgcctca acctgcctgg ttcctaccag tgccagtgcc ctcagggctt cacaggccag
 661 tactgtgaca gcctgtatgt gccctgtgca ccctcacctt gtgtcaatgg aggcacctgt
 721 cggcagactg gtgacttcac ttttgagtgc aactgccttc aggttttga agggagcacc
 781 tgtgagagga atattgatga ctgccctaac cacaggtgtc agaatggagg ggtttgtgtg
 841 gatggggtca acacttacaa ctgccgctgt cccccacaat ggacaggaca gttctgcaca
 901 gaggatgtgg atgaatgcct gctgcagccc aatgcctgtc aaaatggggg cacctgtgcc
 961 aaccgcaatg gaggctatgg ctgtgtatgt gtcaacggct ggagtggaga tgactgcagt
1021 gagaacattg atgattgtgc cttcgcctcc tgtactccag gctccacctg catcgaccgt
1081 gtggcctcct tctcttgcat gtgcccagag gggaaggcag gtctcctgtg tcatctggat
1141 gatgcatgca tcagcaatcc ttgccacaag ggggcactgt gtgacaccaa ccccctaaat
1201 gggcaatata tttgcacctg cccacaaggc tacaaagggg ctgactgcac agaagatgtg
1261 gatgaatgtg ccatggccaa tagcaatcct tgtgagcatg caggaaaatg tgtgaacacg
1321 gatggcgcct tccactgtga gtgtctgaag ggttatcag gacctcgttg tgagatggac
1381 atcaatgagt gccattcaga cccctgccag aatgatgcta cctgtctgga taagattgga
1441 ggcttcacat gtctgtgcat gccaggtttc aaaggtgtgc attgtgaatt agaaataaat
1501 gaatgtcaga gcaacccttg tgtgaacaat gggcagtgtg tggataaagt caatcgtttc
1561 cagtgcctgt gtcctcctgg tttcactggg ccagtttgcc agattgatat tgatgactgt
1621 tccagtactc cgtgtctgaa tgggcaaag tgtatcgatc acccgaatgg ctatgaatgc
1681 cagtgtgcca caggtttcac tggtgtgttg tgtgaggaga acattgacaa ctgtgacccc
1741 gatccttgcc accatggtca gtgtcaggat ggtattgatt cctacacctg catctgcaat
1801 cccgggtaca tgggcgccat ctgcagtgac cagattgatg aatgttacag cagcccttgc
1861 ctgaacgatg gtcgctgcat tgacctggtc aatggctacc agtgcaactg ccagccaggc
1921 acgtcagggg ttaattgtga aattaatttt gatgactgtg caagtaaccc ttgtatccat
1981 ggaatctgta tggatggcat taatcgctac agttgtgtct gctcaccagg attcacaggg
2041 cagagatgta cattgacat tgatgagtgt gcctccaatc cctgtcgcaa gggtgcaaca
2101 tgtatcaacg gtgtgaatgg tttccgctgt atatgccccg agggacccca tcacccagc
2161 tgctactcac aggtgaacga atgcctgagc aatccctgca tccatggaaa ctgtactgga
2221 ggtctcagtg gatataagtg tctctgtgat gcaggctggg ttggcatcaa ctgtgaagtg
2281 gacaaaaatg aatgcctttc gaatccatgc cagaatggag gaacttgtga caatctggtg
2341 aatggataca ggtgtacttg cagaaggggc tttaaggct ataactgcca ggtgaatatt
2401 gatgaatgtg cctcaaatcc atgcctgaac aaggaacct gctttgatga cataagtggc
2461 tacacttgcc actgtgtgct gccatacaca ggcaagaatt gtcagacagt attggctccc
2521 tgttccccaa acccttgtga gaatgctgct gtttgcaaag agtcaccaaa ttttgagagt
2581 tatacttgct tgtgtgctcc tggctggcaa ggtcagcggt gtaccattga cattgacgag
2641 tgtatctcca gccctgcat gaaccatggt ctctgccata cacccaggg cagctacatg
2701 tgtaatgtc caccaggctt cagtggtatg gactgtgagg aggacattga tgactgcctt
2761 gccaatcctt gccagaatgg aggttcctgt atggatggag tgaatacttt ctcctgcctc
2821 tgccttccgg gtttcactgg ggataagtgc cagacagaca tgaatgagtg tctgagtgaa
2881 ccctgtaaga atggagggac tgctctgac tacgtcaaca gttacacttg caagtgccag
2941 gcaggatttg atggagtcca ttgtgagaac aacatcaatg agtgcactga gctcctgt
3001 ttcatggtg gcacatgtgt tgatgggatt aactccttct cttgcttgtg ccctgtgggt
3061 ttcactggat ccttctgcct ccatgagatc aatgaatgca gctctcatcc atgcctgaat
3121 gagggaacgt gtgttgatgg cctgggtacc taccgctgca gctgccccct gggctacact
3181 gggaaaaact gtcagaccct ggtgaatctc tgcagtcggt ctccatgtaa aaacaaaggt
3241 acttgtgttc agaaaaaagc agagtcccag tgcctatgtc catctggatg ggctggtgcc
```

Figure 19B

```
3301 tattgtgacg tgcccaatgt ctcttgtgac atagcagcct ccaggagagg tgtgcttgtt
3361 gaacacttgt gccagcactc aggtgtctgc atcaatgctg gcaacacgca ttactgtcag
3421 tgcccctgg  gctatactgg gagctactgt gaggagcaac tcgatgagtg tgcgtccaac
3481 ccctgccagc acggggcaac atgcagtgac ttcattggtg gatacagatg cgagtgtgtc
3541 ccaggctatc agggtgtcaa ctgtgagtat gaagtggatg agtgccagaa tcagccctgc
3601 cagaatggag gcacctgtat tgaccttgtg aaccatttca agtgctcttg cccaccaggc
3661 actcggggcc tactctgtga agagaacatt gatgactgtg cccggggtcc ccattgcctt
3721 aatggtggtc agtgcatgga taggattgga ggctacagtt gtcgctgctt gcctggcttt
3781 gctggggagc gttgtgaggg agacatcaac gagtgcctct ccaacccctg cagctctgag
3841 ggcagcctgg actgtataca gctcaccaat gactacctgt gtgtttgccg tagtgccttt
3901 actggccggc actgtgaaac cttcgtcgat gtgtgtcccc agatgcctg  cctgaatgga
3961 gggacttgtg ctgtggccag taacatgcct gatggtttca tttgccgttg tccccggga
4021 ttttccgggg caaggtgcca gagcagctgt ggacaagtga aatgtaggaa gggggagcag
4081 tgtgtgcaca ccgcctctgg acccgctgc  ttctgcccca gtccccggga ctgcgagtca
4141 ggctgtgcca gtagcccctg ccagcacggg ggcagctgcc accctcagcg ccagcctcct
     4201 tattactcct gcc 4213
```

Figure 20A

```
  77                     atgg ggccggggc ccgtggccgc cgccgccgcc gtcgcccgat
 121 gtcgccgcca ccgccaccgc cacccgtgcg ggcgctgccc ctgctgctgc tgctagcggg
 181 gccgggggct gcagcccccc cttgcctgga cggaagcccg tgtgcaaatg gaggtcgttg
 241 cacccagctg ccctcccggg aggctgcctg cctgtgcccg cctggctggg tgggtgagcg
 301 gtgtcagctg gaggacccct gtcactcagg ccctgtgct ggccgtggtg tctgccagag
 361 ttcagtggtg gctggcaccg cccgattctc atgccggtgc ccccgtggct tccgaggccc
 421 tgactgctcc ctgccagatc cctgcctcag cagcccttgt gccacggtg cccgctgctc
 481 agtggggccc gatggacgct tcctctgctc ctgcccacct ggctaccagg gccgcagctg
 541 ccgaagcgac gtggatgagt gccggtggg tgagccctgc cgccatggtg gcacctgcct
 601 caacacacct ggctccttcc gctgccagtg tccagctggc tacacagggc cactatgtga
 661 gaaccccgcg gtgccctgtg cacctcacc atgccgtaac gggggcacct gcaggcagag
 721 tggcgacctc acttacgact gtgcctgtct tcctgggttt gagggtcaga attgtgaagt
 781 gaacgtggac gactgtccag gacaccgatg tctcaatggg gggacatgcg tggatggcgt
 841 caacacctat aactgccagt gccctcctga gtggacaggc cagttctgca cggaggacgt
 901 ggatgagtgt cagctgcagc ccaacgcctg ccacaatggg ggtacctgct caacacgct
 961 gggtggccac agctgcgtgt gtcaatgg ctggacaggc gagagctgca gtcagaatat
1021 cgatgactgt gccacagccg tgtgcttcca tggggccacc tgccatgacc gcgtggcttc
1081 tttctactgt gcctgcccca tgggcaagac tggcctcctg tgtcacctgg atgacgcctg
1141 tgtcagcaac cctgccacg aggatgctat ctgtgacaca aatccggtga acggccgggc
1201 catttgcacc tgtcctcccg gcttcacggg tggggcatgt gaccaggatg tggacgagtg
1261 ctctatcggc gccaacccct gcgagcactt gggcaggtgc gtgaacacgc agggctcctt
1321 cctgtgccag tgcggtcgtg gctacactgg acctcgctgt gagaccgatg tcaacgagtg
1381 tctgtcgggg ccctgccgaa accaggccac gtgcctcgac cgcataggcc agttcacctg
1441 tatctgtatg gcaggcttca caggaaccta ttgcgaggtg gacattgacg agtgtcagag
1501 tagccctgt gtcaacggtg gggtctgcaa ggaccgagtc aatggcttca gctgcacctg
1561 cccctcgggc ttcagcggct ccacgtgtca gctggacgtg gacgaatgcg ccagcacgcc
1621 ctgcaggaat ggcgccaaat gcgtggacca gcccgatggc tacgagtgcc gctgtgccga
1681 gggctttgag ggcacgctgt gtgatcgcaa cgtggacgac tgctccctg acccatgcca
1741 ccatggtcgc tgcgtggatg gcatcgccag cttctcatgt gcctgtgctc ctggctacac
1801 gggcacacgc tgcgagagcc aggtggacga atgccgcagc agccctgcc gccatggcgg
1861 caaatgccta gacctggtgg acaagtacct ctgccgctgc cttctggga ccacaggtgt
1921 gaactgcgaa gtgaacattg acgactgtgc cagcaacccc tgcaccttg gagtctgccg
1981 tgatggcatc aaccgctacg actgtgtctg ccaacctggc ttcacagggc cctttgtaa
2041 cgtggagatc aatgagtgtg cttccagccc atgcggcgag ggaggttcct gtgtggatgg
2101 ggaaaatggc ttccgctgcc tctgccgcc tggctccttg cccccactct gcctcccccc
2161 gagccatccc tgtgccatg agccctgcag tcacggcatc tgctatgatg cacctggcgg
2221 gttccgctgt gtgtgtgagc ctggctggag tggcccccgc tgcagccaga gcctggcccg
2281 agacgcctgt gagtcccagc cgtgcagggc cggtgggaca tgcagcagcg atggaatggg
2341 tttccactgc acctgcccgc ctggtgtcca gggacgtcag tgtgaactcc tctccccctg
2401 caccccgaac ccctgtgagc atggggccg ctgcgagtct gccctggcc agctgcctgt
2461 ctgctcctgc ccccagggct ggcaaggccc acgatgccag caggatgtgg acgagtgtgc
2521 tggccccgca ccctgtggcc ctcatggtat ctgcaccaac ctggcaggga gtttcagctg
2581 cacctgccat ggagggtaca ctggcccttc ctgcgatcag gacatcaatg actgtgaccc
2641 caaccccatgc ctgaacggtg gctcgtgcca agacggcgtg ggctcctttt cctgctcctg
2701 cctccctggt ttcgccggcc cacgatgcgc ccgcgatgtg gatgagtgcc tgagcaaccc
2761 ctgcggcccg ggcacctgta ccgaccacgt ggcctccttc acctgcacct gcccgccagg
2821 ctacggaggc ttccactgcg aacaggacct gcccgactgc agcccagct cctgcttcaa
2881 tggcgggacc tgtgtggacg gcgtgaactc gttcagctgc ctgtgccgtc ccggctacac
2941 aggagcccac tgccaacatg aggcagaccc ctgcctctcg cggccctgcc tacacggggg
3001 cgtctgcagc gccgcccacc ctggcttccg ctgcacctgc ctcgagagct tcacgggccc
3061 gcagtgccag acgctggtgg attggtgcag ccgccagcct tgtcaaaacg ggggtcgctg
3121 cgtccagact ggggcctatt gcctttgtcc cctggatgg agcggacgcc tctgtgacat
3181 ccgaagcttg ccctgcaggg aggccgcagc caagatcggg gtgcggctgg agcagctgtg
3241 tcaggcgggt gggcagtgtg tggatgaaga cagctcccac tactgcgtgt gcccagaggg
3301 ccgtactggt agccactgtg agcaggaggt ggacccctgc ttggcccagc cctgccagca
```

Figure 20B

```
3361  tgggggacc  tgccgtggct  atatgggggg  ctacatgtgt  gagtgtcttc  ctggctacaa
3421  tggtgataac  tgtgaggacg  acgtggacga  gtgtgcctcc  cagccctgcc  agcacggggg
3481  ttcatgcatt  gacctcgtgg  cccgctatct  ctgctcctgt  ccccaggaa  cgctgggggt
3541  gctctgcgag  attaatgagg  atgactgcgg  cccaggccca  ccgctggact  cagggccccg
3601  gtgcctacac  aatggcacct  gcgtggacct  ggtgggtggt  ttccgctgca  cctgtccccc
3661  aggatacact  ggtttgcgct  gcgaggcaga  catcaatgag  tgtcgctcag  gtgcctgcca
3721  cgcggcacac  acccgggact  gcctgcagga  cccaggcgga  ggtttccgtt  gcctttgtca
3781  tgctggcttc  tcaggtcctc  gctgtcagac  tgtcctgtct  ccctgcgagt  cccagccatg
3841  ccagcatgga  ggccagtgcc  gtcctagccc  gggtcctggg  ggtgggctga  ccttcacctg
3901  tcactgtgcc  cagccgttct  ggggtccgcg  ttgcgagcgg  gtggcgcgct  cctgccggga
3961  gctgcagtgc  ccggtgggcg  tcccatgcca  gcagacgccc  cgcgggccgc  gctgcgcctg
4021  cccccaggg  ttgtcgggac  cctcctgccg  4050
```

Figure 21A

```
  91                                         atgcagcccc cttcactgct gctgctgctg
 121 ctgctgctgc tgctgctatg tgtctcagtg gtcagaccca gagggctgct gtgtgggagt
 181 ttcccagaac cctgtgccaa tggaggcacc tgcctgagcc tgtctctggg acaagggacc
 241 tgccagtgtg cccctggctt cctgggtgag acgtgccagt ttcctgaccc ctgccagaac
 301 gcccagctct gccaaaatgg aggcagctgc aagccctgc ttcccgctcc cctagggctc
 361 cccagctctc cctctccatt gacacccagc ttcttgtgca cttgcctccc tggcttcact
 421 ggtgagagat gccaggccaa gcttaagac ccttgtcctc cctccttctg ttccaaaagg
 481 ggccgctgcc acatccaggc ctcgggccgc ccacagtgct cctgcatgcc tggatggaca
 541 ggtgagcagt gccagcttcg ggacttctgt tcagccaacc catgtgttaa tggaggggtg
 601 tgtctggcca catacccca gatccagtgc cactgccac cgggcttcga gggccatgcc
 661 tgtgaacgtg atgtcaacga gtgcttccag gacccaggac cctgcccaa aggcacctcc
 721 tgccataaca ccctgggctc cttccagtgc ctctgccctg tggggcagga gggtccacgt
 781 tgtgagctgc gggcaggacc ctgccctcct aggggctgtt cgaatggggg cacctgccag
 841 ctgatgccag agaaagactc cacctttcac ctctgcctct gtccccagg tttcataggc
 901 ccagactgtg aggtgaatcc agacaactgt gtcagccacc agtgtcagaa tgggggcact
 961 tgccaggatg ggctggacac ctacacctgc ctctgccag aaacctggac aggctgggac
1021 tgctccgaag atgtggatga gtgtgagacc cagggtcccc ctcactgcag aaacggggc
1081 acctgccaga actctgctgg tagctttcac tgcgtgtgtg tgagtggctg gggcggcaca
1141 agctgtgagg agaacctgga tgactgtatt gctgccacct gtgccccggg atccacctgc
1201 attgaccggg tgggctcttt ctcctgcctc tgcccacctg gacgcacagg actcctgtgc
1261 cacttggaag acatgtgtct gagccagccg tgccatgggg atgcccaatg cagcaccaac
1321 cccctcacag gctccacact ctgcctgtgt cagcctggct attcggggcc cacctgccac
1381 caggacctgg acgagtgtct gatgcccag caaggcccaa gtccctgtga acatggcggt
1441 tcctgcctca acactcctgg ctccttcaac tgcctctgtc cacctggcta cacaggctcc
1501 cgttgtgagg ctgatcacaa tgagtgcctc tcccagccct gccacccagg aagcacctgt
1561 ctggacctac ttgccacctt ccactgcctc tgcccgccag gcttagaagg gcagctctgt
1621 gaggtggaga ccaacgagtg tgcctcagct ccctgcctga ccacgcgga ttgccatgac
1681 ctgctcaacg gcttccagtg catctgcctg cctggattct ccggcacccg atgtgaggag
1741 gatatcgatg agtgcagaag ctctccctgt gccaatggtg ggcagtgcca ggaccagcct
1801 ggagccttcc actgcaagtg tctcccaggc tttgaagggc cacgctgtca acagaggtg
1861 gatgagtgcc tgagtgaccc atgtccgtt ggagccagct gccttgatct tccaggagcc
1921 ttcttttgcc tctgcccctc tggtttcaca ggccagctct gtgaggttcc cctgtgtgct
1981 cccaacctgt gccagcccaa gcagatatgt aaggaccaga aagacaaggc caactgcctc
2041 tgtcctgatg gaagccctgg ctgtgcccca cctgaggaca actgcacctg ccaccacggg
2101 cactgccaga gatcctcatg tgtgtgtgac gtgggttgga cggggccaga gtgtgaggca
2161 gagctagggg gctgcatctc tgcaccctgt gccatgggg ggacctgcta ccccagccc
2221 tctggctaca actgcacctg ccctacaggc tacacaggac ccacctgtag tgaggagatg
2281 acagcttgtc actcagggcc atgtcaat ggcggctcct gcaaccctag ccctggaggc
2341 tactactgca cctgccctcc aagccacaca gggcccagt gccaaaccag cactgactac
2401 tgtgtgtctg ccccgtgctt caatggggt acctgtgtga acaggcctgg caccttctcc
2461 tgcctctgtg ccatgggctt ccagggcccg cgctgtgagg gaaagctccg ccccagctgt
2521 gcagacagcc cctgtaggaa tagggcaacc tgccaggaca gccctcaggg tcccgctgc
2581 ctctgcccca ctggctacac cggaggcagc tgccagactc tgatggactt atgtgcccag
2641 aagccctgcc cacgcaattc ccactgcctc cagactgggc cctccttcca ctgcttgtgc
2701 ctccagggat ggaccgggcc tctctgcaac cttccactgt cctcctgcca gaaggctgca
2761 ctgagccaag gcatagacgt ctcttccctt gccacaatg gaggcctctg tgtcgacagc
2821 ggcccctcct atttctgcca ctgccccct ggattccaag gcagcctgtg ccaggatcac
2881 gtgaacccat gtgagtccag gccttgccag aacgggggcca cctgcatggc ccagcccagt
2941 gggtatctct gccagtgtgc cccaggctac gatggacaga actgctcaaa ggaactcgat
3001 gcttgtcagt cccaaccctg tcacaaccat ggaacctgta ctcccaaacc tggaggattc
3061 cactgtgcct gccctccagg ctttgtgggg ctacgctgtg agggagacgt ggacgagtgt
3121 ctggaccagc cctgccaccc cacaggcact gcagcctgcc actctctggc caatgccttc
3181 tactgccagt gtctgcctgg acacacaggc cagtggtgtg aggtggagat agaccctgc
3241 cacagccaac cctgctttca tggagggacc tgtgaggcca cagcaggatc acccctgggt
3301 ttcatctgcc actgccccaa gggttttgaa ggccccacct gcagccacag ggccccttcc
```

Figure 21B

```
3361 tgcggcttcc atcactgcca ccacggaggc ctgtgtctgc cctcccctaa gccaggcttc
3421 ccaccacgct gtgcctgcct cagtggctat gggggtcctg actgcctgac cccaccagct
3481 cctaaaggct gtggccctcc ctccccatgc ctatacaatg gcagctgctc agagaccacg
3541 ggcttggggg gcccaggctt tcgatgctcc tgccctcaca gctctccagg gccccggtgt
3601 cagaaacccg ga
```

*Figure 23G*
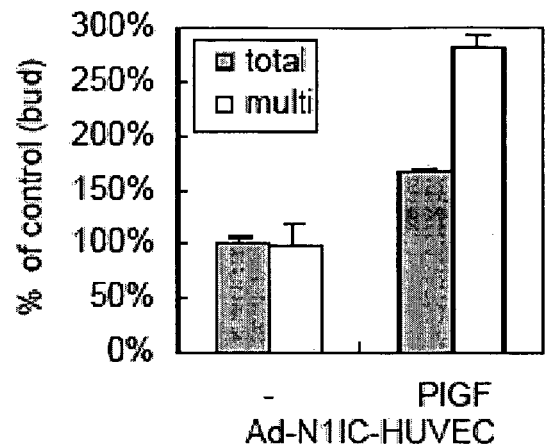
*Figure 23H*          *Figure 23I*
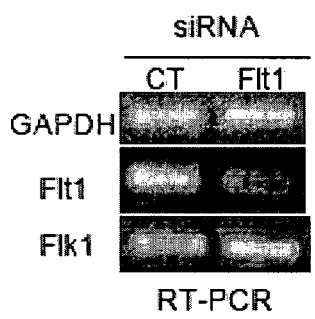     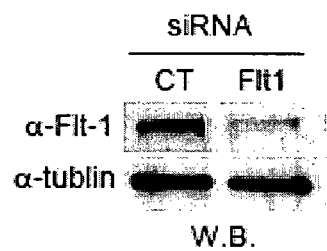
*Figure 23J*
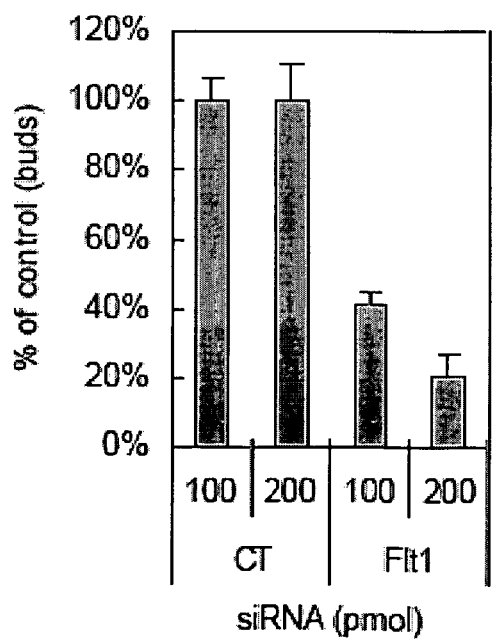

*Figure 28A*  *Figure 28B*
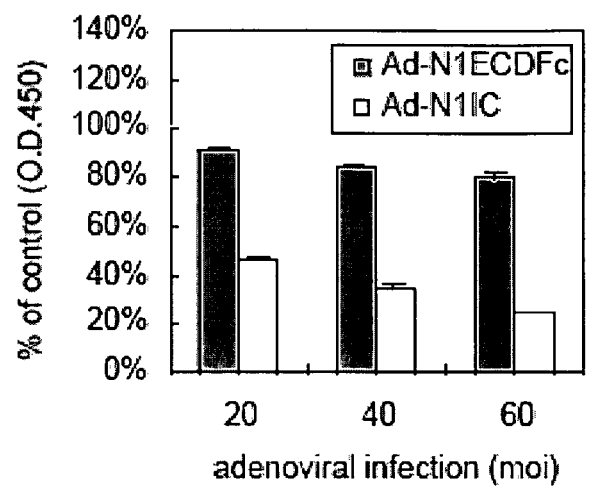
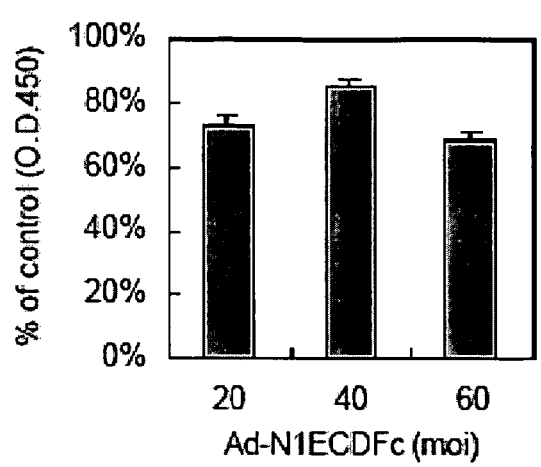
*Figure 29*
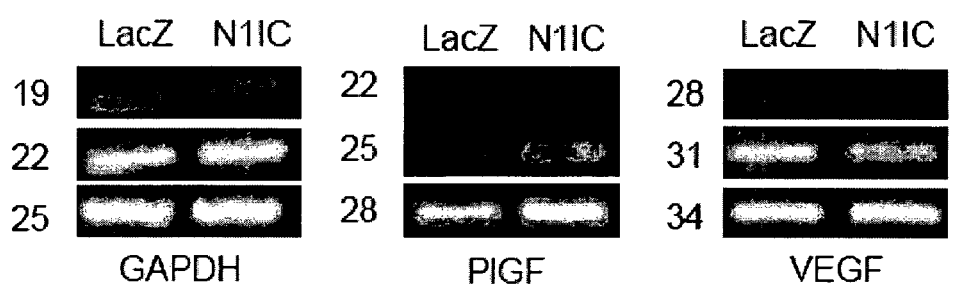

SEQUENCE LISTING

```
<160> NUMBER OF SEQ ID NOS: 14

<210> SEQ ID NO 1
<211> LENGTH: 1433
<212> TYPE: PRT
<213> ORGANISM: Rattus norvegius

<400> SEQUENCE: 1

Met Pro Arg Leu Leu Ala Pro Leu Leu Cys Leu Thr Leu Leu Pro Ala
1               5                   10                  15

Leu Ala Ala Arg Gly Leu Arg Cys Ser Gln Pro Ser Gly Thr Cys Leu
                20                  25                  30

Asn Gly Gly Arg Cys Glu Val Ala Asn Gly Thr Glu Ala Cys Val Cys
            35                  40                  45

Ser Gly Ala Phe Val Gly Gln Arg Cys Gln Asp Pro Ser Pro Cys Leu
        50                  55                  60

Ser Thr Pro Cys Lys Asn Ala Gly Thr Cys Tyr Val Val Asp His Gly
65                  70                  75                  80

Gly Ile Val Asp Tyr Ala Cys Ser Cys Pro Leu Gly Phe Ser Gly Pro
                85                  90                  95
```

```
Leu Cys Leu Thr Pro Leu Ala Asn Ala Cys Leu Ala Asn Pro Cys Arg
            100                 105                 110
Asn Gly Gly Thr Cys Asp Leu Leu Thr Leu Thr Glu Tyr Lys Cys Arg
            115                 120                 125
Cys Pro Pro Gly Trp Ser Gly Lys Ser Cys Gln Gln Ala Asp Pro Cys
            130                 135                 140
Ala Ser Asn Pro Cys Ala Asn Gly Gly Gln Cys Leu Pro Phe Glu Ser
145                 150                 155                 160
Ser Tyr Ile Cys Gly Cys Pro Pro Gly Phe His Gly Pro Thr Cys Arg
                165                 170                 175
Gln Asp Val Asn Glu Cys Ser Gln Asn Pro Gly Leu Cys Arg His Gly
            180                 185                 190
Gly Thr Cys His Asn Glu Ile Gly Ser Tyr Arg Cys Ala Cys Arg Ala
            195                 200                 205
Thr His Thr Gly Pro His Cys Glu Leu Pro Tyr Val Pro Cys Ser Pro
            210                 215                 220
Ser Pro Cys Gln Asn Gly Gly Thr Cys Arg Pro Thr Gly Asp Thr Thr
225                 230                 235                 240
His Glu Cys Ala Cys Leu Pro Gly Phe Ala Gly Gln Asn Cys Glu Glu
                245                 250                 255
Asn Val Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
            275                 280                 285
Gly Gln Tyr Cys Thr Glu Asp Val Asp Glu Cys Gln Leu Met Pro Asn
            290                 295                 300
Ala Cys Gln Asn Ala Gly Thr Cys His Asn Ser His Gly Gly Tyr Asn
305                 310                 315                 320
Cys Val Cys Val Asn Gly Trp Thr Gly Glu Asp Cys Ser Asp Asn Ile
                325                 330                 335
Asp Asp Cys Ala Ser Ala Ala Cys Phe Gln Gly Ala Thr Cys His Asp
            340                 345                 350
Arg Val Ala Ser Phe Tyr Cys Glu Cys Pro His Gly Arg Thr Gly Leu
            355                 360                 365
Leu Cys His Leu Asn Asp Ala Cys Ile Ser Asn Pro Cys Asn Glu Gly
            370                 375                 380
Ser Asn Cys Asp Thr Asn Pro Val Asn Gly Lys Ala Ile Cys Thr Cys
385                 390                 395                 400
Pro Arg Gly Tyr Thr Gly Pro Ala Cys Ser Gln Asp Val Asp Glu Cys
                405                 410                 415
Ala Leu Gly Ala Asn Pro Cys Glu His Ala Gly Lys Cys Leu Asn Thr
            420                 425                 430
Leu Gly Ser Phe Glu Cys Gln Cys Leu Gln Gly Tyr Thr Gly Pro Arg
            435                 440                 445
Cys Glu Ile Asp Val Asn Glu Cys Ile Ser Asn Pro Cys Gln Asn Asp
            450                 455                 460
Ala Thr Cys Leu Asp Gln Ile Gly Glu Phe Gln Cys Ile Cys Met Pro
465                 470                 475                 480
Gly Tyr Glu Gly Val Tyr Cys Glu Ile Asn Thr Asp Glu Cys Ala Ser
                485                 490                 495
Ser Pro Cys Leu His Asn Gly Arg Cys Val Asp Lys Ile Asn Glu Phe
            500                 505                 510
Leu Cys Gln Cys Pro Lys Gly Phe Ser Gly His Leu Cys Gln Tyr Asp
```

-continued

```
            515                 520                 525
Val Asp Glu Cys Ala Ser Thr Pro Cys Lys Asn Gly Ala Lys Cys Leu
            530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                    565                 570                 575

Ile Gly Leu Cys Lys Asp Gly Val Ala Thr Phe Thr Cys Leu Cys Gln
                580                 585                 590

Pro Gly Tyr Thr Gly His His Cys Glu Thr Asn Ile Asn Glu Cys His
            595                 600                 605

Ser Gln Pro Cys Arg His Gly Gly Thr Cys Gln Asp Arg Asp Asn Tyr
    610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                    645                 650                 655

Asp Lys Ile Asp Gly Tyr Glu Cys Ala Cys Glu Pro Gly Tyr Thr Gly
                660                 665                 670

Ser Met Cys Asn Val Asn Ile Asp Glu Cys Ala Gly Ser Pro Cys His
            675                 680                 685

Asn Gly Gly Thr Cys Glu Asp Gly Ile Ala Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Ile His Gly Ala Cys Arg Asp Gly Leu Asn Gly
                    725                 730                 735

Tyr Lys Cys Asp Cys Ala Pro Gly Trp Ser Gly Thr Asn Cys Asp Ile
                740                 745                 750

Asn Asn Asn Glu Cys Glu Ser Asn Pro Cys Val Asn Gly Gly Thr Cys
            755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                    805                 810                 815

Cys Pro Leu Pro Tyr Thr Gly Ala Thr Cys Glu Val Val Leu Ala Pro
                820                 825                 830

Cys Ala Thr Ser Pro Cys Lys Asn Ser Gly Val Cys Lys Glu Ser Glu
            835                 840                 845

Asp Tyr Glu Ser Phe Ser Cys Val Cys Pro Thr Gly Trp Gln Gly Gln
    850                 855                 860

Thr Cys Glu Ile Asp Ile Asn Glu Cys Val Lys Ser Pro Cys Arg His
865                 870                 875                 880

Gly Ala Ser Cys Gln Asn Thr Asn Gly Ser Tyr Arg Cys Leu Cys Gln
                    885                 890                 895

Ala Gly Tyr Thr Gly Arg Asn Cys Glu Ser Asp Ile Asp Asp Cys Arg
                900                 905                 910

Pro Asn Pro Cys His Asn Gly Gly Ser Cys Thr Asp Gly Val Asn Ala
            915                 920                 925

Ala Phe Cys Asp Cys Leu Pro Gly Phe Gln Gly Ala Phe Cys Glu Glu
    930                 935                 940
```

-continued

```
Asp Ile Asn Glu Cys Ala Thr Asn Pro Cys Gln Asn Gly Ala Asn Cys
945                 950                 955                 960

Thr Asp Cys Val Asp Ser Tyr Thr Cys Thr Cys Pro Thr Gly Phe Asn
                965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
        995                 1000                1005

Cys Pro Pro Gly Phe Thr Gly Ser Tyr Cys Gln Tyr Asp Val Asn
    1010                1015                1020

Glu Cys Asp Ser Arg Pro Cys Leu His Gly Thr Cys Gln Asp
    1025                1030                1035

Ser Tyr Gly Thr Tyr Lys Cys Thr Cys Pro Gln Gly Tyr Thr Gly
    1040                1045                1050

Leu Asn Cys Gln Asn Leu Val Arg Trp Cys Asp Ser Ala Pro Cys
    1055                1060                1065

Lys Asn Gly Gly Lys Cys Trp Gln Thr Asn Thr Gln Tyr His Cys
    1070                1075                1080

Glu Cys Arg Ser Gly Trp Thr Gly Phe Asn Cys Asp Val Leu Ser
    1085                1090                1095

Val Ser Cys Glu Val Ala Ala Gln Lys Arg Gly Ile Asp Val Thr
    1100                1105                1110

Leu Leu Cys Gln His Gly Gly Leu Cys Val Asp Glu Glu Asp Lys
    1115                1120                1125

His Tyr Cys His Cys Gln Ala Gly Tyr Thr Gly Ser Tyr Cys Glu
    1130                1135                1140

Asp Glu Val Asp Glu Cys Ser Pro Asn Pro Cys Gln Asn Gly Ala
    1145                1150                1155

Thr Cys Thr Asp Tyr Leu Gly Gly Phe Ser Cys Lys Cys Val Ala
    1160                1165                1170

Gly Tyr His Gly Ser Asn Cys Ser Glu Glu Ile Asn Glu Cys Leu
    1175                1180                1185

Ser Gln Pro Cys Gln Asn Gly Gly Thr Cys Ile Asp Leu Thr Asn
    1190                1195                1200

Thr Tyr Lys Cys Ser Cys Pro Arg Gly Thr Gln Gly Val His Cys
    1205                1210                1215

Glu Ile Asn Val Asp Asp Cys His Pro Pro Leu Asp Pro Ala Ser
    1220                1225                1230

Arg Ser Pro Lys Cys Phe Asn Asn Gly Thr Cys Val Asp Gln Val
    1235                1240                1245

Gly Gly Tyr Thr Cys Thr Cys Pro Pro Gly Phe Val Gly Glu Arg
    1250                1255                1260

Cys Glu Gly Asp Val Asn Glu Cys Leu Ser Asn Pro Cys Asp Pro
    1265                1270                1275

Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
    1295                1300                1305

Asn Gly Cys Arg Gly Lys Pro Cys Arg Asn Gly Gly Val Cys Ala
    1310                1315                1320

Val Ala Ser Asn Thr Ala Arg Gly Phe Ile Cys Arg Cys Pro Ala
    1325                1330                1335
```

-continued

```
Arg Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Ser Phe Thr Gly Pro Glu Cys
    1370                1375                1380

Gln Phe Pro Ala Ser Ser Pro Cys Val Gly Ser Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Thr
    1430

<210> SEQ ID NO 2
<211> LENGTH: 5
<212> TYPE: PRT
<213> ORGANISM: Rattus norvegius

<400> SEQUENCE: 2

Asp Leu Gly Pro Gly
1               5

<210> SEQ ID NO 3
<211> LENGTH: 1419
<212> TYPE: PRT
<213> ORGANISM: Rattus norvegius

<400> SEQUENCE: 3

Met Pro Ala Leu Arg Pro Ala Ala Leu Arg Ala Leu Leu Trp Leu Trp
1               5                   10                  15

Leu Cys Gly Ala Gly Pro Ala His Ala Leu Gln Cys Arg Gly Gly Gln
                20                  25                  30

Glu Pro Cys Val Asn Glu Gly Thr Cys Val Thr Tyr His Asn Gly Thr
            35                  40                  45

Gly Tyr Cys Arg Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Thr Gln Ala Met Leu Gly Lys Ala Thr Cys Arg Cys Ala Pro Gly Phe
                85                  90                  95

Thr Gly Glu Asp Cys Gln Tyr Ser Thr Ser His Pro Cys Phe Val Ser
            100                 105                 110

Arg Pro Cys Gln Asn Gly Gly Thr Cys His Met Leu Ser Trp Asp Thr
        115                 120                 125

Tyr Glu Cys Thr Cys Gln Val Gly Phe Thr Gly Lys Gln Cys Gln Trp
    130                 135                 140

Thr Asp Val Cys Leu Ser His Pro Cys Glu Asn Gly Ser Thr Cys Ser
145                 150                 155                 160

Ser Val Ala Asn Gln Phe Ser Cys Arg Cys Pro Ala Gly Ile Thr Gly
                165                 170                 175

Gln Lys Cys Asp Ala Asp Ile Asn Glu Cys Asp Ile Pro Gly Arg Cys
            180                 185                 190

Gln His Gly Gly Thr Cys Leu Asn Leu Pro Gly Ser Tyr Arg Cys Gln
        195                 200                 205
```

-continued

```
Cys Pro Gln Arg Phe Thr Gly Gln His Cys Asp Ser Pro Tyr Val Pro
210                 215                 220
Cys Ala Pro Ser Pro Cys Val Asn Gly Gly Thr Cys Arg Gln Thr Gly
225                 230                 235                 240
Asp Phe Thr Ser Glu Cys His Cys Leu Pro Gly Phe Glu Gly Ser Asn
                245                 250                 255
Cys Glu Arg Asn Ile Asp Asp Cys Pro Asn His Lys Cys Gln Asn Gly
            260                 265                 270
Gly Val Cys Val Asp Gly Val Asn Thr Tyr Asn Cys Arg Cys Pro Pro
        275                 280                 285
Gln Trp Thr Gly Gln Phe Cys Thr Glu Asp Val Asp Glu Cys Leu Leu
290                 295                 300
Gln Pro Asn Ala Cys Gln Asn Gly Gly Thr Cys Thr Asn Arg Asn Gly
305                 310                 315                 320
Gly Tyr Gly Cys Val Cys Val Asn Gly Trp Ser Gly Asp Asp Cys Ser
                325                 330                 335
Glu Asn Ile Asp Asp Cys Ala Phe Ala Ser Cys Thr Pro Gly Ser Thr
            340                 345                 350
Cys Ile Asp Arg Val Ala Ser Phe Ser Cys Leu Cys Pro Glu Gly Lys
        355                 360                 365
Ala Gly Leu Leu Cys His Leu Asp Asp Ala Cys Ile Ser Asn Pro Cys
370                 375                 380
His Lys Gly Ala Leu Cys Asp Thr Asn Pro Leu Asn Gly Gln Tyr Ile
385                 390                 395                 400
Cys Thr Cys Pro Gln Ala Tyr Lys Gly Ala Asp Cys Thr Glu Asp Val
                405                 410                 415
Asp Glu Cys Ala Met Ala Asn Ser Asn Pro Cys Glu His Ala Gly Lys
            420                 425                 430
Cys Val Asn Thr Asp Gly Ala Phe His Cys Glu Cys Leu Lys Gly Tyr
        435                 440                 445
Ala Gly Pro Arg Cys Glu Met Asp Ile Asn Glu Cys His Ser Asp Pro
450                 455                 460
Cys Gln Asn Asp Ala Thr Cys Leu Asp Lys Ile Gly Gly Phe Thr Cys
465                 470                 475                 480
Leu Cys Met Pro Gly Phe Lys Gly Val His Cys Glu Leu Glu Val Asn
                485                 490                 495
Glu Cys Gln Ser Asn Pro Cys Val Asn Asn Gly Gln Cys Val Asp Lys
            500                 505                 510
Val Asn Arg Phe Gln Cys Leu Cys Pro Pro Gly Phe Thr Gly Pro Val
        515                 520                 525
Cys Gln Ile Asp Ile Asp Asp Cys Ser Ser Thr Pro Cys Leu Asn Gly
530                 535                 540
Ala Lys Cys Ile Asp His Pro Asn Gly Tyr Glu Cys Gln Cys Ala Thr
545                 550                 555                 560
Gly Phe Thr Gly Thr Leu Cys Asp Glu Asn Ile Asp Asn Cys Asp Pro
                565                 570                 575
Asp Pro Cys His His Gly Gln Cys Gln Asp Gly Ile Asp Ser Tyr Thr
            580                 585                 590
Cys Ile Cys Asn Pro Gly Tyr Met Gly Ala Ile Cys Ser Asp Gln Ile
        595                 600                 605
Asp Glu Cys Tyr Ser Ser Pro Cys Leu Asn Asp Gly Arg Cys Ile Asp
610                 615                 620
Leu Val Asn Gly Tyr Gln Cys Asn Cys Gln Pro Gly Thr Ser Gly Leu
```

```
                625               630               635               640
      Asn Cys Glu Ile Asn Phe Asp Asp Cys Ala Ser Asn Pro Cys Leu His
                          645                 650                 655
      Gly Ala Cys Val Asp Gly Ile Asn Arg Tyr Ser Cys Val Cys Ser Pro
                          660                 665                 670
      Gly Phe Thr Gly Gln Arg Cys Asn Ile Asp Ile Asp Glu Cys Ala Ser
                          675                 680                 685
      Asn Pro Cys Arg Lys Asp Ala Thr Cys Ile Asn Asp Val Asn Gly Phe
                          690                 695                 700
      Arg Cys Met Cys Pro Glu Gly His His Pro Ser Cys Tyr Ser Gln
      705                 710                 715                 720
      Val Asn Glu Cys Leu Ser Ser Pro Cys Ile His Gly Asn Cys Thr Gly
                          725                 730                 735
      Gly Leu Ser Gly Tyr Lys Cys Leu Cys Asp Ala Gly Trp Val Gly Ile
                          740                 745                 750
      Asn Cys Glu Val Asp Lys Asn Glu Cys Leu Ser Asn Pro Cys Gln Asn
                          755                 760                 765
      Gly Gly Thr Cys Asn Asn Leu Val Asn Gly Tyr Arg Cys Thr Cys Lys
                          770                 775                 780
      Lys Gly Phe Lys Gly Tyr Asn Cys Gln Val Asn Ile Asp Glu Cys Ala
      785                 790                 795                 800
      Ser Asn Pro Cys Leu Asn Gln Gly Thr Cys Leu Asp Asp Val Ser Gly
                          805                 810                 815
      Tyr Thr Cys His Cys Met Leu Pro Tyr Thr Gly Lys Asn Cys Gln Thr
                          820                 825                 830
      Val Leu Ala Pro Cys Ser Pro Asn Pro Cys Glu Asn Ala Ala Val Cys
                          835                 840                 845
      Lys Glu Ala Pro Asn Phe Glu Ser Phe Thr Cys Leu Cys Ala Pro Gly
                          850                 855                 860
      Trp Gln Gly Gln Arg Cys Thr Val Asp Val Asp Glu Cys Val Ser Lys
      865                 870                 875                 880
      Pro Cys Met Asn Asn Gly Ile Cys His Asn Thr Gln Gly Ser Tyr Met
                          885                 890                 895
      Cys Glu Cys Pro Pro Gly Phe Ser Gly Met Asp Cys Glu Glu Asp Ile
                          900                 905                 910
      Asn Asp Cys Leu Ala Asn Pro Cys Gln Asn Gly Gly Ser Cys Val Asp
                          915                 920                 925
      Lys Val Asn Thr Phe Ser Cys Leu Cys Leu Pro Gly Phe Val Gly Asp
                          930                 935                 940
      Lys Cys Gln Thr Asp Met Asn Glu Cys Leu Ser Glu Pro Cys Lys Asn
      945                 950                 955                 960
      Gly Gly Thr Cys Ser Asp Tyr Val Asn Ser Tyr Thr Cys Thr Cys Pro
                          965                 970                 975
      Ala Gly Phe His Gly Val His Cys Glu Asn Asn Ile Asp Glu Cys Thr
                          980                 985                 990
      Glu Ser Ser Cys Phe Asn Gly Gly Thr Cys Val Asp Gly Ile Asn Ser
                          995                1000                1005
      Phe Ser Cys Leu Cys Pro Val Gly Phe Thr Gly Pro Phe Cys Leu
                         1010                1015                1020
      His Asp Ile Asn Glu Cys Ser Ser Asn Pro Cys Leu Asn Ser Gly
                         1025                1030                1035
      Thr Cys Val Asp Gly Leu Gly Thr Tyr Arg Cys Thr Cys Pro Leu
                         1040                1045                1050
```

-continued

Gly Tyr Thr Gly Lys Asn Cys Gln Thr Leu Val Asn Leu Cys Ser
1055                1060                1065

Pro Ser Pro Cys Lys Asn Lys Gly Thr Cys Ala Gln Glu Lys Ala
1070                1075                1080

Arg Pro Arg Cys Leu Cys Pro Pro Gly Trp Asp Gly Ala Tyr Cys
1085                1090                1095

Asp Val Leu Asn Val Ser Cys Lys Ala Ala Leu Gln Lys Gly
1100                1105                1110

Val Pro Val Glu His Leu Cys Gln His Ser Gly Ile Cys Ile Asn
1115                1120                1125

Ala Gly Asn Thr His His Cys Gln Cys Pro Leu Gly Tyr Thr Gly
1130                1135                1140

Ser Tyr Cys Glu Glu Gln Leu Asp Glu Cys Ala Ser Asn Pro Cys
1145                1150                1155

Gln His Gly Ala Thr Cys Ser Asp Phe Ile Gly Gly Tyr Arg Cys
1160                1165                1170

Glu Cys Val Pro Gly Tyr Gln Gly Val Asn Cys Glu Tyr Glu Val
1175                1180                1185

Asp Glu Cys Gln Asn Gln Pro Cys Gln Asn Gly Gly Thr Cys Ile
1190                1195                1200

Asp Leu Val Asn His Phe Lys Cys Ser Cys Pro Pro Gly Thr Arg
1205                1210                1215

Gly Leu Leu Cys Glu Glu Asn Ile Asp Asp Cys Ala Gly Ala Pro
1220                1225                1230

His Cys Leu Asn Gly Gly Gln Cys Val Asp Arg Ile Gly Gly Tyr
1235                1240                1245

Ser Cys Arg Cys Leu Pro Gly Phe Ala Gly Glu Arg Cys Glu Gly
1250                1255                1260

Asp Ile Asn Glu Cys Leu Ser Asn Pro Cys Ser Ser Glu Gly Ser
1265                1270                1275

Leu Asp Cys Ile Gln Leu Lys Asn Asn Tyr Gln Cys Val Cys Arg
1280                1285                1290

Ser Ala Phe Thr Gly Arg His Cys Glu Thr Phe Leu Asp Val Cys
1295                1300                1305

Pro Gln Lys Pro Cys Leu Asn Gly Gly Thr Cys Ala Val Ala Ser
1310                1315                1320

Asn Val Pro Asp Gly Phe Ile Cys Arg Cys Pro Pro Gly Phe Ser
1325                1330                1335

Gly Ala Arg Cys Gln Ser Ser Cys Gly Gln Val Lys Cys Arg Arg
1340                1345                1350

Gly Glu Gln Cys Val His Thr Ala Ser Gly Pro His Cys Phe Cys
1355                1360                1365

Pro Asn His Lys Asp Cys Glu Ser Gly Cys Ala Ser Asn Pro Cys
1370                1375                1380

Gln His Gly Gly Thr Cys Tyr Pro Gln Arg Gln Pro Pro Tyr Tyr
1385                1390                1395

Ser Cys Arg Cys Ser Pro Pro Phe Trp Gly Ser His Cys Glu Ser
1400                1405                1410

Tyr Thr Ala Pro Thr Ser
1415

<210> SEQ ID NO 4
<211> LENGTH: 1379

<212> TYPE: PRT
<213> ORGANISM: Mus musculus

<400> SEQUENCE: 4

```
Met Gly Leu Gly Ala Arg Gly Arg Arg Arg Arg Leu Met Ala
1               5                   10                  15

Leu Pro Pro Pro Pro Met Arg Ala Leu Pro Leu Leu Leu Leu
            20                  25                  30

Leu Ala Gly Leu Gly Ala Ala Pro Pro Cys Leu Asp Gly Ser Pro
        35                  40                  45

Cys Ala Asn Gly Gly Arg Cys Thr His Gln Pro Ser Leu Glu Ala
50                  55                  60

Ala Cys Leu Cys Leu Pro Gly Trp Val Gly Glu Arg Cys Gln Leu Glu
65                  70                  75                  80

Asp Pro Cys His Ser Gly Pro Cys Ala Gly Arg Gly Val Cys Gln Ser
                85                  90                  95

Ser Val Val Ala Gly Thr Ala Arg Phe Ser Cys Arg Cys Leu Arg Gly
            100                 105                 110

Phe Gln Gly Pro Asp Cys Ser Gln Pro Asp Pro Cys Val Ser Arg Pro
        115                 120                 125

Cys Val His Gly Ala Pro Cys Ser Val Gly Pro Asp Gly Arg Phe Ala
130                 135                 140

Cys Ala Cys Pro Pro Gly Tyr Gln Gly Gln Ser Cys Gln Ser Asp Ile
145                 150                 155                 160

Asp Glu Cys Arg Ser Gly Thr Thr Cys Arg His Gly Gly Thr Cys Leu
                165                 170                 175

Asn Thr Pro Gly Ser Phe Arg Cys Gln Cys Pro Leu Gly Tyr Thr Gly
            180                 185                 190

Leu Leu Cys Glu Asn Pro Val Val Pro Cys Ala Pro Ser Pro Cys Arg
        195                 200                 205

Asn Gly Gly Thr Cys Arg Gln Ser Ser Asp Val Thr Tyr Asp Cys Ala
210                 215                 220

Cys Leu Pro Gly Phe Glu Gly Gln Asn Cys Glu Val Asn Val Asp Asp
225                 230                 235                 240

Cys Pro Gly His Arg Cys Leu Asn Gly Gly Thr Cys Val Asp Gly Val
                245                 250                 255

Asn Thr Tyr Asn Cys Gln Cys Pro Pro Glu Trp Thr Gly Gln Phe Cys
            260                 265                 270

Thr Glu Asp Val Asp Glu Cys Gln Leu Gln Pro Asn Ala Cys His Asn
        275                 280                 285

Gly Gly Thr Cys Phe Asn Leu Leu Gly Gly His Ser Cys Val Cys Val
290                 295                 300

Asn Gly Trp Thr Gly Glu Ser Cys Ser Gln Asn Ile Asp Asp Cys Ala
305                 310                 315                 320

Thr Ala Val Cys Phe His Gly Ala Thr Cys His Asp Arg Val Ala Ser
                325                 330                 335

Phe Tyr Cys Ala Cys Pro Met Gly Lys Thr Gly Leu Leu Cys His Leu
            340                 345                 350

Asp Asp Ala Cys Val Ser Asn Pro Cys His Glu Asp Ala Ile Cys Asp
        355                 360                 365

Thr Asn Pro Val Ser Gly Arg Ala Ile Cys Thr Cys Pro Pro Gly Phe
370                 375                 380

Thr Gly Gly Ala Cys Asp Gln Asp Val Asp Glu Cys Ser Ile Gly Ala
385                 390                 395                 400
```

-continued

```
Asn Pro Cys Glu His Leu Gly Arg Cys Val Asn Thr Gln Gly Ser Phe
            405                 410                 415
Leu Cys Gln Cys Gly Arg Gly Tyr Thr Gly Pro Arg Cys Glu Thr Asp
        420                 425                 430
Val Asn Glu Cys Leu Ser Gly Pro Cys Arg Asn Gln Ala Thr Cys Leu
    435                 440                 445
Asp Arg Ile Gly Gln Phe Thr Cys Ile Cys Met Ala Gly Phe Thr Gly
450                 455                 460
Thr Tyr Cys Glu Val Asp Ile Asp Glu Cys Gln Ser Ser Pro Cys Val
465                 470                 475                 480
Asn Gly Gly Val Cys Lys Asp Arg Val Asn Gly Phe Ser Cys Thr Cys
                485                 490                 495
Pro Ser Gly Phe Ser Gly Ser Met Cys Gln Leu Asp Val Asp Glu Cys
            500                 505                 510
Ala Ser Thr Pro Cys Arg Asn Gly Ala Lys Cys Val Asp Gln Pro Asp
        515                 520                 525
Gly Tyr Glu Cys Arg Cys Ala Glu Gly Phe Glu Gly Thr Leu Cys Glu
    530                 535                 540
Arg Asn Val Asp Asp Cys Ser Pro Asp Pro Cys His His Gly Arg Cys
545                 550                 555                 560
Val Asp Gly Ile Ala Ser Phe Ser Cys Ala Cys Ala Pro Gly Tyr Thr
                565                 570                 575
Gly Ile Arg Cys Glu Ser Gln Val Asp Glu Cys Arg Ser Gln Pro Cys
            580                 585                 590
Arg Tyr Gly Gly Lys Cys Leu Asp Leu Val Asp Lys Tyr Leu Cys Arg
        595                 600                 605
Cys Pro Pro Gly Thr Thr Gly Val Asn Cys Glu Val Asn Ile Asp Asp
    610                 615                 620
Cys Ala Ser Asn Pro Cys Thr Phe Gly Val Cys Arg Asp Gly Ile Asn
625                 630                 635                 640
Arg Tyr Asp Cys Val Cys Gln Pro Gly Phe Thr Gly Pro Leu Cys Asn
                645                 650                 655
Val Glu Ile Asn Glu Cys Ala Ser Ser Pro Cys Gly Glu Gly Gly Ser
            660                 665                 670
Cys Val Asp Gly Glu Asn Gly Phe His Cys Leu Cys Pro Pro Gly Ser
        675                 680                 685
Leu Pro Pro Leu Cys Leu Pro Ala Asn His Pro Cys Ala His Lys Pro
    690                 695                 700
Cys Ser His Gly Val Cys His Asp Ala Pro Gly Gly Phe Arg Cys Val
705                 710                 715                 720
Cys Glu Pro Gly Trp Ser Gly Pro Arg Cys Ser Gln Ser Leu Ala Pro
                725                 730                 735
Asp Ala Cys Glu Ser Gln Pro Cys Gln Ala Gly Gly Thr Cys Thr Ser
            740                 745                 750
Asp Gly Ile Gly Phe Arg Cys Thr Cys Ala Pro Gly Phe Gln Gly His
        755                 760                 765
Gln Cys Glu Val Leu Ser Pro Cys Thr Pro Ser Leu Cys Glu His Gly
    770                 775                 780
Gly His Cys Glu Ser Asp Pro Asp Arg Leu Thr Val Cys Ser Cys Pro
785                 790                 795                 800
Pro Gly Trp Gln Gly Pro Arg Cys Gln Gln Asp Val Asp Glu Cys Ala
                805                 810                 815
```

-continued

```
Gly Ala Ser Pro Cys Gly Pro His Gly Thr Cys Thr Asn Leu Pro Gly
            820                 825                 830

Asn Phe Arg Cys Ile Cys His Arg Gly Tyr Thr Gly Pro Phe Cys Asp
            835                 840                 845

Gln Asp Ile Asp Asp Cys Asp Pro Asn Pro Cys Leu His Gly Gly Ser
        850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
            900                 905                 910

Cys Pro Pro Gly Tyr Gly Gly Phe His Cys Glu Ile Asp Leu Pro Asp
            915                 920                 925

Cys Ser Pro Ser Ser Cys Phe Asn Gly Gly Thr Cys Val Asp Gly Val
        930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
                965                 970                 975

Ile Cys Asn Pro Thr His Pro Gly Phe Glu Cys Thr Cys Arg Glu Gly
            980                 985                 990

Phe Thr Gly Ser Gln Cys Gln Asn Pro Val Asp Trp Cys Ser Gln Ala
        995                 1000                1005

Pro Cys  Gln Asn Gly Gly  Arg Cys Val Gln Thr  Gly Ala Tyr Cys
    1010                 1015                1020

Ile Cys  Pro Pro Gly Trp Ser  Gly Arg Leu Cys Asp  Ile Gln Ser
    1025                 1030                1035

Leu Pro  Cys Thr Glu Ala Ala  Ala Gln Met Gly Val  Arg Leu Glu
    1040                 1045                1050

Gln Leu  Cys Gln Glu Gly Gly  Lys Cys Ile Asp Lys  Gly Arg Ser
    1055                 1060                1065

His Tyr  Cys Val Cys Pro Glu  Gly Arg Thr Gly Ser  His Cys Glu
    1070                 1075                1080

His Glu  Val Asp Pro Cys Thr  Ala Gln Pro Cys Gln  His Gly Gly
    1085                 1090                1095

Thr Cys  Arg Gly Tyr Met Gly  Gly Tyr Val Cys Glu  Cys Pro Ala
    1100                 1105                1110

Gly Tyr  Ala Gly Asp Ser Cys  Glu Asp Asn Ile Asp  Glu Cys Ala
    1115                 1120                1125

Ser Gln  Pro Cys Gln Asn Gly  Gly Ser Cys Ile Asp  Leu Val Ala
    1130                 1135                1140

Arg Tyr  Leu Cys Ser Cys Pro  Pro Gly Thr Leu Gly  Val Leu Cys
    1145                 1150                1155

Glu Ile  Asn Glu Asp Asp Cys  Asp Leu Gly Pro Ser  Leu Asp Ser
    1160                 1165                1170

Gly Val  Gln Cys Leu His Asn  Gly Thr Cys Val Asp  Leu Val Gly
    1175                 1180                1185

Gly Phe  Arg Cys Asn Cys Pro  Pro Gly Tyr Thr Gly  Leu His Cys
    1190                 1195                1200

Glu Ala  Asp Ile Asn Glu Cys  Arg Pro Gly Ala Cys  His Ala Ala
    1205                 1210                1215

His Thr  Arg Asp Cys Leu Gln  Asp Pro Gly Gly His  Phe Arg Cys
```

-continued

```
                1220                1225                1230
Val Cys His Pro Gly Phe Thr Gly Pro Arg Cys Gln Ile Ala Leu
    1235                1240                1245

Ser Pro Cys Glu Ser Gln Pro Cys Gln His Gly Gln Cys Arg
    1250                1255                1260

His Ser Leu Gly Arg Gly Gly Leu Thr Phe Thr Cys His Cys
    1265                1270                1275

Val Pro Pro Phe Trp Gly Leu Arg Cys Glu Arg Val Ala Arg Ser
    1280                1285                1290

Cys Arg Glu Leu Gln Cys Pro Val Gly Ile Pro Cys Gln Gln Thr
    1295                1300                1305

Ala Arg Gly Pro Arg Cys Ala Cys Pro Pro Gly Leu Ser Gly Pro
    1310                1315                1320

Ser Cys Arg Val Ser Arg Ala Ser Pro Ser Gly Ala Thr Asn Ala
    1325                1330                1335

Ser Cys Ala Ser Ala Pro Cys Leu His Gly Gly Ser Cys Leu Pro
    1340                1345                1350

Val Gln Ser Val Pro Phe Phe Arg Cys Val Cys Ala Pro Gly Trp
    1355                1360                1365

Gly Gly Pro Arg Cys Glu Thr Pro Ser Ala Ala
    1370                1375

<210> SEQ ID NO 5
<211> LENGTH: 1170
<212> TYPE: PRT
<213> ORGANISM: Mus musculus

<400> SEQUENCE: 5

Met Gln Pro Gln Leu Leu Leu Leu Leu Pro Leu Asn Phe Pro
1               5                   10                  15

Val Ile Leu Thr Arg Glu Leu Leu Cys Gly Gly Ser Pro Glu Pro Cys
                20                  25                  30

Ala Asn Gly Gly Thr Cys Leu Arg Leu Ser Arg Gly Gln Gly Ile Cys
            35                  40                  45

Gln Cys Ala Pro Gly Phe Leu Gly Glu Thr Cys Gln Phe Pro Asp Pro
        50                  55                  60

Cys Arg Asp Thr Gln Leu Cys Lys Asn Gly Gly Ser Cys Gln Ala Leu
    65                  70                  75                  80

Leu Pro Thr Pro Pro Ser Ser Arg Ser Pro Thr Ser Pro Leu Thr Pro
                85                  90                  95

His Phe Ser Cys Thr Cys Pro Ser Gly Phe Thr Gly Asp Arg Cys Gln
            100                 105                 110

Thr His Leu Glu Glu Leu Cys Pro Ser Phe Cys Ser Asn Gly Gly
        115                 120                 125

His Cys Tyr Val Gln Ala Ser Gly Arg Pro Gln Cys Ser Cys Glu Pro
    130                 135                 140

Gly Trp Thr Gly Glu Gln Cys Gln Leu Arg Asp Phe Cys Ser Ala Asn
145                 150                 155                 160

Pro Cys Ala Asn Gly Gly Val Cys Leu Ala Thr Tyr Pro Gln Ile Gln
                165                 170                 175

Cys Arg Cys Pro Pro Gly Phe Glu Gly His Thr Cys Glu Arg Asp Ile
            180                 185                 190

Asn Glu Cys Phe Leu Glu Pro Gly Pro Cys Pro Gln Gly Thr Ser Cys
        195                 200                 205
```

-continued

```
His Asn Thr Leu Gly Ser Tyr Gln Cys Leu Cys Pro Val Gly Gln Glu
            210                 215                 220

Gly Pro Gln Cys Lys Leu Arg Lys Gly Ala Cys Pro Pro Gly Ser Cys
225                 230                 235                 240

Leu Asn Gly Gly Thr Cys Gln Leu Val Pro Glu Gly His Ser Thr Phe
                245                 250                 255

His Leu Cys Leu Cys Pro Pro Gly Phe Thr Gly Leu Asp Cys Glu Met
            260                 265                 270

Asn Pro Asp Asp Cys Val Arg His Gln Cys Gln Asn Gly Ala Thr Cys
            275                 280                 285

Leu Asp Gly Leu Asp Thr Tyr Thr Cys Leu Cys Pro Lys Thr Trp Lys
    290                 295                 300

Gly Trp Asp Cys Ser Glu Asp Ile Asp Glu Cys Glu Ala Arg Gly Pro
305                 310                 315                 320

Pro Arg Cys Arg Asn Gly Gly Thr Cys Gln Asn Thr Ala Gly Ser Phe
                325                 330                 335

His Cys Val Cys Val Ser Gly Trp Gly Gly Ala Gly Cys Glu Glu Asn
            340                 345                 350

Leu Asp Asp Cys Ala Ala Ala Thr Cys Ala Pro Gly Ser Thr Cys Ile
    355                 360                 365

Asp Arg Val Gly Ser Phe Ser Cys Leu Cys Pro Pro Gly Arg Thr Gly
    370                 375                 380

Leu Leu Cys His Leu Glu Asp Met Cys Leu Ser Gln Pro Cys His Val
385                 390                 395                 400

Asn Ala Gln Cys Ser Thr Asn Pro Leu Thr Gly Ser Thr Leu Cys Ile
                405                 410                 415

Cys Gln Pro Gly Tyr Ser Gly Ser Thr Cys His Gln Asp Leu Asp Glu
                420                 425                 430

Cys Gln Met Ala Gln Gln Gly Pro Ser Pro Cys Glu His Gly Gly Ser
            435                 440                 445

Cys Ile Asn Thr Pro Gly Ser Phe Asn Cys Leu Cys Leu Pro Gly Tyr
    450                 455                 460

Thr Gly Ser Arg Cys Glu Ala Asp His Asn Glu Cys Leu Ser Gln Pro
465                 470                 475                 480

Cys His Pro Gly Ser Thr Cys Leu Asp Leu Leu Ala Thr Phe His Cys
                485                 490                 495

Leu Cys Pro Pro Gly Leu Glu Gly Arg Leu Cys Glu Val Glu Val Asn
            500                 505                 510

Glu Cys Thr Ser Asn Pro Cys Leu Asn Gln Ala Ala Cys His Asp Leu
            515                 520                 525

Leu Asn Gly Phe Gln Cys Leu Cys Leu Pro Gly Phe Thr Gly Ala Arg
    530                 535                 540

Cys Glu Lys Asp Met Asp Glu Cys Ser Ser Thr Pro Cys Ala Asn Gly
545                 550                 555                 560

Gly Arg Cys Arg Asp Gln Pro Gly Ala Phe Tyr Cys Glu Cys Leu Pro
                565                 570                 575

Gly Phe Glu Gly Pro His Cys Glu Lys Glu Val Asp Glu Cys Leu Ser
            580                 585                 590

Asp Pro Cys Pro Val Gly Ala Ser Cys Leu Asp Leu Pro Gly Ala Phe
    595                 600                 605

Phe Cys Leu Cys Arg Pro Gly Phe Thr Gly Gln Leu Cys Glu Val Pro
610                 615                 620

Leu Cys Thr Pro Asn Met Cys Gln Pro Gly Gln Gln Cys Gln Gly Gln
```

-continued

```
            625                 630                 635                 640
Glu His Arg Ala Pro Cys Leu Cys Pro Asp Gly Ser Pro Gly Cys Val
                    645                 650                 655
Pro Ala Glu Asp Asn Cys Pro Cys His His Gly His Cys Gln Arg Ser
                    660                 665                 670
Leu Cys Val Cys Asp Glu Gly Trp Thr Gly Pro Glu Cys Glu Thr Glu
                    675                 680                 685
Leu Gly Gly Cys Ile Ser Thr Pro Cys Ala His Gly Gly Thr Cys His
            690                 695                 700
Pro Gln Pro Ser Gly Tyr Asn Cys Thr Cys Pro Ala Gly Tyr Met Gly
705                 710                 715                 720
Leu Thr Cys Ser Glu Glu Val Thr Ala Cys His Ser Gly Pro Cys Leu
                    725                 730                 735
Asn Gly Gly Ser Cys Ser Ile Arg Pro Glu Gly Tyr Ser Cys Thr Cys
                    740                 745                 750
Leu Pro Ser His Thr Gly Arg His Cys Gln Thr Ala Val Asp His Cys
                    755                 760                 765
Val Ser Ala Ser Cys Leu Asn Gly Gly Thr Cys Val Asn Lys Pro Gly
            770                 775                 780
Thr Phe Phe Cys Leu Cys Ala Thr Gly Phe Gln Gly Leu His Cys Glu
785                 790                 795                 800
Glu Lys Thr Asn Pro Ser Cys Ala Asp Ser Pro Cys Arg Asn Lys Ala
                    805                 810                 815
Thr Cys Gln Asp Thr Pro Arg Gly Ala Arg Cys Leu Cys Ser Pro Gly
                    820                 825                 830
Tyr Thr Gly Ser Ser Cys Gln Thr Leu Ile Asp Leu Cys Ala Arg Lys
                    835                 840                 845
Pro Cys Pro His Thr Ala Arg Cys Leu Gln Ser Gly Pro Ser Phe Gln
            850                 855                 860
Cys Leu Cys Leu Gln Gly Trp Thr Gly Ala Leu Cys Asp Phe Pro Leu
865                 870                 875                 880
Ser Cys Gln Lys Ala Ala Met Ser Gln Gly Ile Glu Ile Ser Gly Leu
                    885                 890                 895
Cys Gln Asn Gly Gly Leu Cys Ile Asp Thr Gly Ser Ser Tyr Phe Cys
                    900                 905                 910
Arg Cys Pro Pro Gly Phe Gln Gly Lys Leu Cys Gln Asp Asn Val Asn
                    915                 920                 925
Pro Cys Glu Pro Asn Pro Cys His His Gly Ser Thr Cys Val Pro Gln
            930                 935                 940
Pro Ser Gly Tyr Val Cys Gln Cys Ala Pro Gly Tyr Glu Gly Gln Asn
945                 950                 955                 960
Cys Ser Lys Val Leu Asp Ala Cys Gln Ser Gln Pro Cys His Asn His
                    965                 970                 975
Gly Thr Cys Thr Ser Arg Pro Gly Gly Phe His Cys Ala Cys Pro Pro
                    980                 985                 990
Gly Phe Val Gly Leu Arg Cys Glu  Gly Asp Val Asp Glu  Cys Leu Asp
                    995                 1000                1005
Arg Pro Cys His Pro Ser Gly  Thr Ala Ala Cys His  Ser Leu Ala
            1010                1015                1020
Asn Ala  Phe Tyr Cys Gln Cys  Leu Pro Gly His Thr  Gly Gln Arg
            1025                1030                1035
Cys Glu  Val Glu Met Asp Leu  Cys Gln Ser Gln Pro  Cys Ser Asn
            1040                1045                1050
```

-continued

```
Gly Gly Ser Cys Glu Ile Thr Thr Gly Pro Pro Gly Phe Thr
    1055                1060                1065

Cys His Cys Pro Lys Gly Phe Glu Gly Pro Thr Cys Ser His Lys
    1070                1075                1080

Ala Leu Ser Cys Gly Ile His His Cys His Asn Gly Gly Leu Cys
    1085                1090                1095

Leu Pro Ser Pro Lys Pro Gly Ser Pro Pro Leu Cys Ala Cys Leu
    1100                1105                1110

Ser Gly Phe Gly Gly Pro Asp Cys Leu Thr Pro Ala Pro Pro
    1115                1120                1125

Gly Cys Gly Pro Pro Ser Pro Cys Leu His Asn Gly Thr Cys Thr
    1130                1135                1140

Glu Thr Pro Gly Leu Gly Asn Pro Gly Phe Gln Cys Thr Cys Pro
    1145                1150                1155

Pro Asp Ser Pro Gly Pro Arg Cys Gln Arg Pro Gly
    1160                1165            1170
```

<210> SEQ ID NO 6
<211> LENGTH: 4293
<212> TYPE: DNA
<213> ORGANISM: Rattus norvegius

<400> SEQUENCE: 6

| | |
|---|---|
| atgacaggct tccagggctg ccaggccctg ctgcatctgg ccaaggccgt ggttcgcttg | 60 |
| agatgctccc agccaagtgg gacctgcctg aatggaggga ggtgcgaagt ggccaacggc | 120 |
| actgaagcct gtgtctgcag cggagcgttc gtgggccagc gatgccagga ccccagccct | 180 |
| tgcctcagca caccatgtaa gaatgctgga acgtgctatg ttgtggacca tggcggcatc | 240 |
| gtggactatg cctgcagttg ccccctgggt ttctctgggc ccctctgcct gacacctctg | 300 |
| gccaatgcct gcctggccaa ccctgccgc aacgggggga cctgtgacct gctcactctc | 360 |
| acagaataca gtgccggtg cccgccaggg tggtcaggaa agtcatgtca gcaagccgac | 420 |
| ccctgtgcct ccaaccctg tgccaatggt ggccagtgcc tgccctttga gtcttcatac | 480 |
| atctgtggct gcccgccgg cttccatggc cccacctgca gacaagatgt taacgagtgc | 540 |
| agccagaacc ctgggttgtg ccgtcatggc ggcacgtgcc acaatgagat tggctcctat | 600 |
| cgctgtgcct gccgtgccac ccacactggt ccccactgcg agctgcccta cgtgccctgc | 660 |
| agcccctcac cctgccagaa cggaggcacc tgccgcccta cggggacac cacccacgag | 720 |
| tgtgcctgcc tgccaggctt gctggacag aactgtgaag aaaatgtgga tgactgccca | 780 |
| ggaaacaact gcaagaacgg gggtgcctgt gtggacggtg tgaataccta caattgccgc | 840 |
| tgcccaccgg agtggacagg tcagtactgc acagaggatg tggacgagtg tcagctcatg | 900 |
| cccaacgcct gccagaatgg cggaacctgc acaactccc acggtggcta caactgcgtg | 960 |
| tgtgtcaatg gctggactgg tgaggactgc agtgagaaca ttgatgactg tccagtgcc | 1020 |
| gcctgttttc agggtgccac ctgccatgac cgtgtggctt ccttctactg cgagtgtcca | 1080 |
| catgggcgca caggcctgct gtgccacctg aacgatgcgt gtatcagcaa ccctgcaac | 1140 |
| gagggctcca actgcgacac caaccctgtc aacggcaagg ccatctgcac ttgcccctcg | 1200 |
| gggtacacgg ggcagcctg cagccaggac gtggatgagt gcgctctagg tgccaacccg | 1260 |
| tgtgagcacg cggcaagtg cctcaacaca ctgggctctt tcgagtgtca gtgtctacag | 1320 |
| ggctacactg gccccgctg tgagattgat gtcaacgagt gcatctccaa cccatgtcag | 1380 |

-continued

```
aatgatgcca cgtgcctgga ccagattggg gagtttcagt gtatatgtat gccaggttat    1440
gagggtgtat actgtgagat caacacggac gagtgtgcca gcagccctg  tctacacaat    1500 ggccgctgcg tggacaagat caacgagttc ctgtgtcagt gtcccaaagg cttcagcggg    1560
cacctgtgcc agtatgacgt ggatgagtgc gccagcacac catgcaagaa cggcgccaag    1620
tgcctggatg ggcccaacac ctacacctgc gtgtgcacag aaggttacac ggggacccac    1680
tgcgaggtgg acattgacga gtgtgaccct gacccctgtc actatggttt gtgcaaggat    1740
ggtgtggcca cctttacctg cctctgccag ccaggctaca caggccatca ctgtgagacc    1800
aacattaatg agtgtcacag ccagccgtgc cgccatggcg gcacctgcca ggaccgtgac    1860
aactactacc tctgcttatg cctcaagggg accacaggac ccaactgtga gatcaatctg    1920
gatgactgtg cgagcaaccc ctgtgactct ggcacgtgtc tggacaagat cgatggctac    1980
gagtgtgcgt gcgagccagg ctacacaggg agcatgtgta atgtcaacat tgacgaatgt    2040
gcgggcagcc cctgccacaa cggggggcacc tgtgaggatg gcatcgccgg cttcacttgc    2100
cgctgccccg agggctacca cgaccctacg tgcctgtctg aggtcaacga gtgcaacagt    2160
aacccctgca tccatggagc ttgccgggat ggcctcaatg gatacaaatg tgactgtgcc    2220
cctgggtgga gtgggacaaa ctgtgacatc aacaacaatg agtgtgagtc caaccccttgt    2280 gtcaacggtg gcacctgcaa agacatgacc agtggctacg tatgcacctg ccgagaaggc    2340
ttcagtggcc ctaactgcca gaccaacatt aacgaatgtg cttccaaccc ctgcctgaac    2400
cagggcacct gcattgatga tgtcgctggg tacaaatgca actgccctct gccctataca    2460
ggagccacat gtgaggtggt gttggcccca tgtgccacca gcccctgcaa aaacagtggg    2520
gtatgcaagg agtctgagga ctatgagagc ttttcctgtg tctgtcccac aggctggcaa    2580
ggtcaaacct gcgagatcga catcaatgag tgtgtgaaaa gcccgtgtcg ccatggtgcc    2640
tcttgccaga acaccaatgg cagctaccgc tgcctctgcc aggctggcta cacgggtcgc    2700
aactgcgaga gtgacatcga tgactgccga cccaacccat gtcacaacgg gggttcctgc    2760
actgacgggg tcaacgcggc cttctgcgac tgcctgcccg gcttccaggg tgccttctgt    2820
gaggaggaca tcaacgaatg cgccagcaat ccatgccaaa atggcgccaa ctgcactgac    2880
tgcgtggaca gctacgtg   cacctgcccc acgggcttca atggcatcca ttgcgagaac    2940
aacacacctg actgtaccga gagctcctgt ttcaatggtg gcacctgtgt ggatggtatc    3000
aactccttca cctgtctgtg cccacctggc ttcacgggca gctactgcca gtatgacgtc    3060
aatgagtgtg actcacggcc ctgtctgcat ggtggcacct gccaagacag ctatggtacc    3120
tataagtgta cctgcccaca gggctacact ggtctcaact gccagaacct tgtgcgctgg    3180
tgtgactcag ctccctgcaa gaatggcggc aagtgctggc agaccaacac acagtaccac    3240
tgcgagtgcc gcagcggctg gactggcttc aactgcgacg tgctcagtgt gtcctgcgag    3300
gtggctgcac agaagcgagg catcgatgtc actctcctat gccagcacgg agggctctgt    3360
gtggatgagg aagacaagca ttactgccac tgccaggcag gatacacggg cagctactgt    3420
gaggacgagg tggacgagtg ctcacctaat ccctgccaga acgagccac  ctgcactgac    3480 tatctcggtg gcttttcctg caagtgtgtg gctgggtacc atggctctaa ctgctctgag    3540
gagatcaacg agtgcctatc ccaaccctgc cagaatgggg gtacctgcat tgatctgacc    3600
aacacctaca gtgctcctg  ccccagggcc acacagggtg tacactgtga gatcaacgtc    3660
gatgactgcc atcctcccct agaccctgct tcccgaagcc ccaaatgctt caataatggc    3720
acctgcgtgg accaggtggg tggctatacc tgcacctgcc cgccaggctt cgtcggggag    3780
```

| | |
|---|---|
| cggtgcgagg gcgatgtcaa tgagtgtctc tccaacccct gtgacccacg tggcacccag | 3840 |
| aactgcgtgc agcgtgttaa tgacttccac tgcgagtgcc gggctggcca cactggacgc | 3900 |
| cgctgtgagt cggtcattaa tggctgcagg ggcaaaccat gcaggaatgg aggtgtctgt | 3960 |
| gctgtggcct ccaacaccgc ccgtggattc atctgtaggt gccctgcggg cttcgagggt | 4020 |
| gccacttgtg aaaatgacgc ccgcacttgt ggcagtttgc gctgcctcaa cggtggtacg | 4080 |
| tgcatctcag gcccacgcag tcccacctgc ctatgcctgg gctccttcac tggccctgaa | 4140 |
| tgccagttcc cagccagcag cccctgtgtg ggtagcaacc cctgctacaa tcagggcacc | 4200 |
| tgtgagccca catccgagag ccctttctac cgctgtctat gccctgccaa attcaacggg | 4260 |
| ctgctgtgcc acatcctgga ctacagcttc aca | 4293 |

<210> SEQ ID NO 7
<211> LENGTH: 4257
<212> TYPE: DNA
<213> ORGANISM: Rattus norvegius

<400> SEQUENCE: 7

| | |
|---|---|
| atgcccgctc tgcgtcccgc cgcgctgcgg gcgctgctgt ggctctggct gtgcggcgcg | 60 |
| ggccccgcgc acgctttgca gtgtcgaggt ggtcaagagc cctgtgtaaa tgagggggacc | 120 |
| tgtgttacct accacaacgg cacaggctac tgccgatgtc cagagggctt cttgggagaa | 180 |
| tattgtcaac atcgagaccc ttgtgagaag aaccgctgtc agaatggtgg tacttgtgtg | 240 |
| acgcaggcca tgttgggaaa agccacctgt cgatgtgctc caggggttcac aggggaggac | 300 |
| tgccaatact cgacctctca cccctgtttt gtttcccgcc cctgtcagaa tggaggtacc | 360 |
| tgccacatgc tcagctggga cacctatgag tgcacctgtc aagttggctt cacaggaaag | 420 |
| cagtgtcagt ggacagatgt ctgtctgtct catccctgtg aaaatggaag cacctgtagc | 480 |
| tctgtggcca accagttctc ctgcagatgt cctgcaggca tcacaggcca gaagtgtgac | 540 |
| gccgacatca atgaatgtga cattccagga cgctgccaac atggtggcac ctgcctcaac | 600 |
| cttcctgggt cctaccgatg ccaatgccct cagcggttca caggccagca ctgtgacagc | 660 |
| ccttacgtgc cctgtgcacc ctcaccctgc gtcaatggag gcacctgccg tcagactgga | 720 |
| gacttcactt ctgaatgcca ttgcctgcca ggctttgaag ggagcaactg cgagcggaat | 780 |
| atcgacgact gccctaacca caagtgtcag aatggagggg tgtgtgtgga tggcgtcaat | 840 |
| acttacaact gccgctgccc ccctcagtgg actgggcagt ctgcacagga agacgtggat | 900 |
| gagtgtctgc tgcagcccaa tgcttgtcag aatggaggca cttgcaccaa ccgcaacgga | 960 |
| ggctacggct gcgtgtgcgt gaacggctgg agtggggatg actgcagcga gaacatcgat | 1020 |
| gactgtgcct tcgcttcctg cacgccaggc tccacctgta ttgaccgtgt ggcctccttc | 1080 |
| tcctgccttt gtccagaggg aaaggcaggg ctcctgtgtc atctggatga tgcctgtatc | 1140 |
| agcaacccctt gtcacaaggg ggcgctgtgt gataccaacc cctgaatgg gcagtacatt | 1200 |
| tgcacctgcc cacaggcgta caagggcgct gactgcacag aagacgtgga tgagtgtgct | 1260 |
| atggccaaca gtaacccttg tgagcatgca ggaaagtgtg tgaatacaga tggcgccttc | 1320 |
| cactgcgagt gtctgaaggg ctacgcaggg cctcgctgtg agatggacat caacgagtgt | 1380 |
| cactcagacc cctgtcagaa cgacgccacc tgcctggata gattggagg cttcacctgt | 1440 |
| ctctgcatgc cggggtttcaa aggtgtgcat tgtgaactgg aggtgaatga atgccagagc | 1500 |
| aacccgtgtg taaacaatgg gcagtgtgtg gacaaagtca atcgcttcca gtgtctgtgt | 1560 |

```
cccccctggtt tcacaggacc agtgtgccag atcgacattg acgactgctc cagtactccc    1620
tgcctgaatg gggccaagtg catcgatcac ccgaatggct atgaatgcca gtgtgccaca    1680
ggattcactg gcacactgtg tgatgagaac atcgacaact gtgacccgga tccttgccac    1740
catggccagt gccaggatgg gattgactcc tacacctgca tctgcaaccc cgggtacatg    1800
ggagccatct gtagtgacca gattgatgaa tgctacagca gccctgcct gaatgatgga    1860 cgctgcatcg acctggtgaa cggctaccag tgcaactgcc aaccgggtac ctcaggcctt    1920
aattgtgaaa ttaattttga tgactgtgcc agcaacccett gtctgcacgg agcctgtgtg    1980
gacggcatca accgttacag ttgtgtgtgc tctccgggat tcacagggca gaggtgcaac    2040
atagacattg atgagtgtgc ctccaacccc tgtcgcaagg atgcgacgtg catcaatgac    2100
gtgaatggtt tccggtgtat gtgccctgag gaccacacc atcccagctg ctactcacag    2160
gtgaacgagt gtttgagcag tccctgcatc catggaaact gtactggagg tctcagtggc    2220
tataagtgcc tctgcgatgc aggctgggtt ggtatcaact gcgaagtgga caaaaatgag    2280
tgtctttcta acccgtgcca gaatggaggg acatgtaata acctggtgaa tggctacagg    2340
tgtacatgca agaagggggtt caaaggctat aactgccagg tgaacataga tgagtgtgcc    2400
tcgaacccgt gtctgaacca agggacctgc ctcgatgacg tcagtggcta cacctgccac    2460
tgcatgctgc cttacacagg caagaattgt caaacggtgt tggcgccctg ctccctaac    2520 ccgtgtgaga acgctgcagt ttgtaaagag gcacccaact ttgagagctt cacctgcctg    2580
tgtgcccctg gctggcaagg tcagcgctgt acagttgacg ttgatgagtg tgtctccaag    2640
ccgtgtatga acaatggcat ctgccataat actcagggca gctacatgtg cgagtgccct    2700
cccggcttca gtggtatgga ctgtgaggag acatcaatg actgccttgc caacccctgc    2760
cagaacggag gctcctgtgt ggacaaagtg aacaccttct cctgcctgtg ccttcctggc    2820
ttcgtagggg acaagtgcca aacagacatg aatgaatgtc tgagcgagcc ctgtaagaat    2880 gggggggacct gctctgacta cgtcaacagc tacacctgca cgtgccctgc gggcttccat    2940
ggagtccact gtgaaaacaa catcgatgag tgcactgaga gctcctgttt caatggcggc    3000
acgtgtgttg atgggatcaa ctcttttctct tgcttatgcc ctgtgggttt cactggtccc    3060
ttctgcctcc atgatatcaa tgagtgcagc tctaacccgt gcctgaattc gggaacgtgt    3120
gttgatggcc tgggtaccta ccgatgcacc tgtcccttgg gctacactgg gaaaaactgt    3180 cagacccctgg tgaacctctg cagcccctct ccatgtaaaa acaaaggaac ttgtgctcag    3240
gaaaaggcaa ggccacgctg cctgtgtccg cctggatggg atgcgcata ctgtgatgtg    3300 ctcaatgtgt cctgtaaggc ggcagccttg cagaaaggag tacctgttga acacttgtgc    3360
cagcactcgg gtatctgtat caatgctggc aacacgcatc actgccagtg cccccctgggc    3420 tacacgggga gctactgcga ggaacagctt gacgagtgtg cgtccaatcc atgccagcat    3480
ggtgccacct gcagtgactt catcggagga tacagatgtg agtgtgttcc agggtatcag    3540
ggtgtcaact gtgagtatga agtggacgag tgccagaacc agccctgtca gaacggaggc    3600
acctgcatcg acctcgtgaa ccatttcaag tgctcgtgcc caccaggcac ccggggcctg    3660
ctttgtgaag agaacattga tgactgtgct ggggccccccc actgccttaa tggtggccag    3720
tgtgtggacc ggattggagg ctacagttgt cgctgtttgc ctggctttgc tggggagcgg    3780 tgtgagggg acatcaatga atgcctgtcc aatccttgca gctcagaggg cagcctggac    3840
tgcattcagc tcaaaaataa ctaccagtgt gtctgccgca gcgccttcac aggccgacac    3900
tgcgaaacct tcctagatgt gtgtccccag aagccttgcc tgaatggagg gacttgtgct    3960
```

```
gtggctagca acgtgcctga tggcttcatt tgtcgttgtc ccccagggtt ctccggggca    4020
agatgccaga gcagctgtgg acaagtgaag tgcagaagag gggagcagtg tgtgcacacc    4080
gcctcgggac cccactgctt ctgcccgaac cacaaggact gcgagtcagg ttgcgctagt    4140 aaccctgcc agcacggagg cacctgctac cctcagcgcc agcctcctta ctactcttgc    4200
cgctgctccc caccgttctg gggcagccac tgcgagagct acacagcccc caccagc       4257

<210> SEQ ID NO 8
<211> LENGTH: 4137
<212> TYPE: DNA
<213> ORGANISM: Mus musculus

<400> SEQUENCE: 8
atggggctgg gggccgggg ccgccgccgc cgtcgtcgcc tgatggcctt gccaccgcca      60
ccaccgccca tgcgggcgct gccctgctg ctgctgctag cggggctggg ggctgcagca     120
cccccttgtc tggatggaag cccatgtgca aatggaggtc ggtgcaccca ccagcagccc    180
tccctggagg ctgcttgcct gtgcctgcca ggctgggtgg gtgagcggtg ccagctggaa    240 gaccccttgcc actcaggccc ttgtgctggc cgaggcgttt gccagagttc agtggtggcg    300
ggcaccgccc gattctcctg tcgttgtctc cgtggcttcc aaggcccaga ctgctcccag    360
ccagacccct gcgtcagcag gcctgtgtt catggtgccc cctgctcagt ggggccggat     420
ggccgatttg cctgtgcctg cccacctggc taccagggtc aaagctgcca aagtgacata    480
gatgagtgcc gatctggtac aacttgccgt catggtggta cctgtctcaa tacacctgga    540
tccttccgct gccagtgtcc tcttggttat acagggctgc tgtgtgagaa ccccgtagtg    600
ccctgtgccc cttccccgtg tcgtaatggt ggcacctgta gcagagcag tgatgtcaca     660 tatgactgtg cttgccttcc tggcttcgag ggccagaact gtgaagtcaa cgtggatgac    720
tgtcctggac atcggtgtct caatgggga acgtgtgtag acggtgtcaa tacttacaac    780
tgccagtgcc ctccggagtg gacaggccag ttctgtacag aagatgtgga tgagtgtcag    840
ctgcagccca tgcctgcca caatgggggt acctgcttca acctactggg tggccacagc    900
tgtgtatgtg tcaatggctg gacgggtgag agctgcagtc agaatatcga tgactgtgct    960
acagccgtgt gtttccatgg ggccacctgc catgaccgtg tggcctcttt ctactgtgcc   1020
tgccctatgg ggaagacagg cctcttgtgt catctggatg atgcatgtgt cagcaacccc   1080
tgccatgagg atgctatctg tgacacaaac cctgtgagtg gccgggccat ctgcacctgc   1140
ccacctggct tcactggagg ggcatgtgac aggatgtgg atgagtgctc gattggtgcc   1200 aaccctgtg aacatttggg tcggtgtgtg aatacacagg gctcattctt gtgccaatgt   1260
ggccgtggct atactggacc tcgctgtgag actgatgtca atgagtgtct ctccggggcc   1320
tgccgcaacc aggccacgtg tcttgaccga attggccagt ttacttgcat ctgcatggca   1380
ggcttcacag ggacctactg tgaggtggac atcgacgaat gtcagagcag cccatgtgtc   1440
aatggtggtg tctgcaagga cagagtcaat ggcttcagct gcacctgccc atcaggattc   1500
agtgggtcca tgtgtcagct ggatgtggat gagtgtgcaa gcactccctg ccggaatggt   1560
gccaagtgtg tggaccagcc tgacggctat gagtgtcgct gtgcagaggg ctttgagggc   1620
actttgtgtg agcgaaacgt ggatgactgc tctccggatc cctgccacca cgggcgctgt   1680
gtcgatggca ttgctagctt ctcgtgtgct tgtgccccag gctatacggg catacgctgt   1740
gagagccagg tggatgagtg ccgcagccag ccctgtcgat atgggggcaa atgtctagac   1800
```

```
ttggtggaca agtacctctg ccgttgtcct cccggaacca caggtgtgaa ctgtgaagtc   1860
aacattgatg actgtgccag taaccnctgt acctttggag tttgccgtga tggcatcaac   1920
cgttatgact gtgtctgtca gcctggattc acagggcccc tctgcaacgt ggagatcaat   1980
gagtgtgcat ccagcccatg tggagagggt ggctcctgtg tggatgggga aaatggcttc   2040
cactgcctct gtccacctgg ctccctgcct ccactttgcc tacctgcgaa ccatccctgt   2100
gcccacaagc cctgtagtca tggagtctgc catgatgcac caggcgggtt ccgctgtgtt   2160
tgtgagcccg ggtggagtgg ccctcgctgt agccagagcc tggctccaga tgcctgtgag   2220
tcccagccct gccaggctgg tggcacctgc accagtgatg aataggctt tcgctgcacc   2280
tgtgcccctg gattccaggg ccatcagtgt gaggtgctgt cccctgtac tccaagcctc   2340
tgtgagcacg gaggccactg tgagtctgac cctgaccggc tgactgtctg ttcctgtccc   2400
ccaggctggc aaggcccacg atgccagcag gatgtggatg aatgtgccgg tgcctcaccc   2460
tgcggccccc atggtacctg caccaacctg ccagggaatt caggtgcat ctgccacagg   2520
ggatacactg gccccttctg tgatcaagac attgacgact gtgacccaa cccgtgcctc   2580
catggtggct cctgccagga tggcgtgggc tccttttcct gttcttgcct cgacggcttt   2640
gctggtcctc gctgtgcccg agatgtggac gaatgtctga gcagcccctg tggccctggc   2700
acctgtactg atcacgtggc ctccttcacc tgtgcctgtc cacctggtta tggaggcttc   2760
cactgtgaga ttgacttgcc ggactgcagc cccagttcct gcttcaatgg agggacctgt   2820
gtggatggcg tgagctcctt cagctgtctg tgtcgccccg gctacacagg cacacactgc   2880
caatacgagg ctgaccctg cttttcccgg ccctgtctgc acgggggcat ctgcaacccc   2940
acccacccag gatttgaatg cacctgccgg gagggcttca ctgggagtca gtgtcagaac   3000
ccagtggact ggtgcagcca ggcaccctgt cagaatgggg gtcgctgtgt ccagactggg   3060
gcttactgca tttgtccacc tggatggagt ggccgcctgt gcgacataca aagcctgccc   3120
tgcacggagg ccgcagccca gatgggggtg aggttggagc agctgtgtca ggaaggtgga   3180
aagtgcatag acaagggccg ctcccactac tgtgtgtgtc cagagggccg tacgggtagt   3240
cactgtgaac acgaggtgga tccctgcacg gcccagcctt gccagcacgg gggcacttgc   3300
cgtggttaca tggggggcta tgtgtgtgag tgtccagctg gctatgctgg tgacagttgt   3360
gaggataata tagatgagtg tgcttcccag ccctgccaga acggaggctc ctgtatcgat   3420
cttgtggccc gctatctctg ttcctgtccc cctggcacac tgggagttct ctgtgagatc   3480
aatgaggacg actgtgacct aggcccatcc ttggactcag gcgttcagtg cctacacaat   3540
ggcacctgtg tggacctggt gggtggcttc cgctgtaact gtcccccagg atacacaggt   3600
ctgcactgtg aggcagacat caatgagtgt cgcccgggtg cctgccatgc agcgcatact   3660
cgggactgcc tacaagatcc aggtgggcat ttccgctgcg tctgccatcc tggcttcaca   3720
gggcctcgct gtcagattgc tctgtccccc tgtgagtccc agccatgtca gcatggaggc   3780
cagtgccgtc acagcctagg ccgtggaggt gggctgacct tcacctgtca ctgtgtcccg   3840
ccattctggg gtctgcgttg tgagcgggtg cacgctctt ccgagagct gcagtgccca   3900
gtgggtatcc catgccagca gacagcccgt ggaccacgct gcgcttgtcc tccggggctg   3960
tccgggcccc cctgccgggt ttctagggcg tcaccctcag gagctactaa cgccagctgc   4020
gcctctgccc cttgtctgca tgggggctca tgcctacctg tacagagtgt cccttctctc   4080
cgctgtgtgt gcgctccggg ctgggcggc ccgcgttgtg agacccctc cgcagcc      4137
```

<210> SEQ ID NO 9
<211> LENGTH: 3510
<212> TYPE: DNA
<213> ORGANISM: Mus musculus

<400> SEQUENCE: 9

| | | | | | | |
|---|---|---|---|---|---|---|
| atgcagcccc | agttgctgct | gctgctgctc | ttgccactca | atttccctgt | catcctgacc | 60 |
| agagagcttc | tgtgtggagg | atccccagag | ccctgtgcca | acggaggcac | ctgcctgagg | 120 |
| ctatctcagg | gacaagggat | ctgccagtgt | gcccctggat | ttctgggtga | gacttgccag | 180 |
| tttcctgacc | cctgcaggga | tacccaactc | tgcaagaatg | gtggcagctg | ccaagccctg | 240 |
| ctccccacac | ccccaagctc | ccgtagtcct | acttctccac | tgaccccctca | cttctcctgc | 300 |
| acctgcccct | ctggcttcac | cggtgatcga | tgccaaaccc | atctggaaga | gctctgtcca | 360 |
| ccttctttct | gttccaacgg | gggtcactgc | tatgttcagg | cctcaggccg | cccacagtgc | 420 |
| tcctgcgagc | tgggtggac | aggtgagcaa | tgccagctcc | gagacttctg | ctcagccaac | 480 |
| ccctgtgcca | acggaggcgt | gtgcctggcc | acatacccc | agatccagtg | ccgctgtcca | 540 |
| cctgggttcg | agggtcacac | ctgtgaacgc | gacatcaacg | agtgcttcct | ggagccggga | 600 |
| ccctgccctc | agggcacctc | ctgccataac | accttgggtt | cctaccagtg | tctctgccct | 660 |
| gtggggcagg | aaggtcccca | gtgcaagctc | aggaagggag | cctgccctcc | tggaagctgt | 720 |
| ctcaatgggg | gcacctgcca | gctggtccca | gagggacact | ccaccttca | tctctgcctc | 780 |
| tgtccccag | gttttcacggg | gctggactgt | gagatgaacc | cagatgactg | tgtcaggcac | 840 |
| cagtgtcaga | acggggccac | ctgtctggat | ggctggata | cctacacctg | cctctgcccc | 900 |
| aagacatgga | agggctggga | ctgctctgaa | gatatagatg | aatgtgaagc | ccggggtccc | 960 |
| cctcgctgca | ggaacggtgg | cacctgccag | aacacagctg | gcagctttca | ctgtgtgtgc | 1020 |
| gtgagtggct | ggggcggtgc | aggttgtgag | gagaacctgg | atgactgtgc | agctgccacc | 1080 |
| tgtgccccgg | gatccacctg | catcgaccgt | gtgggctctt | tctcctgcct | ctgcccacct | 1140 |
| ggacgcacag | gctcctgtgt | ccacctggaa | gacatgtgtt | tgagtcagcc | gtgccacgtg | 1200 |
| aatgccagt | gcagcaccaa | ccctctgaca | ggctccaccc | tctgcatatg | ccagcctggc | 1260 |
| tactcaggat | ccacctgtca | ccaagatctg | gatgagtgcc | aaatggccca | gcaaggaccc | 1320 |
| agtccctgcg | aacatggcgg | ctcctgcatc | aacacccctg | gctccttcaa | ctgcctctgc | 1380 |
| ctgcctggtt | acacgggctc | ccgctgtgaa | gctgaccaca | atgagtgcct | gtcacagccc | 1440 |
| tgccacccag | gcagcacctg | cctggacctg | cttcaacct | ccactgcct | ctgcccacca | 1500 |
| ggcttggaag | ggaggctctg | tgaggtggag | gtcaatgagt | gcacctctaa | tccctgcctg | 1560 |
| aaccaagctg | cctgccatga | cctgctcaac | ggcttccagt | gcctctgcct | tcctggattc | 1620 |
| accggcgccc | gatgtgagaa | agacatggac | gagtgtagca | gcacccctg | tgccaatggg | 1680 |
| gggcgctgcc | gagaccagcc | tggagccttc | tactgcgagt | gtctcccagg | cttgaaggg | 1740 |
| ccacactgtg | agaaagaagt | ggacgaatgt | ctgagtgacc | cctgccccgt | gggagccagc | 1800 |
| tgccttgatc | tccccggagc | attcttctgc | ctctgccgtc | ctggtttcac | aggtcaactt | 1860 |
| tgtgaggttc | ccttgtgcac | ccaacatg | tgccaacctg | acagcaatg | ccaaggtcag | 1920 |
| gaacacagag | cccctgcct | ctgccctgac | ggaagtcctg | gctgtgttcc | tgccgaggac | 1980 |
| aactgcccct | gtcaccatgg | ccattgccag | agatccttgt | gtgtgtgtga | tgagggctgg | 2040 |
| actggaccag | aatgcgagac | agaactgggt | ggctgcatct | ccacaccctg | tgcccatggg | 2100 |
| gggacctgcc | acccacagcc | gtctggctac | aactgtacct | gccctgcagg | ctacatgggg | 2160 |

-continued

```
ttgacctgta gtgaggaggt gacagcttgt cactcagggc cctgtctcaa tggtggctct    2220
tgcagcatcc gtcctgaggg ctattcctgc acctgccttc caagtcacac aggtcgccac    2280
tgccagactg ccgtggacca ctgtgtgtct gcctcgtgcc tcaatggggg tacctgtgtg    2340
aacaagcctg gcactttctt ctgcctctgt gccactggct tccagggggct gcactgtgag    2400 gagaagacta accccagctg tgcagacagc ccctgcagga acaaggcaac ctgccaagac    2460
acacctcgag gggcccgctg cctctgcagc cctggctata caggaagcag ctgccagact    2520
ctgatagact tgtgtgcccg gaagccctgt ccacacactg ctcgatgcct ccagagtggg    2580
ccctcgttcc agtgcctgtg cctccaggga tggacagggg ctctctgtga cttcccactg    2640
tcctgccaga tggccgcaat gagccaaggc atagagatct ctggcctgtg ccagaatgga    2700
ggcctctgta ttgacacggg ctcctcctat ttctgccgct gccctcctgg attccaaggc    2760
aagttatgcc aggataatat gaaccctgc gagcccaatc cctgccatca cgggtctacc    2820
tgtgtgcctc agcccagtgg ctatgtctgc cagtgtgccc caggctatga gggacagaac    2880
tgctcaaaag tacttgaagc ttgtcagtcc cagccctgcc acaaccacgg aacctgtacc    2940
tccaggcctg gaggcttcca ctgtgcctgc cctccaggct tcgtgggact gcgctgtgag    3000
ggagatgtgg atgagtgtct ggaccggccc tgtcacccct cgggcactgc agcttgccac    3060
tctttagcca acgccttcta ctgccagtgt ctgcctgggc acacaggcca gcggtgtgag    3120
gtggagatgg acctctgtca gagccaaccc tgctccaatg aggatcctg tgagatcaca    3180 acagggccac cccctggctt cacctgtcac tgccccaagg gttttgaagg ccccacctgc    3240
agccacaaag ccctttcctg cggcatccat cactgccaca atggaggcct atgtctgccc    3300
tcccctaagc cagggtcacc accactctgt gcctgcctca gtggttttgg gggccctgac    3360
tgtctgacac ctccagctcc accgggctgc ggtcccccct caccctgcct gcacaatggt    3420
acctgcactg agacccctgg gttgggcaac ccgggcttc aatgcacctg ccctcctgac    3480
tctccagggc cccggtgtca aaggccaggg                                     3510
```

<210> SEQ ID NO 10
<211> LENGTH: 15
<212> TYPE: DNA
<213> ORGANISM: Mus musculus

<400> SEQUENCE: 10

```
gatctgggcc cgggc                                                        15
```

<210> SEQ ID NO 11
<211> LENGTH: 4299
<212> TYPE: DNA
<213> ORGANISM: Homo sapien

<400> SEQUENCE: 11

```
atgccgccgc tcctggcgcc cctgctctgc ctggcgctgc tgccgcgct cgccgcacga      60 ggcccgcgat gctcccagcc cggtgagacc tgcctgaatg cgggaagtg tgaagcggcc     120 aatggcacgg aggcctgcgt ctgtggcggg gccttcgtgg gccgcgatg ccaggacccc     180 aacccgtgcc tcagcacccc ctgcaagaac gcgggacat gccacgtggt ggaccgcaga     240
ggcgtggcag actatgcctg cagctgtgcc ctgggcttct ctgggcccct ctgcctgaca     300
cccctggaca tgcctgcct caccaacccc tgccgcaacg ggggcacctg cgacctgctc     360
acgctgacga agtacaagtg ccgctgcccg ccggctggt cagggaaatc gtgccagcag     420
gctgacccgt gcgcctccaa cccctgcgcc aacggtggcc agtgcctgcc cttcgaggcc     480
```

```
tcctacatct gccactgccc acccagcttc catggcccca cctgccggca ggatgtcaac      540
gagtgtggcc agaagcccgg gctttgccgc cacggaggca cctgccacaa cgaggtcggc      600
tcctaccgct gcgtctgccg cgccacccac actggcccca actgcgagcg ccctacgtg       660 ccctgcagcc cctcgccctg ccagaacggg ggcacctgcc gccccacggg cgacgtcacc      720
cacgagtgtg cctgcctgcc aggcttcacc ggccagaact gtgaggaaaa tatcgacgat      780
tgtccaggaa caactgcaa gaacgggggt gcctgtgtgg acggcgtgaa cacctacaac       840
tgccgctgcc cgccagagtg gacaggtcag tactgtaccg aggatgtgga cgagtgccag      900
ctgatgccaa atgcctgcca gaacggcggg acctgccaca cacccacgg tggctacaac       960 tgcgtgtgtg tcaacggctg gactggtgag gactgcagcg agaacattga tgactgtgcc     1020
agcgccgcct gcttccacgg cgccacctgc catgaccgtg tggcctcctt ctactgcgag     1080
tgtccccatg gccgcacagg tctgctgtgc cacctcaacg acgcatgcat cagcaacccc     1140
tgtaacgagg gctccaactg cgacaccaac cctgtcaatg caaggccat ctgcacctgc      1200 ccctcggggt acacgggccc ggcctgcagc caggacgtgg atgagtgctc gctgggtgcc     1260
aacccctgcg agcatgcggg caagtgcatc aacacgctgg gctccttcga gtgccagtgt     1320
ctgcagggct acacgggccc ccgatgcgag atcgacgtca acgagtgcgt ctcgaacccg     1380
tgccagaacg acgccacctg cctggaccag attggggagt ccagtgcat ctgcatgccc      1440 ggctacgagg tgtgcactg cgaggtcaac acagacgagt gtgccagcag ccctgcctg       1500 cacaatggcc gctgcctgga caagatcaat gagttccagt gcgagtgccc cacgggcttc     1560
actgggcatc tgtgccagta cgatgtggac gagtgtgcca gcacccctg caagaatggt     1620 gccaagtgcc tggacggacc caacacttac acctgtgtgt gcacggaagg gtacacgggg     1680
acgcactgcg aggtggacat cgatgagtgc gaccccgacc cctgccacta cggctcctgc     1740
aaggacggcg tcgccaccct cacctgcctc tgccgcccag gctacacggg ccaccactgc     1800
gagaccaaca tcaacgagtg ctccagccag ccctgccgcc acggggcac ctgccaggac      1860 cgcgacaacc cctacctctg cttctgcctg aagggggacca caggacccaa ctgcgagatc     1920
aacctggatg actgtgccag cagcccctgc gactcgggca cctgtctgga caagatcgat     1980
ggctacgagt gtgcctgtga gccgggctac acagggagca tgtgtaacat caacatcgat     2040
gagtgtgcgg gcaaccctg ccacaacggg ggcacctgcg aggacggcat caatggcttc      2100
acctgccgct gccccgaggg ctaccacgac cccacctgcc tgtctgaggt caatgagtgc     2160
aacagcaacc cctgcgtcca gggcctgc cgggacagcc tcaacggta caagtgcgac        2220 tgtgaccctg ggtggagtgg gaccaactgt gacatcaaca caatgagtg tgaatccaac      2280 ccttgtgtca acgcggcac ctgcaaagac atgaccagtg gctacgtgtg cacctgccgg      2340
gagggcttca gcgtcccaa ctgccagacc aacatcaacg agtgtgcgtc caacccatgt     2400
ctgaaccagg gcacgtgtat tgacgacgtt gccgggtaca agtgcaactg cctgctgccc     2460
tacacaggtg ccacgtgtga ggtggtgctg gcccgtgtg ccccagccc ctgcagaaac       2520 ggcggggagt gcaggcaatc cgaggactat gagagcttct cctgtgtctg ccccacgggc     2580
tggcaagcag ggcagacctg tgaggtcgac atcaacgagt gcgttctgag cccgtgccgg     2640
cacggcgcat cctgccagaa cacccacggc ggctaccgct gccactgcca ggccggctac     2700
agtgggcgca actgcgagac cgacatcgac gactgccgc caacccgtg tcacaacggg       2760 ggctcctgca cagacggcat caacacggcc ttctgcgact gctgccggg cttcggggc      2820
```

-continued

| | |
|---|---|
| actttctgtg aggaggacat caacgagtgt gccagtgacc cctgccgcaa cggggccaac | 2880 |
| tgcacggact gcgtggacag ctacacgtgc acctgccccg caggcttcag cgggatccac | 2940 |
| tgtgagaaca acacgcctga ctgcacagag agctcctgct tcaacggtgg cacctgcgtg | 3000 |
| gacggcatca actcgttcac ctgcctgtgt ccacccggct tcacgggcag ctactgccag | 3060 |
| cacgatgtca atgagtgcga ctcacagccc tgcctgcatg gcggcacctg tcaggacggc | 3120 |
| tgcggctcct acaggtgcac ctgccccag ggctacactg cccccaactg ccagaacctt | 3180 |
| gtgcactggt gtgactcctc gccctgcaag aacggcggca aatgctggca gacccacacc | 3240 |
| cagtaccgct gcgagtgccc cagcggctgg accggccttt actgcgacgt gcccagcgtg | 3300 |
| tcctgtgagg tggctgcgca gcgacaaggt gttgacgttg cccgcctgtg ccagcatgga | 3360 |
| gggctctgtg tggacgcggg caacacgcac cactgccgct gccaggcggg ctacacaggc | 3420 |
| agctactgtg aggacctggt ggacgagtgc tcacccagcc cctgccagaa cggggccacc | 3480 |
| tgcacggact acctgggcgg ctactcctgc aagtgcgtgg ccggctacca cggggtgaac | 3540 |
| tgctctgagg agatcgacga gtgcctctcc caccccctgcc agaacggggg cacctgcctc | 3600 |
| gacctcccca acacctacaa gtgctcctgc ccacggggca ctcagggtgt gcactgtgag | 3660 |
| atcaacgtgg acgactgcaa tccccccgtt gaccccgtgt cccggagccc caagtgcttt | 3720 |
| aacaacggca cctgcgtgga ccaggtgggc ggctacagct gcacctgccc gccgggcttc | 3780 |
| gtgggtgagc gctgtgaggg ggatgtcaac gagtgcctgt ccaatccctg cgacgcccgt | 3840 |
| ggcacccaga actgcgtgca gcgcgtcaat gacttccact gcgagtgccg tgctggtcac | 3900 |
| accgggcgcc gctgcgagtc cgtcatcaat ggctgcaaag gcaagccctg caagaatggg | 3960 |
| ggcacctgcg ccgtggcctc caacaccgcc cgcgggttca tctgcaagtg ccctgcgggc | 4020 |
| ttcgagggcg ccacgtgtga gaatgacgct cgtacctgcg gcagcctgcg ctgcctcaac | 4080 |
| ggcggcacat gcatctccgg cccgcgcagc cccacctgcc tgtgcctggg ccccttcacg | 4140 |
| ggccccgaat gccagttccc ggccagcagc ccctgcctgg gcggcaaccc ctgctacaac | 4200 |
| caggggacct gtgagcccac atccgagagc cccttctacc gttgcctgtg ccccgccaaa | 4260 |
| ttcaacgggc tcttgtgcca catcctggac tacagcttc | 4299 |

```
<210> SEQ ID NO 12
<211> LENGTH: 4213
<212> TYPE: DNA
<213> ORGANISM: Homo sapien

<400> SEQUENCE: 12
```

| | |
|---|---|
| tcatctggaa ttatgcccgc cctgcgcccc gctctgctgt gggcgctgct ggcgctctgg | 60 |
| ctgtgctgcg cggcccccgc gcatgcattg cagtgtcgag atggctatga acctgtgta | 120 |
| aatgaaggaa tgtgtgttac ctaccacaat ggcacaggat actgcaaatg tccagaaggc | 180 |
| ttcttggggg aatattgtca acatcgagac ccctgtgaga gaaccgctg ccagaatggt | 240 |
| gggacttgtg tggcccaggc catgctgggg aaagccacgt gccgatgtgc ctcagggttt | 300 |
| acaggagagg actgccagta ctcaacatct catccatgct ttgtgtctcg accctgcctg | 360 |
| aatggcggca catgccatat gctcagccgg gataccctatg agtgcacctg tcaagtcggg | 420 |
| tttacaggta aggagtgcca atggacggat gcctgcctgt ctcatccctg tgcaaatgga | 480 |
| agtacctgta ccactgtggc caaccagttc tcctgcaaat gcctcacagg cttcacaggg | 540 |
| cagaaatgtg agactgatgt caatgagtgt gacattccag acactgcca gcatggtggc | 600 |
| acctgcctca acctgcctgg ttcctaccag tgccagtgcc ctcagggctt cacaggccag | 660 |

```
tactgtgaca gcctgtatgt gccctgtgca ccctcacctt gtgtcaatgg aggcacctgt    720
cggcagactg gtgacttcac tttttgagtgc aactgccttc caggttttga agggagcacc    780
tgtgagagga atattgatga ctgccctaac cacaggtgtc agaatggagg gtttgtgtg    840 gatggggtca acacttacaa ctgccgctgt cccccacaat ggacaggaca gttctgcaca    900
gaggatgtgg atgaatgcct gctgcagccc aatgcctgtc aaaatggggg cacctgtgcc    960
aaccgcaatg gaggctatgg ctgtgtatgt gtcaacggct ggagtggaga tgactgcagt   1020
gagaacattg atgattgtgc cttcgcctcc tgtactccag gctccacctg catcgaccgt   1080
gtggcctcct tctcttgcat gtgcccagag gggaaggcag gtctcctgtg tcatctggat   1140
gatgcatgca tcagcaatcc ttgccacaag ggggcactgt gtgacaccaa ccccctaaat   1200
gggcaatata tttgcacctg cccacaaggc tacaaagggg ctgactgcac agaagatgtg   1260
gatgaatgtg ccatggccaa tagcaatcct tgtgagcatg caggaaaatg tgtgaacacg   1320
gatggcgcct tccactgtga gtgtctgaag ggttatgcag gacctcgttg tgagatggac   1380
atcaatgagt gccattcaga cccctgccag aatgatgcta cctgtctgga taagattgga   1440
ggcttcacat gtctgtgcat gccaggtttc aaaggtgtgc attgtgaatt agaaataaat   1500
gaatgtcaga gcaaccccttg tgtgaacaat gggcagtgtg tggataaagt caatcgttc    1560 cagtgcctgt gtcctcctgg tttcactggg ccagtttgcc agattgatat tgatgactgt   1620
tccagtactc cgtgtctgaa tggggcaaag tgtatcgatc acccgaatgg ctatgaatgc   1680
cagtgtgcca caggtttcac tggtgtgttg tgtgaggaga acattgacaa ctgtgacccc   1740
gatccttgcc accatggtca gtgtcaggat ggtattgatt cctacacctg catctgcaat   1800
cccgggtaca tgggcgccat ctgcagtgac cagattgatg aatgttacag cagcccttgc   1860
ctgaacgatg gtcgctgcat tgacctggtc aatggctacc agtgcaactg ccagccaggc   1920
acgtcagggg ttaattgtga aattaatttt gatgactgtg caagtaaccc ttgtatccat   1980
ggaatctgta tggatggcat taatcgctac agttgtgtct gctcaccagg attcacaggg   2040
cagagatgta acattgacat tgatgagtgt gcctccaatc cctgtcgcaa gggtgcaaca   2100
tgtatcaacg gtgtgaatgg tttccgctgt atatgccccg agggacccca tcaccccagc   2160
tgctactcac aggtgaacga atgcctgagc aatccctgca tccatggaaa ctgtactgga   2220
ggtctcagtg gatataagtg tctctgtgat gcaggctggg ttggcatcaa ctgtgaagtg   2280
gacaaaaatg aatgcctttc gaatccatgc cagaatggag gaacttgtga caatctggtg   2340
aatggataca ggtgtacttg caagaagggc tttaaaggct ataactgcca ggtgaatatt   2400
gatgaatgtg cctcaaatcc atgcctgaac caaggaacct gctttgatga cataagtggc   2460
tacacttgcc actgtgtgct gccatacaca ggcaagaatt gtcagacagt attggctccc   2520
tgttccccaa acccttgtga gaatgctgct gtttgcaaag agtcaccaaa ttttgagagt   2580
tatacttgct gtgtgctcc tggctggcaa ggtcagcggt gtaccattga cattgacgag   2640
tgtatctcca gccctgcat gaaccatggt ctctgccata acacccaggg cagctacatg   2700
tgtgaatgtc caccaggctt cagtggtatg gactgtgagg aggacattga tgactgcctt   2760
gccaatcctt gccagaatgg aggttcctgt atggatggag tgaatacttt ctcctgcctc   2820
tgccttccgg gtttcactgg ggataagtgc cagacagaca tgaatgagtg tctgagtgaa   2880
ccctgtaaga atggagggac ctgctctgac tacgtcaaca gttacacttg caagtgccag   2940
gcaggatttg atggagtcca ttgtgagaac aacatcaatg agtgcactga gagctcctgt   3000
```

| | |
|---|---|
| ttcaatggtg gcacatgtgt tgatgggatt aactccttct cttgcttgtg ccctgtgggt | 3060 |
| ttcactggat ccttctgcct ccatgagatc aatgaatgca gctctcatcc atgcctgaat | 3120 |
| gagggaacgt gtgttgatgg cctgggtacc taccgctgca gctgccccct gggctacact | 3180 |
| gggaaaaact gtcagaccct ggtgaatctc tgcagtcggt ctccatgtaa aaacaaaggt | 3240 |
| acttgtgttc agaaaaaagc agagtcccag tgcctatgtc catctggatg gctggtgcc | 3300 |
| tattgtgacg tgcccaatgt ctcttgtgac atagcagcct ccaggagagg tgtgcttgtt | 3360 |
| gaacacttgt gccagcactc aggtgtctgc atcaatgctg gcaacacgca ttactgtcag | 3420 |
| tgcccctgg gctatactgg gagctactgt gaggagcaac tcgatgagtg tgcgtccaac | 3480 |
| ccctgccagc acgggcaac atgcagtgac ttcattggtg gatacagatg cgagtgtgtc | 3540 |
| ccaggctatc agggtgtcaa ctgtgagtat gaagtggatg agtgccagaa tcagccctgc | 3600 |
| cagaatggag gcacctgtat tgaccttgtg aaccatttca gtgctcttg cccaccaggc | 3660 |
| actcggggcc tactctgtga agagaacatt gatgactgtg cccgggggtcc ccattgcctt | 3720 |
| aatggtggtc agtgcatgga taggattgga ggctacagtt gtcgctgctt gcctggcttt | 3780 |
| gctggggagc gttgtgaggg agacatcaac gagtgcctct ccaaccctg cagctctgag | 3840 |
| ggcagcctgg actgtataca gctcaccaat gactacctgt gtgtttgccg tagtgccttt | 3900 |
| actgccggc actgtgaaac cttcgtcgat gtgtgtcccc agatgccctg cctgaatgga | 3960 |
| gggacttgtg ctgtggccag taacatgcct gatggtttca tttgccgttg tccccgggga | 4020 |
| ttttccgggg caaggtgcca gagcagctgt ggacaagtga atgtaggaa gggggagcag | 4080 |
| tgtgtgcaca ccgcctctgg accccgctgc ttctgcccca gtccccggga ctgcgagtca | 4140 |
| ggctgtgcca gtagccctg ccagcacggg ggcagctgcc accctcagcg ccagcctcct | 4200 |
| tattactcct gcc | 4213 |

<210> SEQ ID NO 13
<211> LENGTH: 3974
<212> TYPE: DNA
<213> ORGANISM: Homo sapien

<400> SEQUENCE: 13

| | |
|---|---|
| atggggccgg gggcccgtgg ccgccgccgc cgccgtcgcc cgatgtcgcc gccaccgcca | 60 |
| ccgccacccg tgcgggcgct gccctgctg ctgctgctag cggggccggg ggctgcagcc | 120 |
| cccccttgcc tggacggaag cccgtgtgca aatggaggtc gttgcaccca gctgccctcc | 180 |
| cgggaggctg cctgcctgtg cccgcctggc tgggtgggta gcggtgtca gctggaggac | 240 |
| ccctgtcact caggcccctg tgctggccgt ggtgtctgcc agagttcagt ggtggctggc | 300 |
| accgcccgat tctcatgccg gtgccccgt ggcttccgag ccctgactg ctccctgcca | 360 |
| gatccctgcc tcagcagccc ttgtgcccac ggtgcccgct gctcagtggg gcccgatgga | 420 |
| cgcttcctct gctcctgccc acctggctac cagggccgca gctgccgaag cgacgtggat | 480 |
| gagtgccggg tgggtgagcc ctgccgccat ggtggcacct gcctcaacac acctggctcc | 540 |
| ttccgctgcc agtgtccagc tggctacaca gggccactat gtgagaaccc cgcggtgccc | 600 |
| tgtgcaccct caccatgccg taacgggggc acctgcaggc agagtggcga cctcacttac | 660 |
| gactgtgcct gtcttcctgg gtttgagggt cagaattgtg aagtgaacgt ggacgactgt | 720 |
| ccaggacacc gatgtctcaa tgggggaca tgcgtggatg gcgtcaacac ctataactgc | 780 |
| cagtgccctc ctgagtggac aggccagttc tgcacgagg acgtggatga gtgtcagctg | 840 |
| cagcccaacg cctgccacaa tgggggtacc tgcttcaaca cgctgggtgg ccacagctgc | 900 |

-continued

```
gtgtgtgtca atggctggac aggcgagagc tgcagtcaga atatcgatga ctgtgccaca    960
gccgtgtgct tccatggggc cacctgccat gaccgcgtgg cttctttcta ctgtgcctgc   1020
cccatgggca agactggcct cctgtgtcac ctggatgacg cctgtgtcag caaccnctgc   1080
cacgaggatg ctatctgtga cacaaatccg gtgaacggcc gggccatttg cacctgtcct   1140
cccggcttca cgggtggggc atgtgaccag gatgtggacg agtgctctat cggcgccaac   1200
ccctgcgagc acttgggcag gtgcgtgaac acgcagggct ccttcctgtg ccagtgcggt   1260
cgtggctaca ctggaccntcg ctgtgagacc gatgtcaacg agtgtctgtc ggggccctgc   1320
cgaaaccagg ccacgtgcct cgaccgcata ggccagttca cctgtatctg tatggcaggc   1380
ttcacaggaa cctattgcga ggtggacatt gacgagtgtc agagtagccc ctgtgtcaac   1440
ggtggggtct gcaaggaccg agtcaatggc ttcagctgca cctgcccctc gggcttcagc   1500
ggctccacgt gtcagctgga cgtggacgaa tgcgccagca cgccctgcag gaatggcgcc   1560
aaatgcgtgg accagcccga tggctacgag tgccgctgtg ccgagggctt tgagggcacg   1620
ctgtgtgatc gcaacgtgga cgactgctcc cctgacccat gccaccatgg tcgctgcgtg   1680
gatggcatcg ccagcttctc atgtgcctgt gctcctggct acacgggcac acgctgcgag   1740
agccaggtgg acgaatgccg cagccagccc tgccgccatg gcggcaaatg cctagacctg   1800
gtggacaagt acctctgccg ctgcccttct gggaccacag gtgtgaactg cgaagtgaac   1860
attgacgact gtgccagcaa cccctgcacc tttggagtct gccgtgatgg catcaaccgc   1920
tacgactgtg tctgccaacc tggcttcaca gggccccttt gtaacgtgga gatcaatgag   1980
tgtgcttcca gcccatgcgg cgagggaggt tcctgtgtgg atgggaaaaa tggcttccgc   2040
tgcctctgcc cgcctggctc cttgccccca ctctgcctcc ccccgagcca tccctgtgcc   2100
catgagccct gcagtcacgg catctgctat gatgcacctg gcgggttccg ctgtgtgtgt   2160
gagcctggct ggagtggccc ccgctgcagc cagagcctgg cccgagacgc ctgtgagtcc   2220
cagccgtgca gggccggtgg gacatgcagc agcgatggaa tgggtttcca ctgcacctgc   2280
ccgcctggtg tccagggacg tcagtgtgaa ctcctctccc cctgcacccc gaaccnctgt   2340
gagcatgggg ccgctgcgga gtctgcccct ggccagctgc ctgtctgctc ctgccccag   2400
ggctggcaag gccacgatg ccagcaggat gtggacgagt gtgctggccc cgcacnctgt   2460
ggccctcatg gtatctgcac caacctggca gggagtttca gctgcacctg ccatggaggg   2520
tacactggcc cttcctgcga tcaggacatc aatgactgtg accccaaccc atgcctgaac   2580
ggtggctcgt gccaagacgg cgtgggctcc ttttcctgct cctgcctccc tggtttcgcc   2640
ggccacgat gcgcccgcga tgtggatgag tgcctgagca ccccctgcgg cccgggcacc   2700
tgtaccgacc acgtggcctc cttcacctgc acctgcccgc caggctacgg aggcttccac   2760
tgcgaacagg acctgcccga ctgcagcccc agctcctgct tcaatggcgg gacctgtgtg   2820
gacggcgtga actcgttcag ctgcctgtgc cgtcccggct acacaggagc ccactgccaa   2880
catgaggcag acccctgcct ctcgcggccc tgcctacacg ggggcgtctg cagcgccgcc   2940
caccctggct tccgctgcac ctgcctcgag agcttcacgg gccgcagtg ccagacgctg   3000
gtggattggt gcagccgcca gccttgtcaa aacgggggtc gctgcgtcca gactggggcc   3060
tattgccttt gtccccctgg atggagcgga cgcctctgtg acatccgaag cttgccctgc   3120
agggaggccg cagcccagat cggggtgcgg ctggagcagc tgtgtcaggc gggtgggcag   3180
tgtgtggatg aagacagctc ccactactgc gtgtgcccag agggccgtac tggtagccac   3240
```

-continued

```
tgtgagcagg aggtggaccc ctgcttggcc cagccctgcc agcatggggg gacctgccgt    3300
ggctatatgg ggggctacat gtgtgagtgt cttcctggct acaatggtga taactgtgag    3360
gacgacgtgg acgagtgtgc ctcccagccc tgccagcacg ggggttcatg cattgacctc    3420
gtggcccgct atctctgctc ctgtccccca ggaacgctgg gggtgctctg cgagattaat    3480
gaggatgact gcggcccagg cccaccgctg gactcagggc cccggtgcct acacaatggc    3540
acctgcgtgg acctggtggg tggtttccgc tgcacctgtc ccccaggata cactggtttg    3600
cgctgcgagg cagacatcaa tgagtgtcgc tcaggtgcct gccacgcggc acacacccgg    3660
gactgcctgc aggacccagg cggaggtttc cgttgccttt gtcatgctgg cttctcaggt    3720
cctcgctgtc agactgtcct gtctccctgc gagtcccagc catgccagca tggaggccag    3780
tgccgtccta gcccgggtcc tggggtgggg ctgaccttca cctgtcactg tgcccagccg    3840
ttctggggtc cgcgttgcga gcgggtggcg cgctcctgcc gggagctgca gtgcccggtg    3900
ggcgtcccat gccagcagac gccccgcggg ccgcgctgcg cctgccccca agggttgtcg    3960
ggaccctcct gccg                                                     3974

<210> SEQ ID NO 14
<211> LENGTH: 3522
<212> TYPE: DNA
<213> ORGANISM: Homo sapien

<400> SEQUENCE: 14
atgcagcccc cttcactgct gctgctgctg ctgctgctgc tgctgctatg tgtctcagtg      60
gtcagaccca gagggctgct gtgtgggagt ttcccagaac cctgtgccaa tggaggcacc     120
tgcctgagcc tgtctctggg acaagggacc tgccagtgtg ccctggcttc ctgggtgag     180 acgtgccagt tcctgacccc tgccagaac gcccagctct gccaaaatgg aggcagctgc     240
caagccctgc ttcccgctcc cctagggctc cccagctctc cctctccatt gacacccagc     300
ttcttgtgca cttgcctccc tggcttcact ggtgagagat gccaggccaa gcttgaagac     360
ccttgtcctc cctccttctg ttccaaaagg ggccgctgcc acatccaggc ctcgggccgc     420
ccacagtgct cctgcatgcc tggatggaca ggtgagcagt gccagcttcg ggacttctgt     480
tcagccaacc catgtgttaa tggagggggtg tgtctggcca catacccca gatccagtgc     540 cactgcccac cgggcttcga gggccatgcc tgtgaacgtg atgtcaacga gtgcttccag     600
gacccaggac cctgccccaa aggcacctcc tgccataaca ccctgggctc cttccagtgc     660 ctctgcccctg tggggcagga gggtccacgt tgtgagctgc gggcaggacc ctgccctcct     720 agggggctgtt cgaatggggg cacctgccag ctgatgccag agaaagactc caccttttcac     780 ctctgcctct gtcccccagg tttcataggc ccagactgtg aggtgaatcc agacaactgt     840
gtcagccacc agtgtcagaa tggggggcact tgccaggatg gctggacac ctacacctgc     900 ctctgcccag aaacctggac aggctgggac tgctccgaag atgtggatga gtgtgagacc     960
cagggtcccc ctcactgcag aaacgggggc acctgccaga actctgctgg tagctttcac    1020
tgcgtgtgtg tgagtggctg gggcggcaca agctgtgagg agaacctgga tgactgtatt    1080
gctgccacct gtgccccggg atccacctgc attgaccggg tgggctcttt ctcctgcctc    1140
tgcccacctg gacgcacagg actcctgtgc cacttggaag acatgtgtct gagccagccg    1200
tgccatgggg atgcccaatg cagcaccaac cccctcacag gctccacact ctgcctgtgt    1260
cagcctggct attcggggcc cacctgccac caggacctgg acgagtgtct gatgccccag    1320
caaggcccaa gtccctgtga acatggcggt tcctgcctca cactcctggg ctccttcaac    1380
```

```
tgcctctgtc cacctggcta cacaggctcc cgttgtgagg ctgatcacaa tgagtgcctc    1440
tcccagccct gccacccagg aagcacctgt ctggacctac ttgccaccat ccactgcctc    1500
tgcccgccag gcttagaagg gcagctctgt gaggtggaga ccaacgagtg tgcctcagct    1560
ccctgcctga accacgcgga ttgccatgac ctgctcaacg gcttccagtg catctgcctg    1620
cctggattct ccggcacccg atgtgaggag gatatcgatg agtgcagaag ctctccctgt    1680
gccaatggtg ggcagtgcca ggaccagcct ggagccttcc actgcaagtg tctcccaggc    1740
tttgaagggc cacgctgtca aacagaggtg gatgagtgcc tgagtgaccc atgtcccgtt    1800
ggagccagct gccttgatct tccaggagcc ttcttttgcc tctgcccctc tggtttcaca    1860
ggccagctct gtgaggttcc cctgtgtgct cccaacctgt gccagcccaa gcagatatgt    1920
aaggaccaga agacaaggc caactgcctc tgtcctgatg gaagccctgg ctgtgcccca    1980
cctgaggaca actgcacctg ccaccacggg cactgccaga gatcctcatg tgtgtgtgac    2040
gtgggttgga cggggccaga gtgtgaggca gagctagggg gctgcatctc tgcaccctgt    2100
gcccatgggg ggacctgcta cccccagccc tctggctaca actgcacctg ccctacaggc    2160
tacacaggac ccacctgtag tgaggagatg acagcttgtc actcagggcc atgtctcaat    2220
ggcggctcct gcaaccctag ccctggaggc tactactgca cctgccctcc aagccacaca    2280
gggccccagt gccaaaccag cactgactac tgtgtgtctg ccccgtgctt caatgggggt    2340
acctgtgtga acaggcctgg caccttctcc tgcctctgtg ccatgggctt ccagggcccg    2400
cgctgtgagg gaaagctccg ccccagctgt gcagacagcc cctgtaggaa tagggcaacc    2460
tgccaggaca gccctcaggg tccccgctgc ctctgcccca ctggctacac cggaggcagc    2520
tgccagactc tgatggactt atgtgcccag aagccctgcc cacgcaattc ccactgcctc    2580
cagactgggc cctccttcca ctgcttgtgc ctccagggat ggaccgggcc tctctgcaac    2640
cttccactgt cctcctgcca gaaggctgca ctgagccaag gcatagacgt ctcttccctt    2700
tgccacaatg gaggcctctg tgtcgacagc ggcccctcct atttctgcca ctgccccct     2760 ggattccaag gcagcctgtg ccaggatcac gtgaacccat gtgagtccag gccttgccag    2820
aacgggccca cctgcatggc ccagcccagt gggtatctct gccagtgtgc cccaggctac    2880
gatggacaga actgctcaaa ggaactcgat gcttgtcagt cccaaccctg tcacaaccat    2940
ggaacctgta ctcccaaacc tggaggattc cactgtgcct gccctccagg ctttgtgggg    3000
ctacgctgtg agggagacgt ggacgagtgt ctggaccagc cctgccaccc cacaggcact    3060
gcagcctgcc actctctggc caatgccttc tactgccagt gtctgctgg acacacaggc    3120 cagtggtgtg aggtggagat agaccctgc cacagccaac cctgctttca tggagggacc    3180
tgtgaggcca gcaggatc accctgggt ttcatctgcc actgccccaa gggttttgaa    3240
ggccccacct gcagccacag ggccccttcc tgcggcttcc atcactgcca ccacggaggc    3300
ctgtgtctgc cctccctaa gccaggcttc ccaccacgct gtgcctgcct cagtggctat    3360
gggggtcctg actgcctgac ccaccagct cctaaaggct gtggccctcc ctcccatgc    3420 ctatacaatg gcagctgctc agagaccacg ggccttgggg gccaggctt tcgatgctcc    3480 tgccctcaca gctctccagg gccccggtgt cagaaacccg ga                      3522
```

NOTCH-BASED FUSION PROTEINS AND USES THEREOF

This application claims the benefit of U.S. Provisional Application No. 60/566,877, filed Apr. 29, 2004, the contents of which are thereby incorporated herein by reference.

The invention disclosed herein was made with United States government support under grant number R01 HL62454 from the National Institutes of Health. Accordingly, the United States government has certain rights in this invention.

Throughout this application, various publications are referenced by arabic numbers within parentheses or by author and publication date within parentheses. Full citations for these publications may be found at the end of the specification. The disclosures or these publications are hereby incorporated by reference into this application to describe more fully the art to which this invention pertains.

BACKGROUND OF THE INVENTION

Vascular development

During mammalian embryogenesis, formation of the vascular system is an early and essential process. In the embryo, vascular development initiates with the pluripotent hemangioblast derived from the paraxial and lateral plate mesoderm. The hemangioblast has the potential to differentiate into either a hematopoietic progenitor or an endothelial cell progenitor, known as the angioblast.

Vascular development begins with a process known as vasculogenesis whereby angioblasts differentiate into endothelial cells and migrate together to form the primitive vascular plexus. This initial vascular network consists of vessels that are homogenous in size and made up wholly of endothelial cells. The vascular plexus is then remodeled via angiogenesis.

Angiogenesis involves the sprouting of new vessels, the migration of these vessels into avascular regions, and the recruitment of accessory cells, pericytes and smooth muscle cells (Gale and Yancopoulos, 1999). The smooth muscle cells that differentiate and form the contractile vessel walls originate from multiple progenitors including neural crest cells, mesenchymal cells and even endothelial cells (Owens, 1995). In adults, angiogenesis is involved in follicular development, wound healing, and pathological processes such as tumor angiogenesis and heart disease.

The Notch Family and Notch Ligands

Studies of *Drosophila, C. Elegans*, zebrafish and mammals have demonstrated that the Notch pathway is an evolutionarily conserved signaling mechanism that functions to modulate numerous cell-fate decisions. Notch signaling is required for the proper patterning of cells originating from all three germ layers. Depending on the cellular context, Notch signaling may both inhibit and induce differentiation, induce proliferation, and promote cell survival (Artavanis-Tsakonas et al., 1995; Lewis, 1998; Weinmaster, 1997). In *Drosophila*, a single Notch protein is activated by two ligands, Serrate and Delta. In mammals these families have been expanded to four Notch genes (Notch1, Notch2, Notch3 and Notch4) and five ligands, 2 Serrate-like (Jagged1-2) and 3 Delta (Dll, 3, 4) (Bettenhausen et al., 1995; Dunwoodie et al., 1997; Gallahan and Callahan, 1997; Lardelli et al., 1994; Lindsell et al., 1995; Shawber et al., 1996a; Shutter et al., 2000a; Uyttendaele et al., 1996; Weinmaster et al., 1992; Weinmaster et al., 1991). During embryogenesis, Notch receptors and ligands are expressed in dynamic spatial and temporal patterns. However, it is not known if all ligands activate all receptors.

Notch Signaling and Function

Notch signaling influences many different types of cell-fate decisions by providing inhibitory, inductive or proliferative signals depending on the environmental context (reviewed in Artavanis-Tsakonas et al., 1995; Greenwald, 1998; Robey, 1997; Vervoort et al., 1997). This pleiotropic function suggests that Notch modulates multiple signaling pathways in a spatio-temporal manner.

Consistent with Notch regulating cell-fate decisions, both the receptors and ligands are cell surface proteins with single transmembrane domains (FIG. 1). The regulatory extracellular domain of Notch proteins consists largely of tandemly arranged EGF-like repeats that are required for ligand binding (Artavanis-Tsakonas et al., 1995; Weinmaster, 1998). C-terminal to the EGF-like repeats are an additional three cysteine-rich repeats, designated the LIN12/Notch repeats (LNR) (Greenwald, 1994). Downstream of the LNR lies the proteolytic cleavage sequence (RXRR) that is recognized by a furin-like convertase. For Notch1, cleavage at this site yields a 180 kilodalton extracellular peptide and a 120 kilodalton intracellular peptide that are held together to generate a heterodimeric receptor at the cell surface (Blaumueller et al., 1997; Kopan et al., 1996; Logeat et al., 1998).

The intracellular domain of Notch (NotchICD, FIG. 1) rescues loss-of-function Notch phenotypes indicating that this form of Notch signals constitutively (Fortini and Artavanis-Tsakonas, 1993; Lyman and Young, 1993; Rebay et al., 1993; Struhl et al., 1993).

The cytoplasmic domain of Notch contains three identifiable domains: the RAM domain, the ankyrin repeat domain and the C-terminal PEST domain (FIG. 1). Upon ligand-activation Notch undergoes two additional proteolytic cleavages which results in the release of the cytoplasmic domain (Weinmaster, 1998). This Notch peptide translocates to the nucleus and interacts with transcriptional repressors known as CSL (CBF, Su (H), Lag-2) and converts it to transcriptional activator. The CSL/Notch interaction is dependent on the presence of the RAM domain of Notch; while, transcriptional activity also requires the presence of the ankyrin repeats (Hsieh et al., 1996; Hsieh et al., 1997; Roehl et al., 1996; Tamura et al., 1995; Wettstein et al., 1997). Both in vivo and in vitro studies indicate that the HES and Hey genes are the direct targets of Notch/CSL-dependent signaling (Bailey and Posakony, 1995; Eastman et al., 1997; Henderson et al., 2001; Jarriault et al., 1995; Nakagawa et al., 2000; Wettstein et al., 1997). The HES and Hey genes are bHLH transcriptional repressor that bind DNA at N-boxes (Nakagawa et al., 2000; Sasai et al., 1992; Tietze et al., 1992). Notch has also been proposed to signal by a CSL-independent pathway. In fact, expression of just the ankyrin repeat domain is necessary and sufficient for some forms of Notch signaling (Lieber et al., 1993; Matsuno et al., 1997; Shawber et al., 1996b).

Finally, the PEST domain has been implicated in protein turnover by a SEL-10/ubiquitin-dependent pathway (Greenwald, 1994; Oberg et al., 2001; Rogers et al., 1986; Wu et al., 1998; Wu et al., 2001). Similar to the receptors, the extracellular domain of the Notch ligands also consist mostly of tandemly arranged EGF-like repeats (FIG. 1). Upstream of these repeats is a divergent EGF-like repeat known as the DSL (Delta, Serrate, Lag-2) that is required for ligand binding and activation of the receptors (Artavanis-Tsakonas et al., 1995).

Notch Signaling and Vascular Development

Although many of the genes that function to induce vasculogenesis and angiogenesis have been identified, little is known about how cell-fate decisions are specified during vascular development. A number of observations suggest that the Notch signaling pathway may play a role in cell fate determination and patterning of the vascular system.

Notch1, Notch4, Jagged1 and Dll4 are all expressed in the developing vasculature, while Notch3 is expressed in the accessory smooth muscle cells (Krebs et al., 2000; Shutter et al., 2000b; Uyttendaele et al., 1996; Villa et al., 2001; Xue et al., 1999). Mice lacking Jagged1 are embryonic lethal and have severe vascular defects (Xue et al., 1999). Mice nullizygous for Notch1 are embryonic lethal and die of severe neuronal defects, but also have defects in angiogenesis (Krebs et al., 2000; Swiatek et al., 1994). Mice lacking Notch4 are born and appear to be normal, but embryos that have lost both Notch1 and Notch4 die at E9.5 of severe hemorrhaging and vascular patterning defects indicating Notch1 and Notch4 may be functionally redundant during vascular development (Krebs et al., 2000). Exogenous expression of an activated form of Notch4 in endothelium also resulted in vascular defects similar to those seen for the double Notch1/Notch4 nullizygous mice, suggesting that appropriate levels of Notch signaling is critical for proper development of the embryonic vasculature (Uyttendaele et al., 2001).

Taken together, the data from mice mutant for Notch/Notch signaling components uncover several processes dependent on Notch including vascular remodeling, arterial venous specification, vascular smooth muscle cell recruitment and heart/heart outflow vessel development.

Recent experiments have implicated Notch signaling in arterial/venous endothelial cell specification. In situ analysis of E13.5 embryos found that Notch1, Notch3, Notch4, Dl4, Jagged1 and Jagged2 expression was restricted to the arteries and absent in the veins (Villa et al., 2001). Consistent with expression data, disruption of Notch signaling in Zebrafish was associated with loss of the arterial marker ephrinB2; while, ectopic expression of an activated form of Notch lead to a loss in the venous cell marker EphB4 within the dorsal aorta (Lawson et al., 2001). These data suggest that Notch signaling may help to specify arterial and venous cell fates during angiogenesis.

Taken together, the data from mice mutant for Notch/Notch signaling components uncover several processes dependent on Notch including vascular remodeling, arterial venous specification, vascular smooth muscle cell recruitment and heart/heart outflow vessel development.

Notch signaling has also been suggested to function in the adult vascular system. In humans, missense mutations in the extracellular domain of Notch3 correlate with the development of the degenerative vascular disease, CADASIL (Caronti et al., 1998; Desmond et al., 1998; Joutel et al., 2000; Joutel et al., 1996). In a wound healing model, an increase in Jagged1 expression was observed at the regenerating endothelial wound edge, suggesting Notch signaling may function during processes of adult angiogenesis (Lindner et al., 2001). Taken together these data support Notch signaling functions at a number of critical steps during vascular development: vasculogenesis, vascular patterning/angiogenesis, and arterial/venous specification. However, the molecular mechanism(s) by which the Notch signaling pathways influence these different steps has yet to be elucidated.

Significance

Shimizu et al. (*J. Biol. Chem.* 274(46): 32961-32969 (1999)) describe the use of Notch1ECD/Fc, Notch2ECD/Fc and Notch3ECD/Fc in binding studies. However, Shimizu et al. do not mention the use of such proteins for inhibiting angiogenesis.

U.S. Pat. No. 6,379,925 issued Apr. 30, 2002 to Kitajewsky et al. describes murine Notch4. However, it does not describe Notch-based fusion proteins as set forth in the subject application.

This invention differs from the prior art because it is the first study using Notch-based fusion proteins comprising the extracellular domain of Notch operably affixed to a half-life-increasing moiety to inhibit angiogenesis. This invention therefore provides an advantage over the prior art in that it provides evidence that such Notch-based fusion proteins are capable of inhibiting angiogenesis.

Notch proteins play key roles in developmental decisions involving the vasculature, the hematopoietic system, and the nervous system. As such, an understanding of their function is key to understanding how cell-fate decisions and commitment are controlled during development and in adult tissues. To date, several reports on Notch or Notch ligand gene disruptions have described vascular phenotypes providing emphasis that this pathway is a fundamental part of the machinery that guides vascular development. Aberrant Notch activity has been linked to human pathologies; including both cancer and vascular disorders (CADASIL). The analysis of Notch in tumor angiogenesis has only recently begun; however, our discovery of potential downstream targets of Notch suggests a roles in pathological processes associated with angiogenesis. For instance, VEGFR-3 has been linked to both tumor angiogenesis and tumor lymphangiogenesis. The expression or function of several other potential Notch targets has also been linked to tumor angiogenesis; including ephrinB2, Id3, Angiopoietin 1, and PDGF-B. Insights on the role of these targets in Notch gene function will clearly facilitate future analysis of Notch in human pathologies.

SUMMARY OF THE INVENTION

This invention provides a method for treating a subject having a tumor comprising administering to the subject an effective amount of a composition of matter comprising the extracellular domain of a Notch receptor protein operably affixed to a half-life-increasing moiety, so as to thereby treat the subject.

This invention also provides a method for inhibiting angiogenesis in a subject comprising administering to the subject an effective amount of a composition of matter comprising the extracellular domain of a Notch receptor protein operably affixed to a half-life-increasing moiety, so as to thereby inhibit angiogenesis in the subject.

This invention further provides a composition of matter comprising the extracellular domain of Notch4 receptor protein operably affixed to a half-life-increasing moiety. In one embodiment, the extracellular domain is covalently bound to the half-life-increasing moiety. In another embodiment, the extracellular domain and the half-life-increasing moiety are within the same polypeptide chain.

This invention further provides a composition of matter comprising the extracellular domain of Notch4 receptor protein operably affixed to a half-life-increasing moiety and a pharmaceutically acceptable carrier.

This invention further provides an article of manufacture comprising (i) a packaging material having therein a composition of matter comprising the extracellular domain of a Notch receptor protein operably affixed to a half-life-increasing moiety and (ii) a label indicating that the composition is intended for use in treating a subject having a tumor or other disorder treatable by inhibiting angiogenesis in the subject.

This invention further provides a replicable vector which encodes a polypeptide comprising the extracellular domain of a Notch receptor protein operably affixed to a half-life-increasing moiety.

This invention further provides a host vector system which comprises a replicable vector which encodes a polypeptide comprising the extracellular domain of a Notch receptor protein operably affixed to a half-life-increasing moiety and a suitable host cell.

Finally, this invention provides a method of producing a polypeptide which comprises growing a host vector system which comprises a replicable vector which encodes a polypeptide comprising the extracellular domain of a Notch receptor protein operably affixed to a half-life-increasing moiety and a suitable host cell under conditions permitting production of the polypeptide, and recovering the polypeptide so produced.

Figure 1:
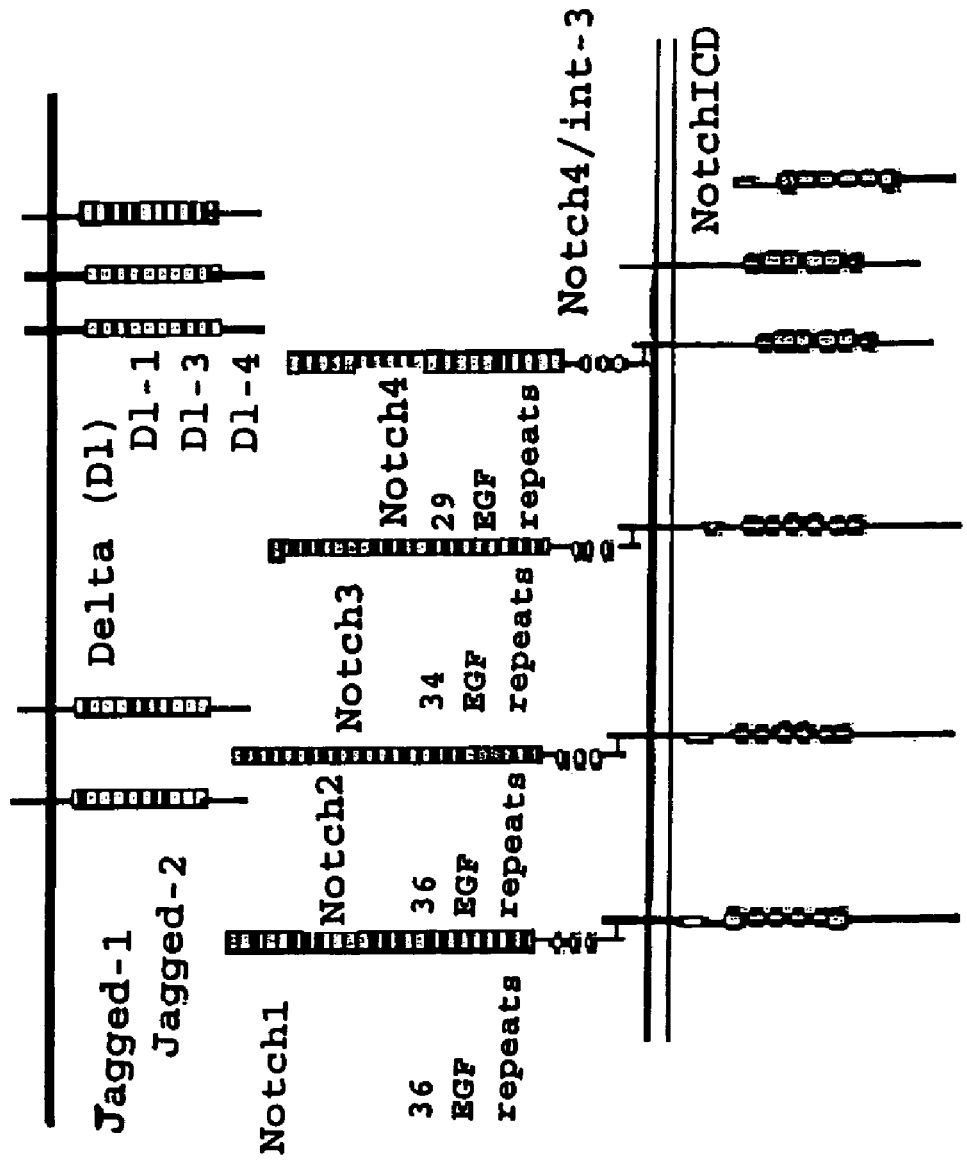
FIG. 1

This Figure shows the schematic structure of Notch and Notch ligands: Notch1, Notch2, Notch3, Notch4, Jagged-1, Jagged-2, Delta-like 1, Delta-like 3, Delta-like 4.

FIG. 2

This Figure shows the schematic design of Notch-based fusion proteins (NotchECD/Fc). The extracellular domain of Notch1, Notch2, Notch3, or Notch4 containing the EGF-repeats is fused to the Fc portion of an antibody.

FIG. 3

This Figure shows a co-culture assay for testing the activity of Notch-based fusion proteins. Notch and Notch responsive transcriptional reporters are expressed in a "Notch-responsive" cell, HeLa. Notch ligands, Jagged-1, Delta-like 1, or Delta-like 4 are expressed in a "ligand-presenting" cell, 293. Expression is mediated by transfection of individual cell populations, cells are co-cultured, and then assayed for Notch-dependent reporter activity.

FIG. 4

This Figure shows the inhibitory activity of Notch-based fusion protein against activation of Notch signaling by interaction between Notch and Notch ligand. Induction of Notch signaling was detected by co-cultivating both Notch1- and 3 types of Notch ligand-expressing cells and these inductions were inhibited by co-transfection of Notch-based fusion protein-expressing vector into Notch1-expressing cells. Therefore, Notch-based fusion proteins can be used as Notch inhibitor based on inhibition of interaction between Notch and Notch ligand.

FIG. 5

This Figure shows the expression of Notch1-based fusion protein (Notch1ECD/Fc) in 293. Panel A: expression in cell lystates (lys) or secreted into media (sup). Panel B: expression in 293 lysates of NECD/Fcs, as listed.

FIG. 6

This Figure shows activation of Notch signaling in HUVEC infected with adenoviral-encoding VEGF-165. Activation of Notch signaling can be detected by using CBF1 promoter activity. Transcriptional activity of CBF1 promoter is activated by binding of Notch-IC to CBF1. We measured CBF1 promoter activity in HUVEC which was infected with adenovirus-encoding VEGF-165 at different MOI. Induction of CBF1 promoter was clearly detected in Ad-VEGF-infected HUVEC, compared to Ad-LacZ-infected cells in the MOI dependent manner. This data showed overexpression of VEGF could activate Notch signaling in HUVEC.

FIG. 7

This Figure shows the effect of Notch-based fusion proteins on VEGF-induced activation of Notch signaling. Co-infection of Ad-Notch-based fusion protein with Ad-VEGF clearly reduced activation of CBF1 promoter activity induced by Ad-VEGF infection alone. In the case of infection at 40 MOI for each adenovirus in panel A, 60% inhibition at 24 hour and 90% inhibition at 48 hour after reporter gene transfection was detected. This inhibitory activity of Notch trap was dependent on MOI of Ad-Notch-based fusion protein.

FIG. 8

This Figure shows an experiment in which we evaluated the effect of Notch-based fusion proteins on induction of budding by overexpressed VEGF-165 in HUVEC. When Ad-VEGF-infected HUVEC were cultured on type collagen gel for 8 days, budding was induced into collagen gel. This induction of budding by overexpressed VEGF was clearly inhibited by coinfection of adenoviral-encoding Notch-based fusion proteins. Ad-Notch-based fusion protein itself had less effect on morphology.

FIG. 9

This Figure shows the result of counting buds per field under microscope. Ad-VEGF-infection into HUVEC increased the number of buds depending on used MOI. Even though a half MOI of Notch-based fusion protein was used, compared to Ad-VEGF, Ad-VEGF-induced budding was clearly inhibited. These data suggested that VEGF induced budding of HUVEC through activation of Notch signaling and Notch-based fusion protein could inhibit VEGF-induced budding.

FIG. 10

This Figure shows the amino acid sequence of the extracellular domain of the rat Notch1 protein (SEQ ID NO:1) and a linker sequence (SEQ ID NO:2).

FIG. 11

This Figure shows the amino acid sequence of the extracellular domain of the rat Notch2 protein (SEQ ID NO:3) and a linker sequence (SEQ ID NO:2).

FIG. 12

This Figure shows the amino acid sequence of the extracellular domain of the mouse Notch3 protein (SEQ ID NO:4).

FIG. 13

This Figure shows the amino acid sequence of the extracellular domain of the mouse Notch4 protein (SEQ ID NO:5) and a linker sequence (SEQ ID NO:2).

FIGS. 14A and 14B

This Figure shows the nucleic acid sequence of the extracellular domain of the rat Notch1 gene (SEQ ID NO:6).

FIGS. 15A and 15B

This Figure shows the nucleic acid sequence of the extracellular domain of the rat Notch2 gene (SEQ ID NO:7).

FIGS. 16A and 16B

This Figure shows the nucleic acid sequence of the extracellular domain of the mouse Notch3 gene (SEQ ID NO:8).

FIGS. 17A and 17B

This Figure shows the nucleic acid sequence of the extracellular domain of the mouse Notch4 gene (SEQ ID NO:9) and the nucleic acid sequence (SEQ ID NO:10) and the amino acid sequence (SEQ ID NO:2) of a linker sequence.

FIGS. 18A and 18B

This Figure shows the nucleic acid sequence of the extracellular domain of the human Notch1 gene (SEQ ID NO:11).

FIGS. 19A and 19B

This Figure shows the nucleic acid sequence of the extracellular domain of the human Notch2 gene (SEQ ID NO:12).

FIGS. 20A and 20B

This Figure shows the nucleic acid sequence of the extracellular domain of the human Notch3 gene (SEQ ID NO:13).

FIGS. 21A and 21B

This Figure shows the nucleic acid sequence of the extracellular domain of the human Notch4 gene (SEQ ID NO:14).

FIGS. 22A-22I

Figure 22A:
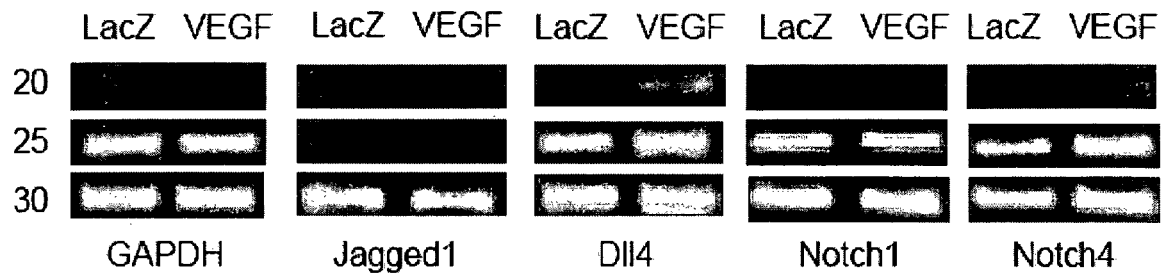
Figure 22B:
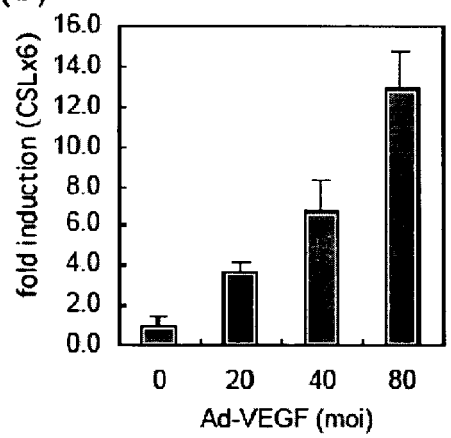
Figure 22C:
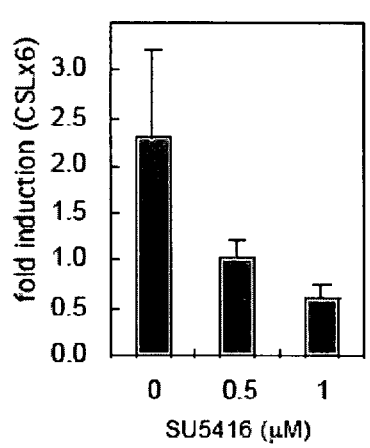
Figure 22D:
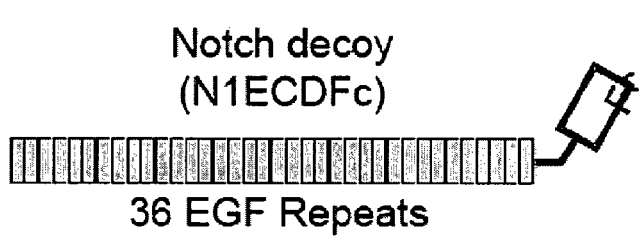
Figure 22E:
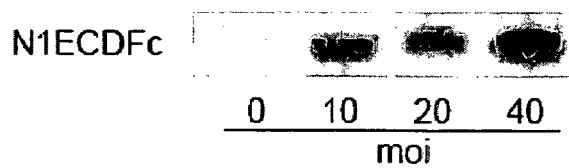
Figure 22G:
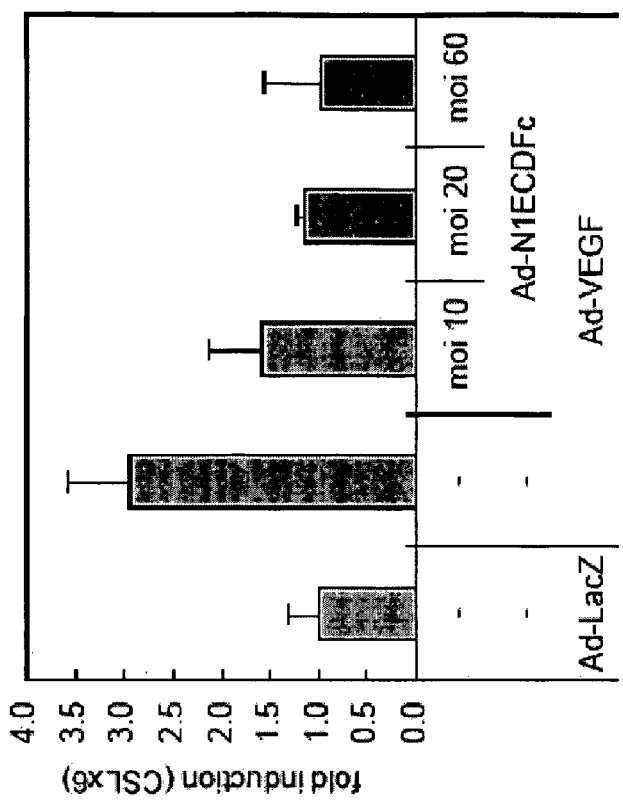
Figure 22F:
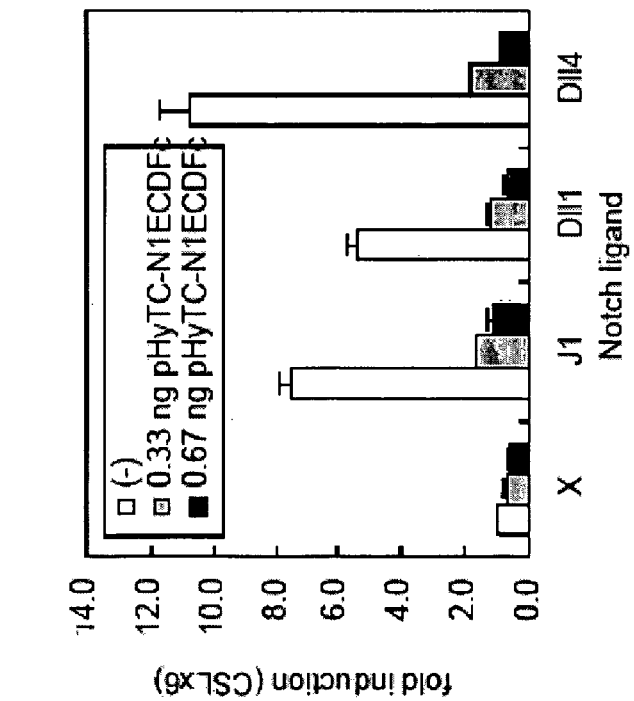
Figure 22I:
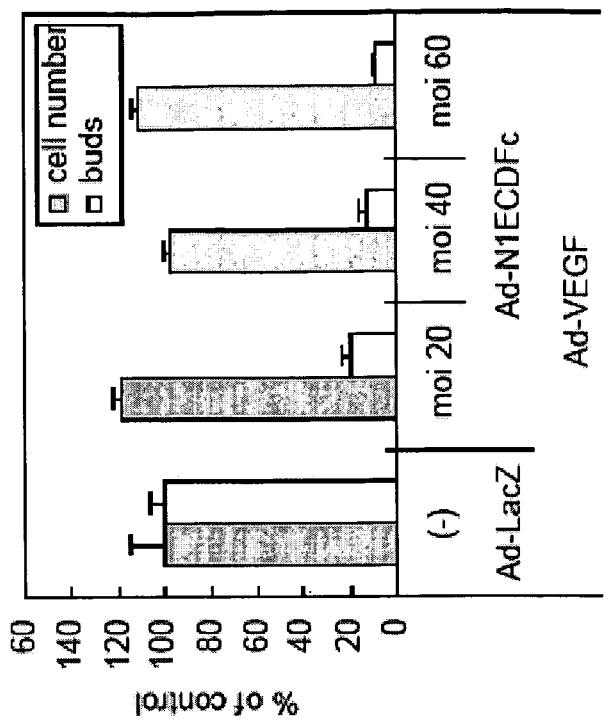
Figure 22H:
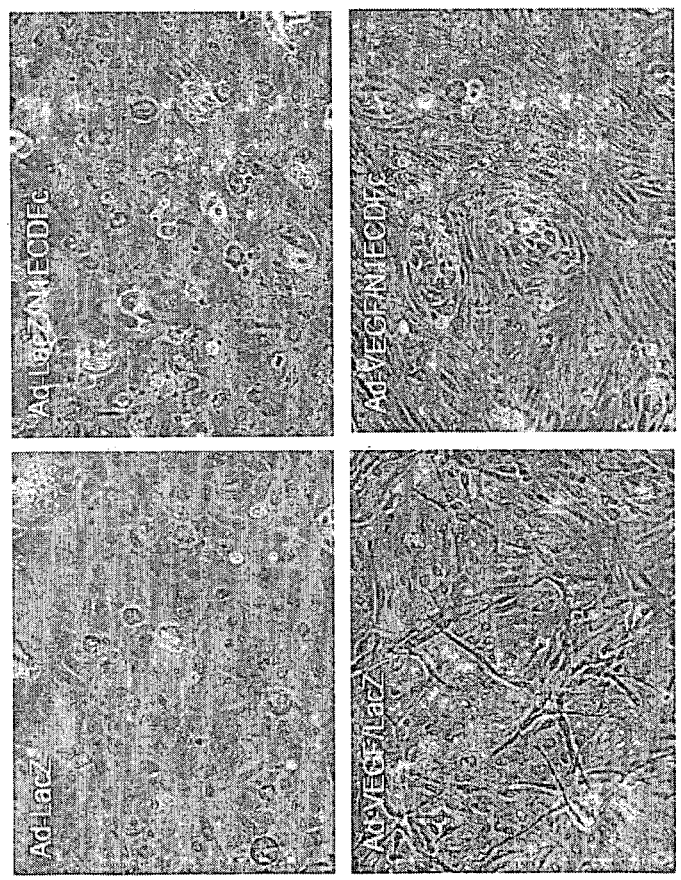

These Figures show that VEGF activates Notch signaling to induce HUVEC budding. HUVEC were transduced with Ad-VEGF at 40 MOI (FIGS. 22A, 22H, 22I) or 20 MOI (FIGS. 22C, 22G). Ad-LacZ was co-transduced to HUVEC to make the same total amount of adenovirus 60 MOI (FIG. 22G), 80 MOI (FIG. 22A) and 100 MOI (FIGS. 22H, 22I). FIG. 22A shows RT-PCR analysis of Notch and Notch ligand expression. Numbers show PCR cycles. FIG. 22B shows the effect of transduced VEGF on CSL reporter activity. FIG. 22C shows the effect of SU5416 on CSL reporter activity transactivated by Ad-VEGF. FIG. 22D shows the construct of Notch decoy (N1ECDFc). FIG. 22E shows secretion of N1ECDFc from HUVEC trasduced with Ad-N1ECDFc. FIG. 22F shows the effect of N1ECDFc against ligand-induced CSL reporter activity in a co-culture assay (□: (-); ■: 0.33 ng pHyTC-N1ECDFc; ■: 0.67 ng pHyTC-N1ECDFc). FIGS. 22G-I show the effect of N1ECDFc against Ad-VEGF-transduced HUVEC. Notch signaling was activated with transduction of Ad-VEGF in HUVEC in the absence or presence of co-transduction of Ad-N1ECDFc at indicated dosage. FIG. 22G shows the effect of N1ECDFc on CSL reporter activity transactivated by Ad-VEGF. FIG. 22H shows inhibition of budding of Ad-VEGF-transduced HUVEC with co-transduction of Ad-N1ECDFc at 40 MOI. FIG. 22I shows quantification of the effect of N1ECDFc on budding of Ad-VEGF-transduced HUVEC (□: bud; ■: cell number).

FIGS. 23A-23J

Figure 23A:
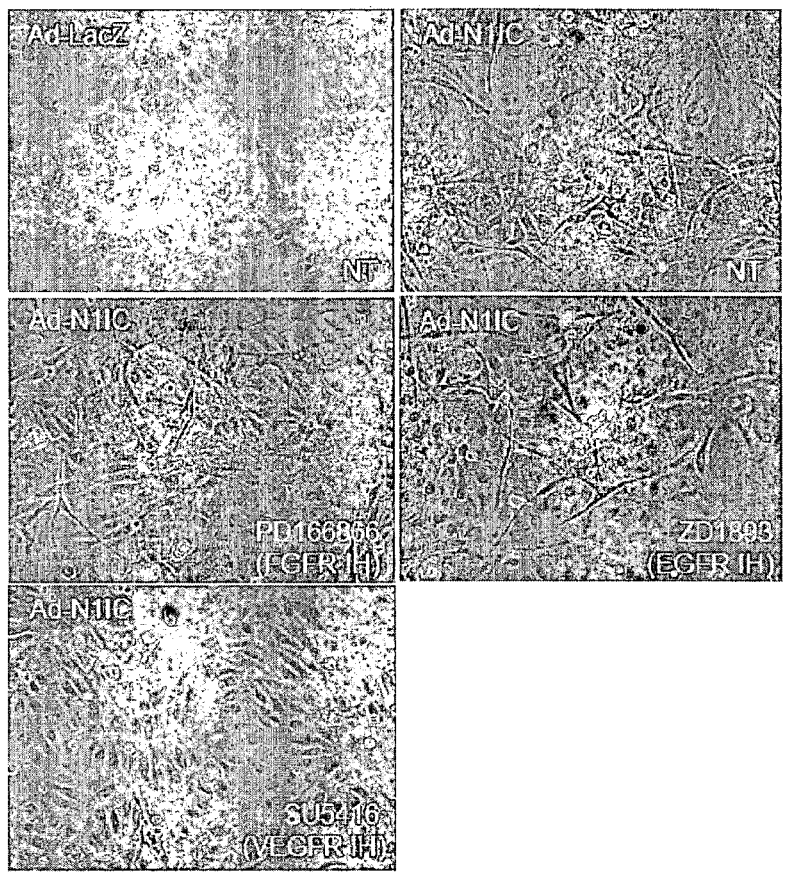
Figure 23B:
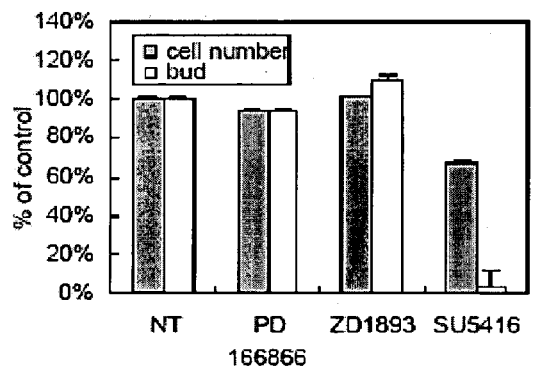
Figure 23C:
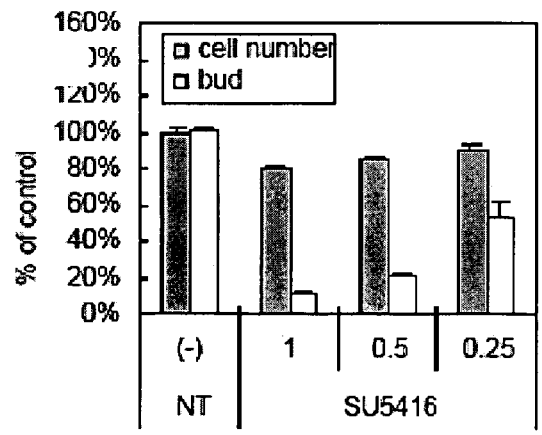
Figure 23D:
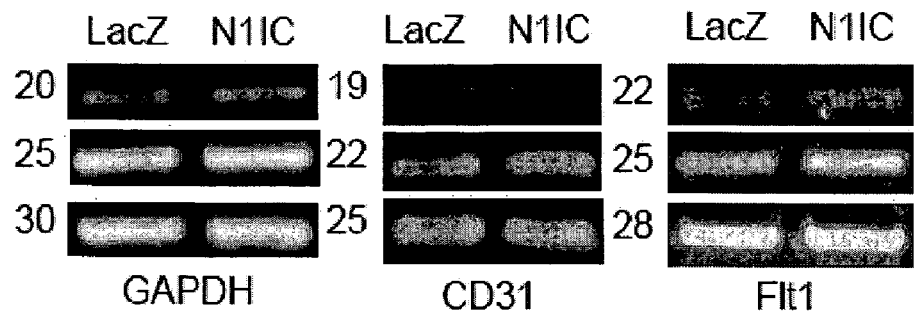
Figure 23E:
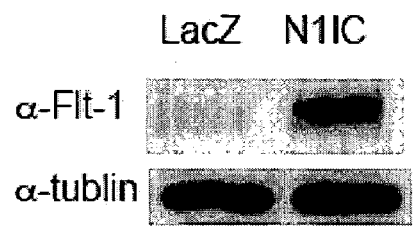
Figure 23F:
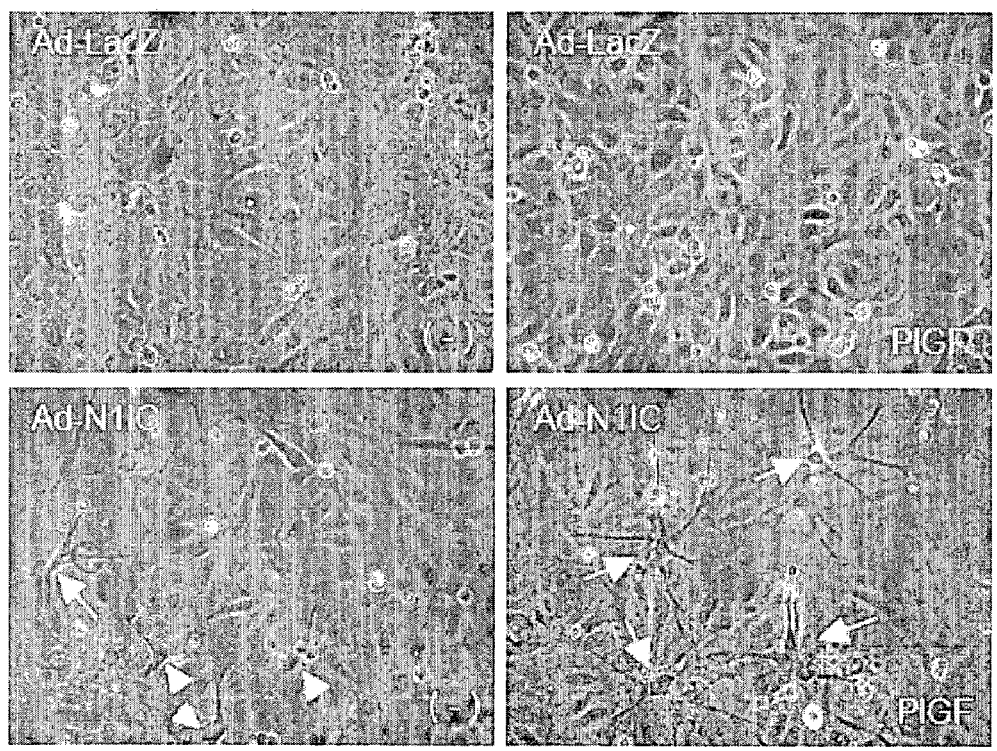

These Figures show that Notch signaling up-regulates Flt1 expression to induce HUVEC budding. HUVEC were transduced with either Ad-LacZ or Ad-N1IC at 40 MOI. FIGS. 23A-23C show the effect of inhibitors for receptor tyrosine kinases on Notch-induced HUVEC budding. FIG. 23A is a photograph of budding of Ad-N1IC-transduced HUVEC treated with PD166866, ZD1893 at 1 μM and SU5416 at 0.5 μM. FIG. 23B shows quantification of the effect of inhibitors at 1 μM (□: bud; ■: cell number). FIG. 23C shows dose-dependency of the effect of SU5416 (□: bud; ■: cell number). FIGS. 23D-E show induction of Flt-1 expression in Ad-N1IC-transduced HUVEC. FIG. 23D shows RT-PCR analysis of Flt-1 mRNA expression. FIG. 23E shows W.B. analysis of Flt-1 protein expression. FIGS. 23F-G show promotion of Notch-induced HUVEC budding with PlGF stimulation. Ad-N1IC-transduced HUVEC were cultured on collagen gel with SFM, instead of complete medium, in the absence or presence of 50 ng/ml PlGF. FIG. 23F shows PlGF-induced budding of Ad-N1IC-transduced HUVEC (arrow head: buds with single filopodia; arrow: buds with multiple filopodia). FIG. 23G shows the quantification of the effect of PlGF on budding of Ad-N1IC-transduced HUVEC (□: multi; ■: total). FIGS. 23H-I show the effect of Flt-1 siRNA transfection on Flt1 expression. Ad-N1IC-transduced HUVEC were transfected with 200 pmol of either control (CT) or Flt-1 siRNA. FIG. 23H shows the reduction of Flt-1 mRNA expression. FIG. 23I shows the reduction of Flt-1 protein expression. FIG. 23J shows the effect of Flt-1 siRNA transfection on Notch-induced HUVEC budding. Ad-N1IC-transduced HUVEC were transfected with either 100 or 200 pmol of siRNA and cultured on collagen gel for 2 days.

FIGS. 24A-24E

Figure 24A:
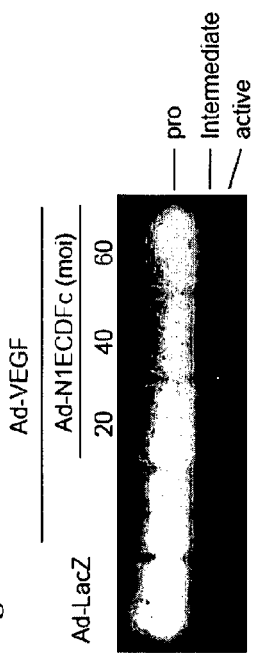
Figure 24B:
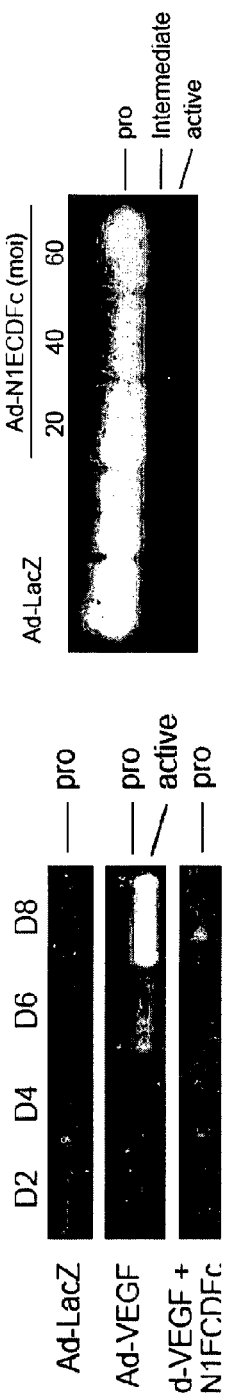
Figure 24D:
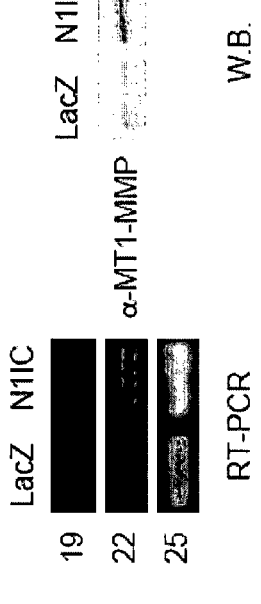
Figure 24C:
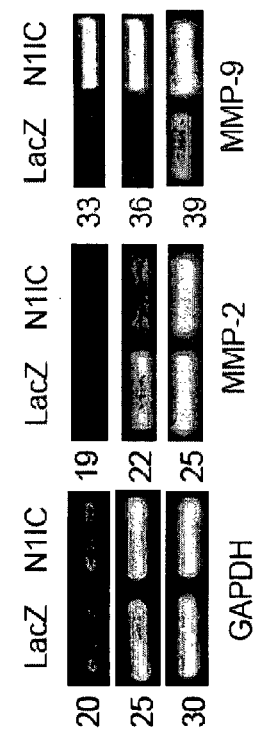
Figure 24E:
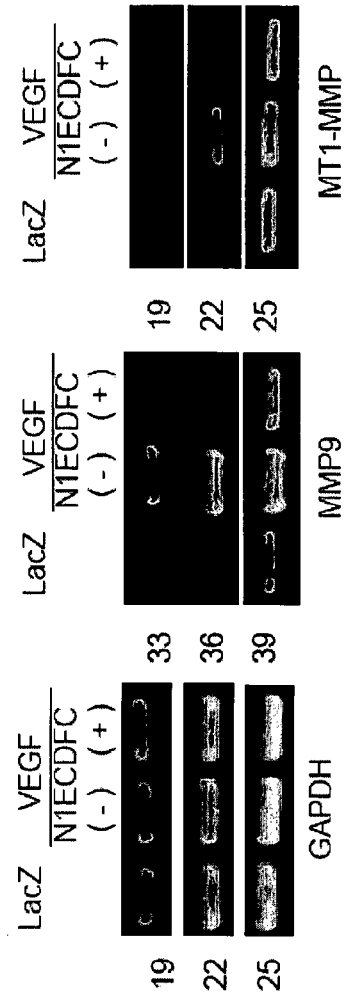

These Figures show that VEGF regulates gelatinase activity via Notch signaling by up-regulation of both MMP-9 and MT1-MMP. FIGS. 24A-B show gelatin zymography analysis of MMP-9 and MMP-2 activity stimulated by VEGF in HUVEC. FIG. 24A shows the effect of N1ECDFc on MMP-9 activity. Transduced HUVEC were cultured on fibrin gel on the indicated day (i.e. D2, D4, D6, D8). Similar results were also obtained by using collagen gel, although induction of MMP-9 was stronger on fibrin gel than collagen gel (data not shown). FIG. 24B shows the effect of N1ECDFc on MMP-2 activity. HUVEC were transduced with Ad-N1ECDFc at the indicated doses and condition medium was collected from HUVEC cultured on collagen gel at day 4. FIGS. 24C-D show up-regulation of MMP-9 and MT1-MMP with Notch signaling. HUVEC were transduced with either Ad-LacZ or Ad-N1IC at 40 MOI. Numbers show PCR cycles. FIG. 24C shows RT-PCR analysis of the effect of Notch signaling on expression of MMP-9 and MMP-2. FIG. 24D shows the induction of MT1-MMP expression of both transcript and protein with Notch signaling. FIG. 24E shows RT-PCR analysis of MMP-9 and MT1-MMP expression in Ad-VEGF-HUVEC with co-transduction of Ad-N1ECDFc. HUVEC were transduced with Ad-VEGF in the absence or presence of co-transduction of Ad-N1ECDFc at 40 MOI each. Ad-LacZ was co-transduced to make the same total amount of adenovirus at 80 MOI.

FIGS. 25A-25D

Figure 25A:
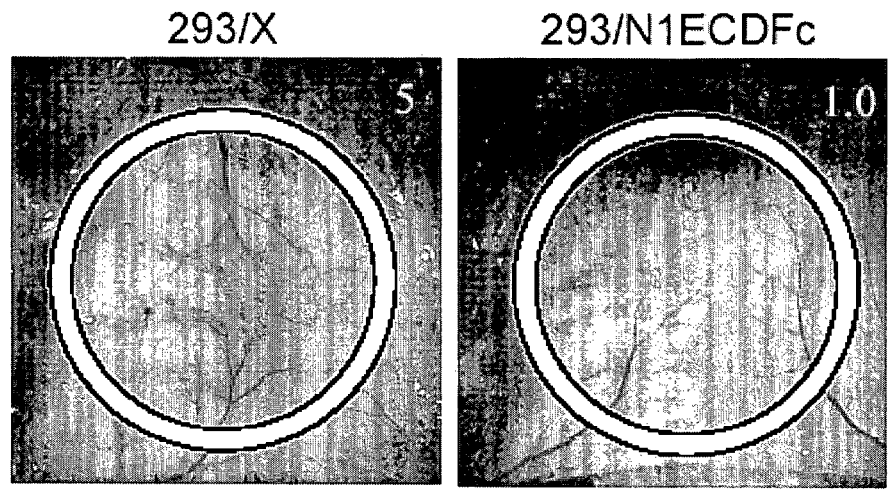
Figure 25:
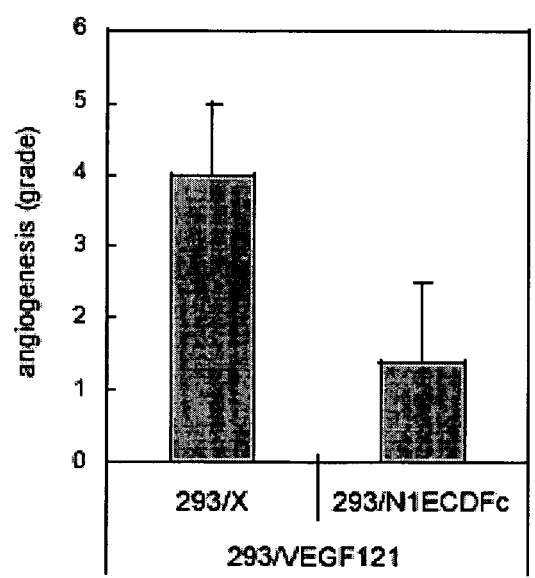
Figure 25C:
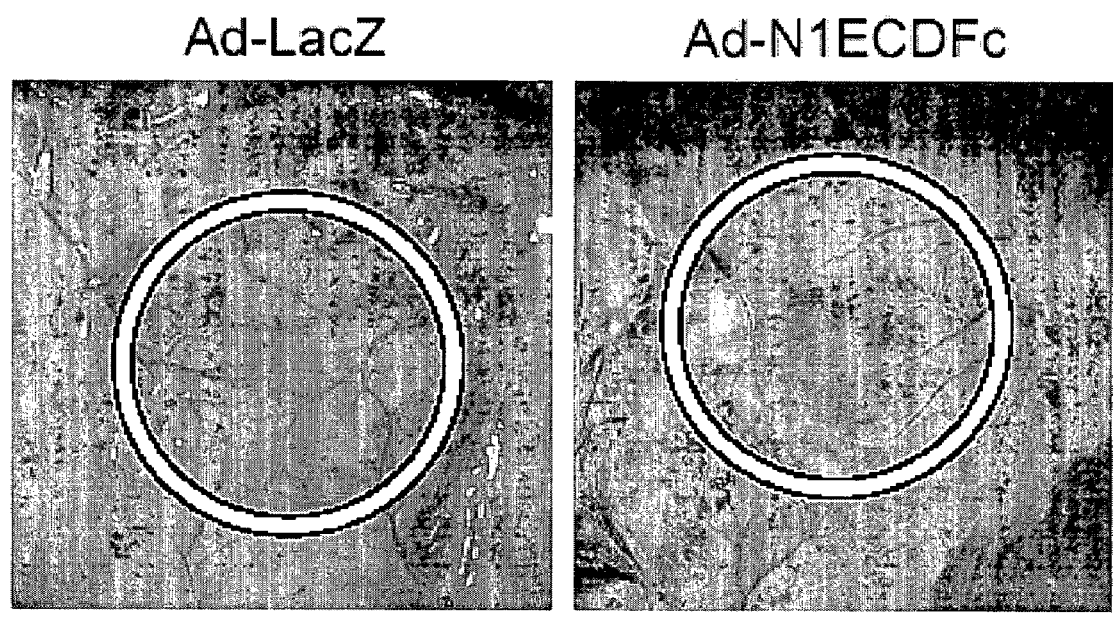
Figure 25D:
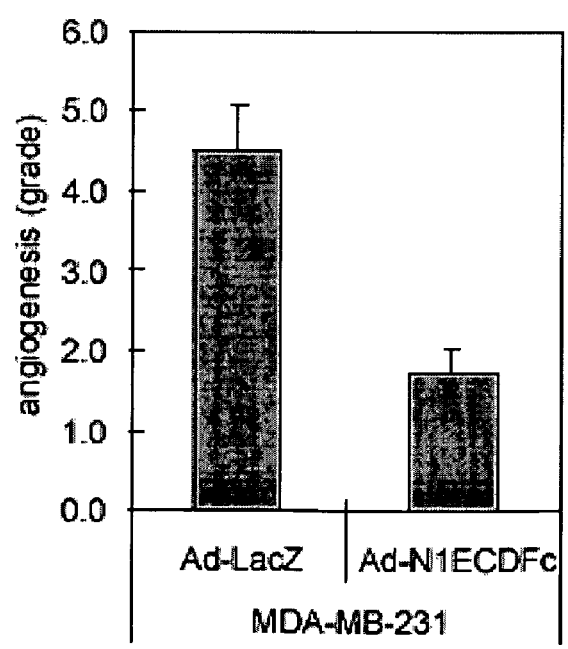

These Figures show the role of Notch signaling in VEGF-dependent in vivo angiogenesis. FIGS. 25A-25D show inhibition of VEGF-induced angiogenesis with N1ECDFc in mouse DAS assay. Representative photographs are shown. FIG. 25A show subcutaneous induced angiogenesis with 293/VEGF transfectant versus 293/VEGF also expressing Notch decoy (Notch-based fusion protein) N1ECDFc. FIG. 25B shows the quantitation of degree of vascularization induced by 293/VEGF in control versus 293 expressing Notch decoy (Notch-based fusion protein)—N1ECDFc. FIG. 25C shows subcutaneous induced angiogenesis with Ad-LacZ infected MDA-MB-231 cells versus Ad-N1ECDFc (Notch-based fusion protein) infected MDA-MB-231 cells. MDA-MB-231 breast cancer cells produce VEGF (data not shown). FIG. 25D shows quantitation of degree of vascularization induced by Ad-LacZ infected MDA-MB-231 cells versus Ad-N1ECDFc (Notch-based fusion protein) infected MDA-MB-231 cells.

Figure 26A:
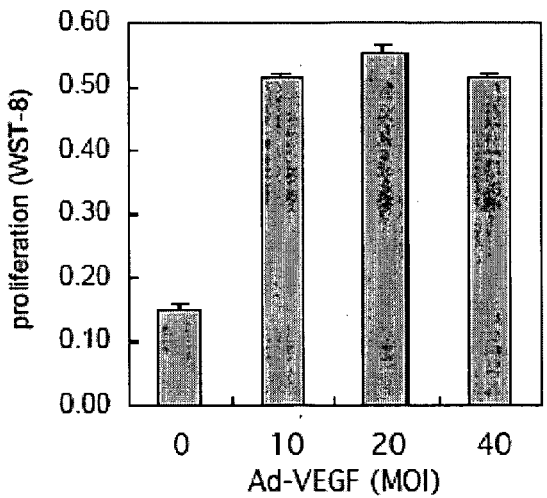
Figure 26B:
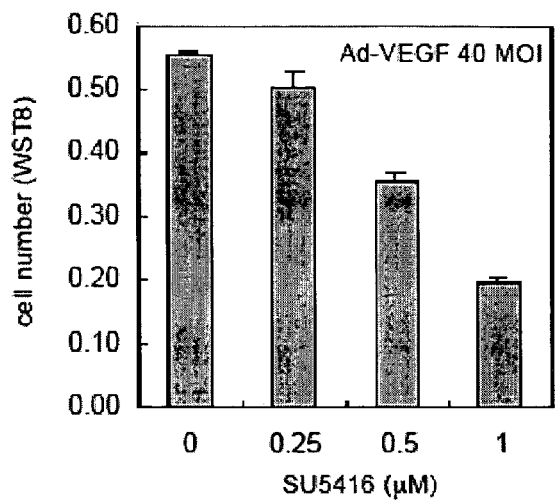

FIGS. 26A and 26B

These Figures show proliferation of Ad-VEGF165-transduced HUVEC. HUVEC were transduced with Ad-VEGF165 at the indicated dosages. Ad-LacZ was also co-infected to make the same total amount of adenovirus at a MOI of 40 pfu/cell. HUVEC were suspended in SFM supplemented with 1% FBS and then plated at $1 \times 10^4$ cells/well in 24-well multi-wll plates with 0.4 ml of medium. After 4 days, cell numbers were determined using the CCK-8 kit and the results are indicated as the ratio of cell numbers determined to the number of control cells, which were transduced with Ad-GFP at a MOI of 40 pfu/cell. Figure 26A shows the effect of transduced VEGF on proliferation. FIG. 26B shows the inhibitory effect of SU5416. Ad-VEGF-transduced HUVEC were treated with SU5416 at the indicated dosages.

Figure 27A:
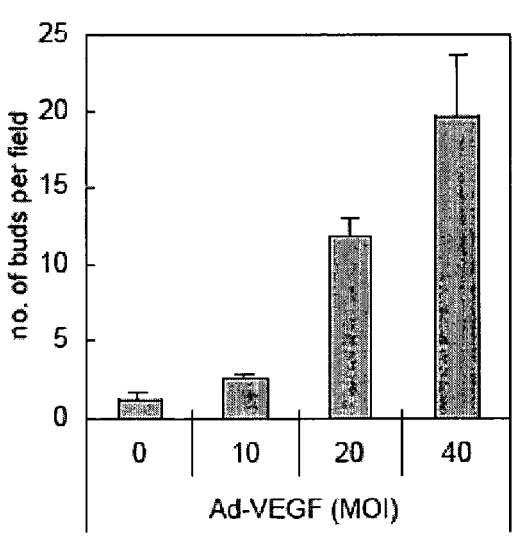
Figure 27B:
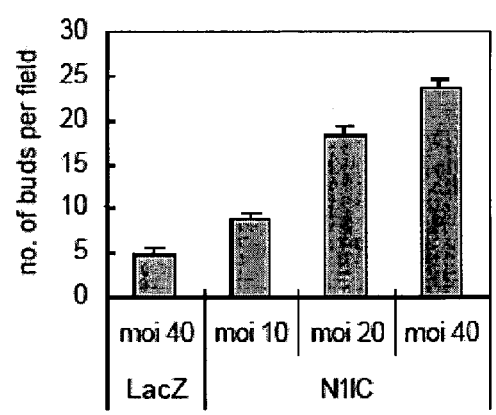

FIGS. 27A and 27B

These Figures show the induction of HUVEC buds on type I collagen gel. HUVEC were transduced with either Ad-VEGF165 or AD-N1IC at the indicated dosages. Ad-LacZ was also co-infected to make the same total amount of adenovirus at a MOI of 40 pfu/cell. Transduced HUVEC were cultured on collagen gel with complete medium. The amount of budding was evaluated under microscopy at day 7.

FIGS. 28A and 28B

These Figures show the effect of alteration of Notch signaling on cell proliferation. The cells were transduced with the indicated adenoviruses. Ad-GFP was also co-infected to make the same total amount of adenovirus at a MOI of 60 pfu/cell. After 4 days, cell numbers were determined using the CCK-8 kit and results are indicated as the ratio of cell numbers determined to the number of control cells, which were transduced with AD-GFP at MOI of 60 pfu/cell. FIG.

28A shows the effect of transduced N1IC and Notch fusion protein on the proliferation of HUVEC. Transduced HUVEC were suspended in complete medium and then plated at 1×10$^4$ cells/well in 24-well multiwell plates with 0.4 ml of indicated medium (☐: Ad-N1IC; ■: Ad-N1ECDFc). FIG. 28B shows the effect of Notch fusion protein on proliferation of KP1/VEGF transfectants. Transduced KP1/VEGF transfectants were suspended in RPMI1640 medium and then plated at 2×10$^4$ cells/well in 24-well multiwell plates with 0.5 ml of medium.

FIG. 29

This Figure shows the RT-PCR analysis of induction of PlGF expression in Ad-N1IC-transduced HUVEC. HUVEC were infected with either Ad-LacZ or Ad-N1IC at a MOI of 40 pfu/cell. Total RNA was isolated from transduced HUVEC cultured on collagen gel for 5 days with complete medium.

FIGS. 30A-30C

Figure 30A:
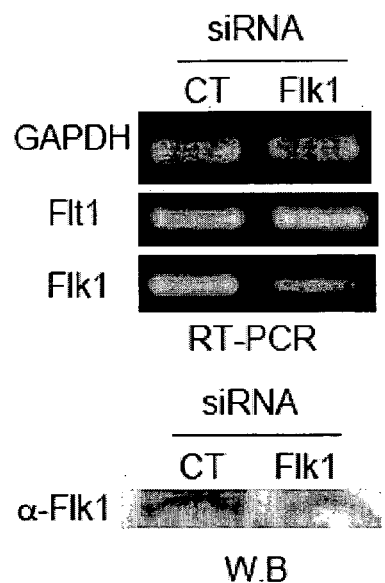
Figure 30B:
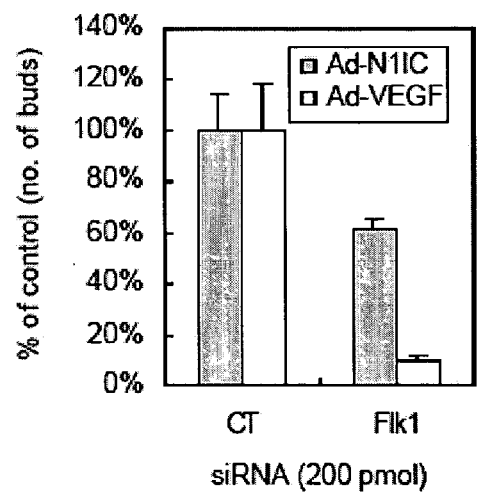
Figure 30C:
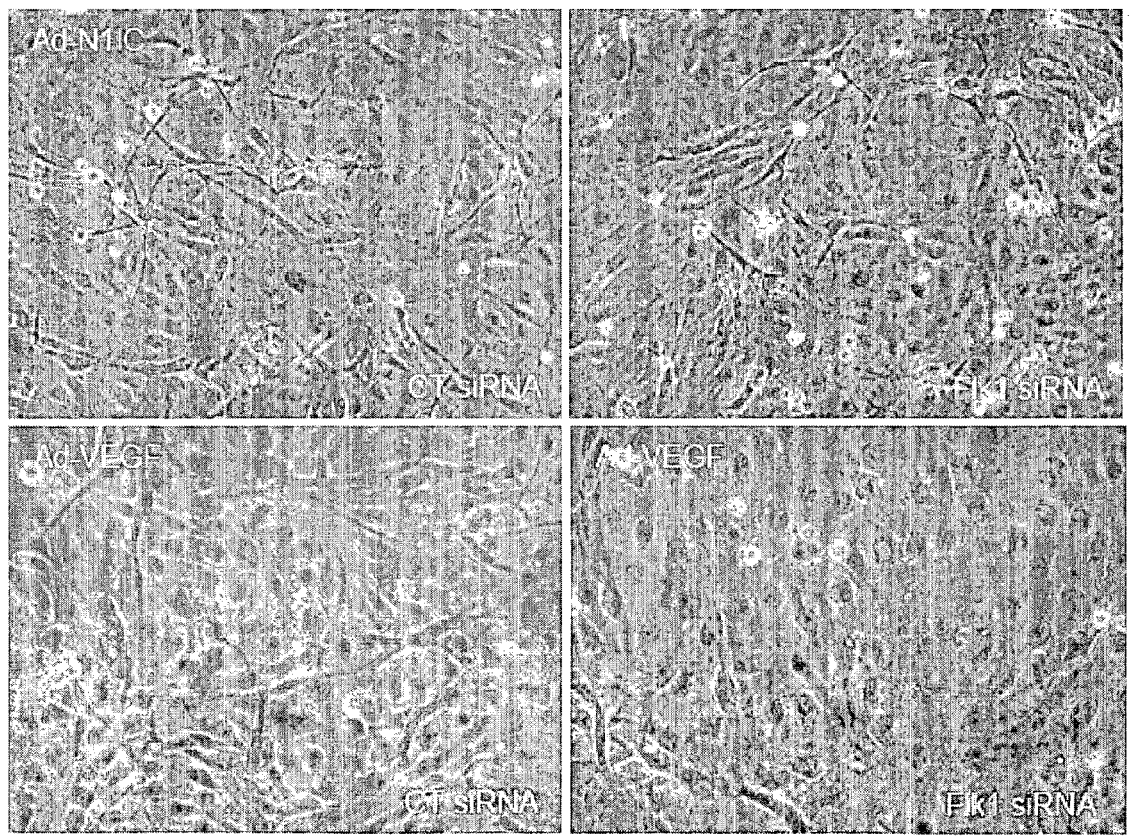

These Figures show inhibition of budding of either Ad-N1IC- or Ad-VEGF-transduced HUVEC with Flk-1 siRNA transfection. FIG. 30A shows reduction of Flk-1 mRNA and protein expression in Ad-VEGF-HUVEC with transfection of 200 pmol Flk-1 siRNA. Ad-VEGF-HUVEC at a MOI of 40 pfu/cell were transfected with 200 pmol of either control (CT) or Flk-1 siRNA. Total RNA was isolated 48 hours after transfection. Total cell lysate was collected from serum starved cells with SFM for 48 hours after transfection. FIGS. 30B and 30C show the inhibitory effect of Flk-1 siRNA transfection on either VEGF or Notch-induced HUVEC buds. Either Ad-N1IC- or Ad-VEGF-HUVEC at a MOI of 40 pfu/cell were transfected with 200 pmol of siRNA as indicated and cultured on collagen gel for 5 days. FIG. 30B shows the effect of Flk-1 siRNA transfection on HUVEC buds (☐: Ad-VEGF; ■: Ad-N1IC). FIG. 30C shows quantification of the inhibitory effect of Flk-1 siRNA transfection.

Figure 31A:
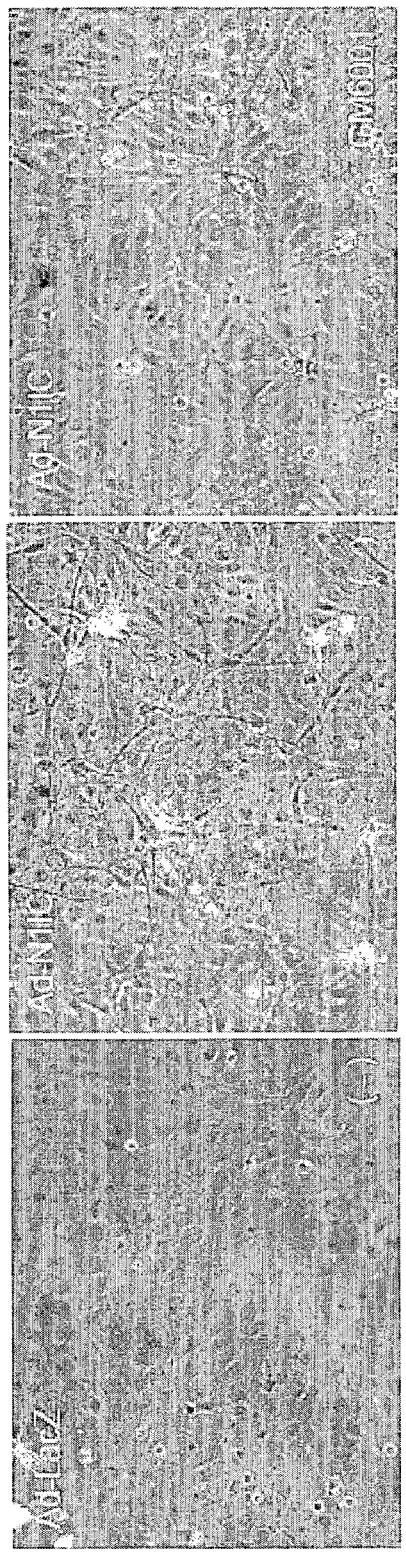
Figure 31B:
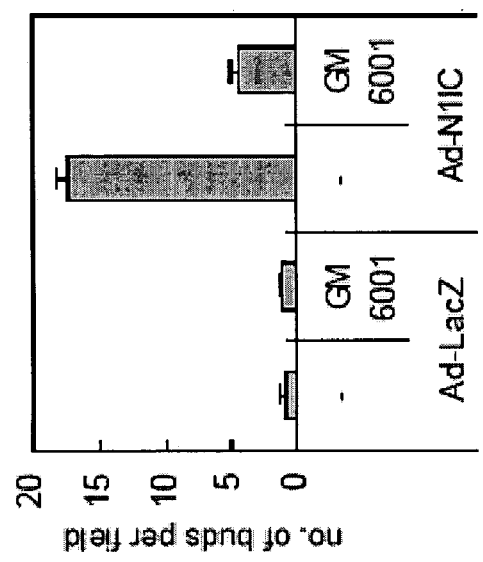

FIGS. 31A and 31B

These Figures show inhibition of budding of Ad-N1IC-transduced HUVEC with treatment of matrix metallo-proteinase inhibitor GM6001. Either Ad-LacZ or Ad-N1IC-HUVEC at a MOI of 40 pfu/cell were cultured on collagen gel for 5 days in the absence or presence of GM6001 at 50 μm. FIG. 31A shows the effect of GM6001 on Notch-induced HUVEC buds. FIG. 31B shows quantification of the inhibitory effect of GM6001.

DETAILED DESCRIPTION OF THE INVENTION

Terms

As used in this application, except as otherwise expressly provided herein, each of the following terms shall have the meaning set forth below.

"Administering" may be effected or performed using any of the methods known to one skilled in the art. The methods comprise, for example, intralesional, intramuscular, subcutaneous, intravenous, intraperitoneal, liposome-mediated, transmucosal, intestinal, topical, nasal, oral, anal, ocular or otic means of delivery.

"Affixed" shall mean attached by any means. In one embodiment, affixed means attached by a covalent bond. In another embodiment, affixed means attached non-covalently.

"Amino acid," "amino acid residue" and "residue" are used interchangeably herein to refer to an amino acid that is incorporated into a protein, polypeptide or peptide. The amino acid can be, for example, a naturally occurring amino acid or an analog of a natural amino acid that can function in a manner similar to that of the naturally occurring amino acid.

"Antibody" shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules may derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Nonhuman antibodies may be humanized by recombinant methods to reduce their immunogenicity in humans. Antibody fragments include, without limitation, Fab and Fc fragments. The "Fc portion of an antibody", in one embodiment, is a crystallizable fragment obtained by papain digestion of immunoglobulin that consists of the C-terminal half of two heavy chains linked by disulfide bonds and known as the "effector region" of the immunoglobulin. In another embodiment, "Fc portion of an antibody" means all, or substantially all, of one C-terminal half of a heavy chain.

"Humanized", with respect to an antibody, means an antibody wherein some, most or all of the amino acids outside the CDR region are replaced with corresponding amino acids derived from a human immunoglobulin molecule. Small additions, deletions, insertions, substitutions or modifications of amino acids are permissible as long as they do not abrogate the ability of the antibody to bind a given antigen. Suitable human immunoglobulin molecules include, without limitation, IgG1, IgG2, IgG3, IgG4, IgA and IgM molecules. Various publications describe how to make humanized antibodies, e.g., U.S. Pat. Nos. 4,816,567, 5,225,539, 5,585,089 and 5,693,761, and PCT International Publication No. WO 90/07861.

As used herein, the term "composition", as in pharmaceutical composition, is intended to encompass a product comprising the active ingredient(s) and the inert ingredient(s) that make up the carrier, as well as any product which results, directly or indirectly from combination, complexation, or aggregation of any two or more of the ingredients, or from dissociation of one or more of the ingredients, or from other types of reactions or interactions of one or more of the ingredients.

As used herein, "effective amount" refers to an amount which is capable of treating a subject having a tumor or inhibiting angiogenesis in a subject. Accordingly, the effective amount will vary with the subject being treated, as well as the condition to be treated. A person of ordinary skill in the art can perform routine titration experiments to determine such sufficient amount. The effective amount of a compound will vary depending on the subject and upon the particular route of administration used. Based upon the compound, the amount can be delivered continuously, such as by continuous pump, or at periodic intervals (for example, on one or more separate occasions). Desired time intervals of multiple amounts of a particular compound can be determined without undue experimentation by one skilled in the art. In one embodiment, the effective amount is between about 1 μg/kg-10 mg/kg. In another embodiment, the effective amount is beteen about 10 μg/kg-1 mg/kg. In a further embodiment, the effective amount is 100 μg/kg.

"Extracellular domain" as used in connection with Notch receptor protein means all or a portion of Notch which (i) exists extracellularly (i.e. exists neither as a transmembrane portion or an intracellular portion) and (ii) binds to extracellular ligands to which intact Notch receptor protein binds. The extracellular domain of Notch may optionally include a signal peptide. "Extracellular domain" and "ECD" are synonymous.

"Half-life-increasing moiety" means a moiety which, when operably affixed to a second moiety, increases the in vivo half-life of the second moiety. Half-life-increasing moieties include, for example, Fc portions of antibodies, glycosylation tags (i.e. glycosylated polypeptides), polyethylene glycol (PEG), polypeptides having PEG affixed thereto, and lipid-modified polypeptides.

"Inhibiting" the onset of a disorder or undesirable biological process shall mean either lessening the likelihood of the disorder's or process' onset, or preventing the onset of the disorder or process entirely. In the preferred embodiment, inhibiting the onset of a disorder or process means preventing its onset entirely.

"Notch", "Notch protein", and "Notch receptor protein" are synonymous. Notch amino acid sequences are known, e.g. Notch1 (rat); Notch2 (rat); Notch3 (mouse); and Notch4 (mouse). Notch nucleic acid sequences are also known, e.g. Notch1 (rat and human); Notch2 (rat and human); Notch3 (mouse and human); and Notch4 (mouse and human).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA). Nucleic acids include, without limitation, anti-sense molecules and catalytic nucleic acid molecules such as ribozymes and DNAzymes. Nucleic acids also include nucleic acids coding for peptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the peptide) which share some or all of the properties of the naturally-occurring forms.

"Operably affixed" means, with respect to a first moiety affixed to a second moiety, affixed in a manner permitting the first moiety to function (e.g. binding properties) as it would were it not so affixed.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "pharmaceutically acceptable carrier" means that the carrier is compatible with the other ingredients of the formulation and is not deleterious to the recipient thereof, and encompasses any of the standard pharmaceutically accepted carriers. Such carriers include, for example, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

"Subject" shall mean any organism including, without limitation, a mammal such as a mouse, a rat, a dog, a guinea pig, a ferret, a rabbit and a primate. In the preferred embodiment, the subject is a human being.

"Treating" means either slowing, stopping or reversing the progression of a disorder. As used herein, "treating" also means the amelioration of symptoms associated with the disorder.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The following abbreviations are used herein: ECD: extracellular domain; IC: intracellular domain; NECD/Fc: Notch-based fusion protein; N1: Notch1; N2: Notch2; N3: Notch3; N4: Notch4.

Embodiments of the Invention

This invention provides a first method for treating a subject having a tumor comprising administering to the subject an effective amount of a composition of matter comprising the extracellular domain of a Notch receptor protein operably affixed to a half-life-increasing moiety, so as to thereby treat the subject.

This invention also provides a second method for inhibiting angiogenesis in a subject comprising administering to the subject an effective amount of a composition of matter comprising the extracellular domain of a Notch receptor protein operably affixed to a half-life-increasing moiety, so as to thereby inhibit angiogenesis in the subject.

In a first embodiment of the above methods, the Notch receptor protein is Notch1 receptor protein. In one embodiment, the Notch1 receptor protein is human Notch1 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a second embodiment of the above methods, the Notch receptor protein is Notch2 receptor protein. In one embodiment, the Notch2 receptor protein is human Notch2 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a third embodiment of the above methods, the Notch receptor protein is Notch3 receptor protein. In one embodiment, the Notch3 receptor protein is human Notch3 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a fourth embodiment of the above methods, the Notch receptor protein is Notch4 receptor protein. In one embodiment, the Notch4 receptor protein is human Notch4 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a fifth embodiment of the above methods, the subject is a mammal. In one embodiment, the mammal is a human.

In a sixth embodiment of the above methods, the angiogenesis is tumor angiogenesis.

In a further embodiment of the second method, the subject has a tumor. In another embodiment, the subject is afflicted with a pathologic vascular hyperplasia. In one embodiment, the pathologic vascular hyperplasia is a benign hemagioma. In a further embodiment, the subject is afflicted with a lymphatic vascular proliferative disease.

This invention provides a first composition of matter comprising the extracellular domain of Notch4 receptor protein operably affixed to a half-life-increasing moiety. In one embodiment, the extracellular domain is covalently bound to the half-life-increasing moiety. In another embodiment, the extracellular domain and the half-life-increasing moiety are within the same polypeptide chain.

This invention also provides a second composition of matter comprising the extracellular domain of Notch4 receptor protein operably affixed to a half-life-increasing moiety and a pharmaceutically acceptable carrier.

This invention further provides an article of manufacture comprising (i) a packaging material having therein a composition of matter comprising the extracellular domain of a Notch receptor protein operably affixed to a half-life-increasing moiety and (ii) a label indicating that the composition is intended for use in treating a subject having a tumor or other disorder treatable by inhibiting angiogenesis in the subject.

In a first embodiment of the above article, the Notch receptor protein is Notch1 receptor protein. In one embodiment, the Notch1 receptor protein is human Notch1 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a second embodiment of the above article, the Notch receptor protein is Notch2 receptor protein. In one embodiment, the Notch2 receptor protein is human Notch2 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a third embodiment of the above article, the Notch receptor protein is Notch3 receptor protein. In one embodiment, the Notch3 receptor protein is human Notch3 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a fourth embodiment of the above article, the Notch receptor protein is Notch4 receptor protein. In one embodiment, the Notch4 receptor protein is human Notch4 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In another embodiment of the above article, the composition is admixed with a pharmaceutical carrier. In a final embodiment, the subject is a human.

This invention provides a replicable vector which encodes a polypeptide comprising the extracellular domain of a Notch4 receptor protein operably affixed to a half-life-increasing moiety. In one embodiment, the half-life-increasing moiety is an Fc portion of an antibody. In another embodiment, the vector includes, without limitation, a plasmid, a cosmid, a retrovirus, an adenovirus, a lambda phage or a YAC.

This invention also provides a host vector system which comprises a replicable vector which encodes a polypeptide comprising the extracellular domain of a Notch receptor protein operably affixed to a half-life-increasing moiety and a suitable host cell. In one embodiment, the host cell is a eukaryotic cell. In another embodiment, the eukaryotic cell is a CHO cell. In a another embodiment, the eukaryotic cell is a HeLa cell. In a further embodiment, the host cell is a bacterial cell.

Finally, this invention provides a third method of producing a polypeptide which comprises growing a host vector system which comprises a replicable vector which encodes a polypeptide comprising the extracellular domain of a Notch receptor protein operably affixed to a half-life-increasing moiety and a suitable host cell under conditions permitting production of the polypeptide, and recovering the polypeptide so produced.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

First Series of Experiments

Materials & Methods

Plasmid Constructs

Adenovirus constructs encoding LacZ, full-length Notch4, or the activated form of Notch4/int3 have been previously described (Shawber et al., 2003). An activated form of Notch1 cDNA fused in frame with 6 myc tags (Kopan et al., 1994) was cloned into the adenovirus expression vector, pAd-lox. Both VEGF165 and N1ECDFc was also cloned into the pAd-lox. Adenoviral stocks were generated and titered as previously described (Hardy et al., 1997). The retroviral expression vector pHyTc encoding either LacZ, the activated form of Notch4/int3, J1, Dll1 and Dll4 have been previously described (Uyttendaele et al., 2000, Shawber et al., 2003, Das et al., 2004 in print). Plasmids encoding the intracellular domain of Notch1 (bp 5479-7833, Genbank accession# X57405) and the extracellular domain of Dll4 (bp 1-1545, Genbank accession# AF253468, provided by Chiron) fused in frame with a myc/His tag, were engineered into pHyTC.

Notch1ECD, Notch2ECD, Notch3ECD and Notch4ECD are engineered into the Fc containing plasmid pCMX-sFR1-IgG using the methods set forth in *Clin. Exp. Immunol.* (1992) 87(1):105-110 to create the Notch-based fusion proteins, i.e. Notch1ECD/Fc, Notch2ECD/Fc, Notch3ECD/Fc and Notch4ECD/Fc.

Adenoviral Gene Transfer $7.5 \times 10^5$ cells of HUVEC at passage 3 were seeded into type I collagen-coated 6 well plates on the day before adenoviral infection. Adenoviral infection with Ad-lacZ, Ad-VEGF165 or Ad-N1ECDFc was performed at indicated m.o.i., and incubated at 37° C. for 1 hr with occasional swirling of plates.

Luciferase Reporter Assays

To determine ligand-induced Notch signaling, co-culture assays were performed using HeLa and 293-derived Bosc cells. Transient transfections were performed by calcium phosphate precipitation. Hela cells plated 1-day prior in 10-cm plates at $1.5 \times 10^6$ were transfected with 333 ng of pBOS Notch1, 333 ng pGA981-6, and 83 ng pLNC lacZ with either 666 ng pCMV-Fc or pHyTC-N1ECDFc (333 ng for x1, 666 ng for x2). Bosc cells plated 1-day prior in 10-cm plates at $4 \times 10^6$ were transfected with either 680 ng pHyTc-Jagged1, pHyTc-Dll1, pHyTc-Dll4, or pHyTc-x (empty vector). One day after transfection, the cells were co-cultured in triplicate (HeLa:Bosc, 1:2) on 12-well plates for 24 hours. Cells were harvested and luciferase activity was determined 2-days post-transfection using the Enhanced Luciferase assay kit (BD PharMingen), and β-galactosidase activity was determined using the Galacto-Light Plus kit (PE Biosystems). All assays were performed in a Berthold dual-injection luminometer.

To determine VEGF-induced Notch signaling, HUVEC which were infected with adenovirus were used. HUVEC plated 1-day prior in 6 well plates at $8.0 \times 10^5$ were infected with either Ad-LacZ as control or Ad-VEGF at indicated m.o.i. in the presence or absence of Ad-N1ECD/Fc. Two days after infection, infected HUVEC were re-seeded into 24-well plate at $1.5 \times 10^5$ cell in triplicate and cultured for 24 hours, and then transfected with 12.5 ng pRL-SV40 (Promega) and 137.5 ng pGA981-6 using Effectene transfection reagent (Qiagen). Cells were harvested either 1 or 2 days post-transfection and luciferase activity was determined by using the Dual-Luciferase® Reporter Assay System (Promega).

Sprouting Assay

For making collagen gels, an ice-cold solution of porcine type I collagen (Nitta gelatin, Tokyo, Japan) was mixed with 10×RPMI1640 medium and neutralization buffer at the ratio of 8:1:1. 400 μl aliquots of collagen gel were then added to 24-well plates and allowed to gel for at least 1 hour at 37° C. Following adenoviral infection (above), HUVEC was harvested and plated at $1.3 \times 10^5$ cells per well onto the top of the collagen gel in 24-well plates in 0.8 ml of EGM2 medium. HUVEC became nearly confluent 48 hours after plating. After seeding, medium was changed every 2 days for 1 week. Sprouting was observed and photographs taken after 8 days with an Olympus digital camera mounted to a microscope. For quantification of the number of sprouts, 5 fields per each well were randomly selected and sprouting was counted under microscopy in a blind manner by two investigators.

Results and Discussion

NOTCHECD/Fc Fusion Proteins Function as Antagonists of Notch

Notch Antagonists—NotchECD/Fc Fusion Proteins

Figure 2:
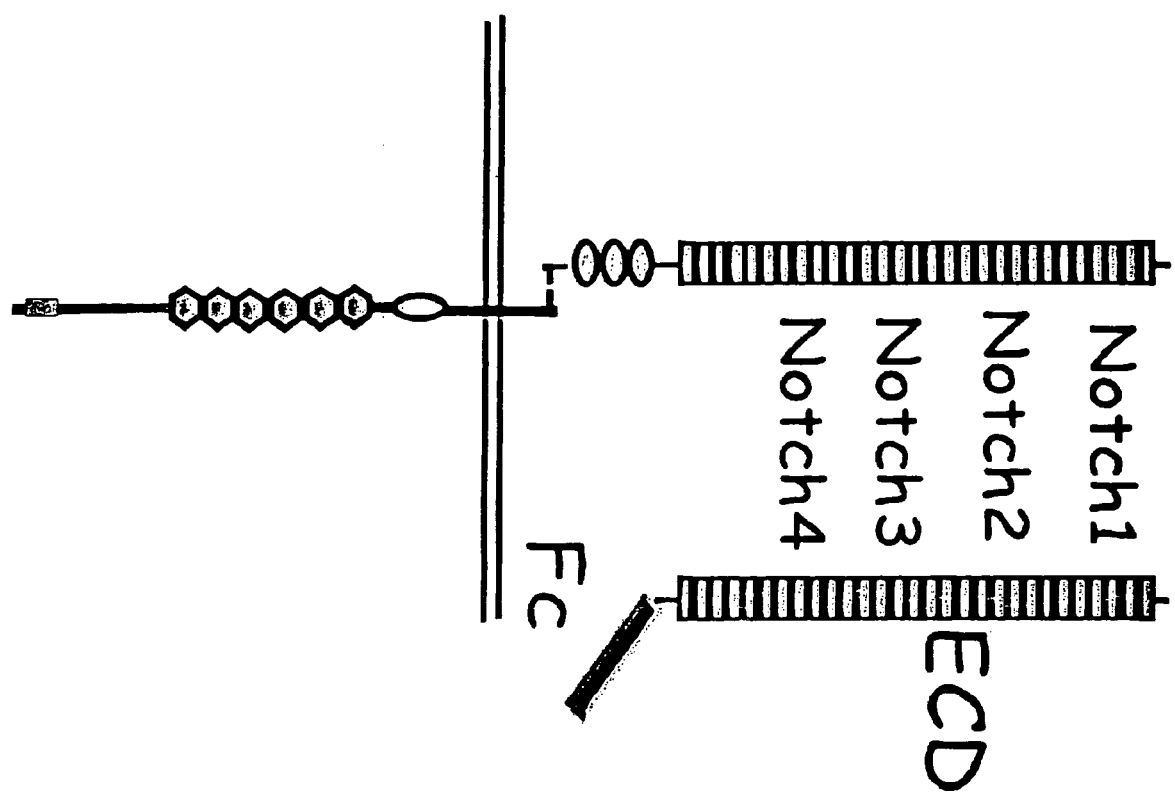

We have made several Notch antagonists (FIG. 2). Our strategy was to fuse the coding sequence of Notch EGF repeats in the Extracellular Domain (ECD) to the human or mouse Fc domain. This design makes a secreted protein without signaling function but which retains the ligand-binding domain and thus should bind to and inhibit ligand function. We refer to these proteins as "NotchECD/Fc" and all four Notch1-4ECD/Fcs have been made. The Fc domain facilitates affinity purification and protein detection by immunoblotting or immunohistochemistry.

Testing Notch Antagonists

Figure 3:
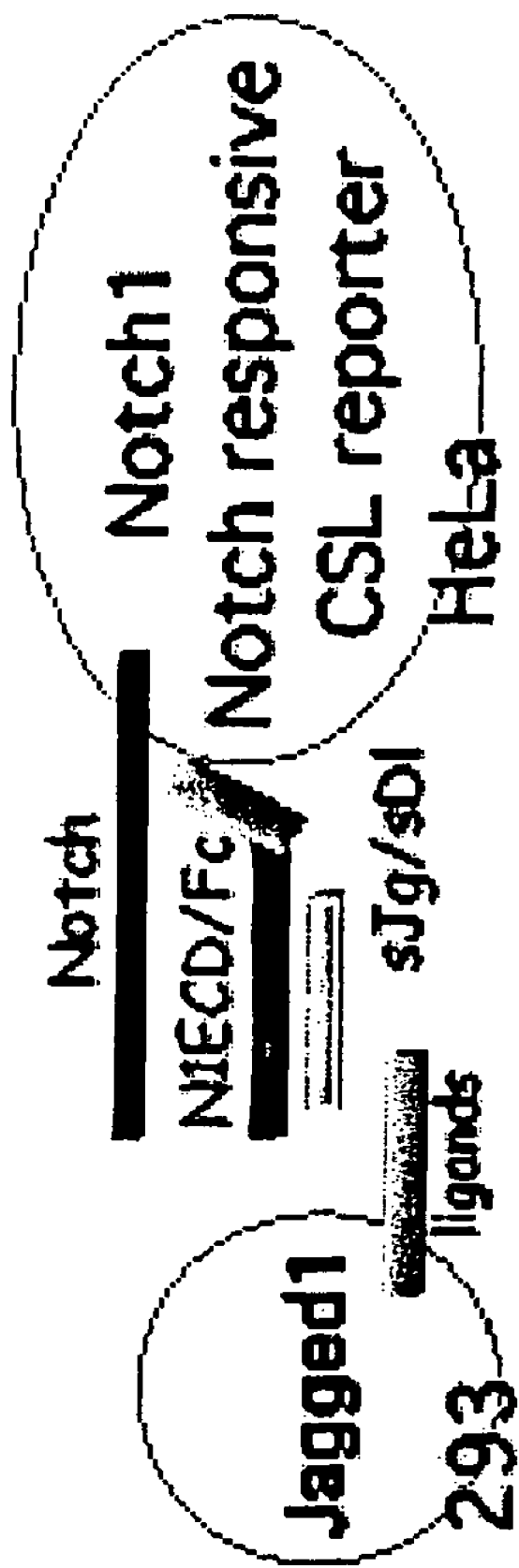
Figure 4:
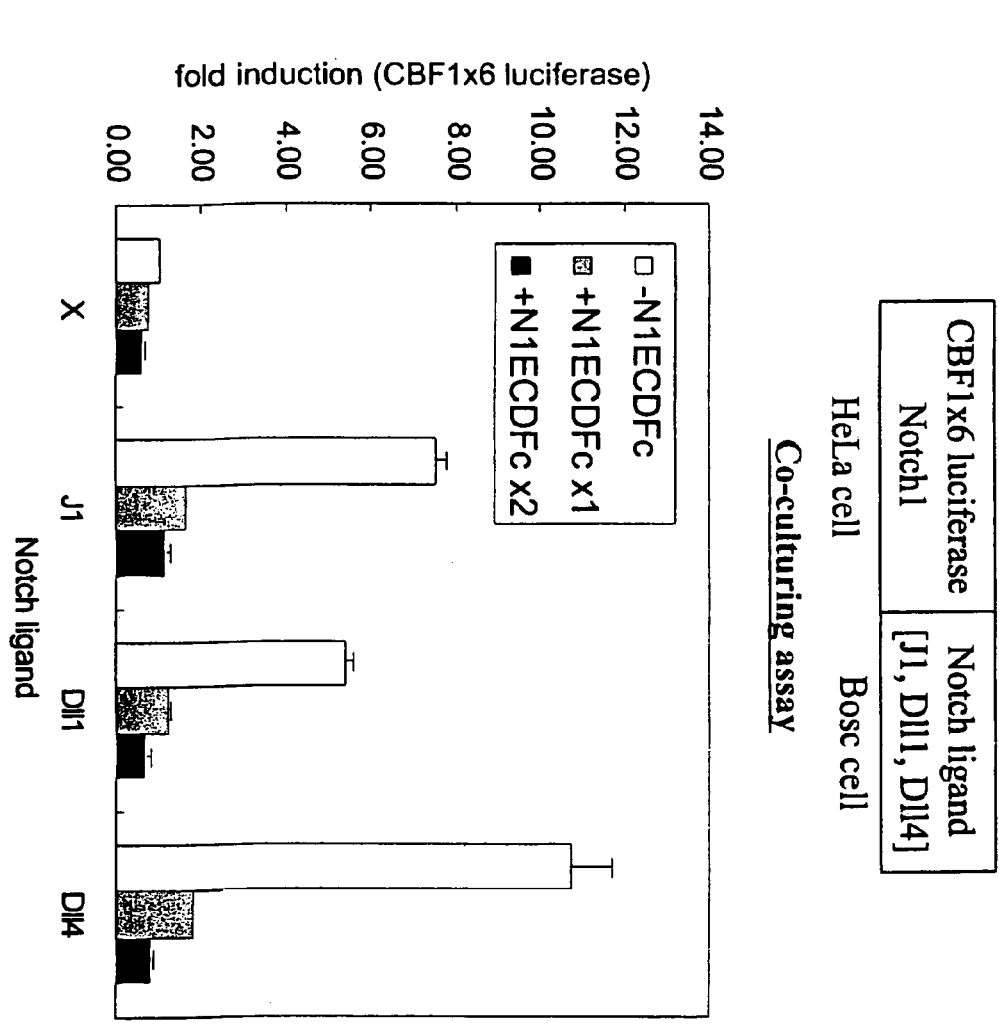

An in vitro co-culture system (FIG. 3) with ligands expressed on one cell and Notch receptor activation scored in another cell was used to measure transcriptional activation of the Notch pathway. We used this co-culture assay to show that Notch1ECD/Fc functions to block ligand-dependent Notch signaling (FIG. 4). The N1ECD/Fc expression vector was co-transfected at different ratios with full-length Notch1 and the CSL-luciferase reporter in HeLa cells, followed by co-culture with ligand expressing 293 cells. We observed that activation of Notch1 signaling by Notch ligands was reduced by N1ECD/Fc expression. This effect displayed concentration-dependency; a 2:1 ratio of N1ECD/Fc to Notch1 was more effective in inhibiting signaling than a 1:1 ratio. Notch1ECD/Fc could block signaling mediated by Jagged1, Delta-like 1 or Delta-like 4.

Expressing and Purifying Notch Antagonists

Figure 5:
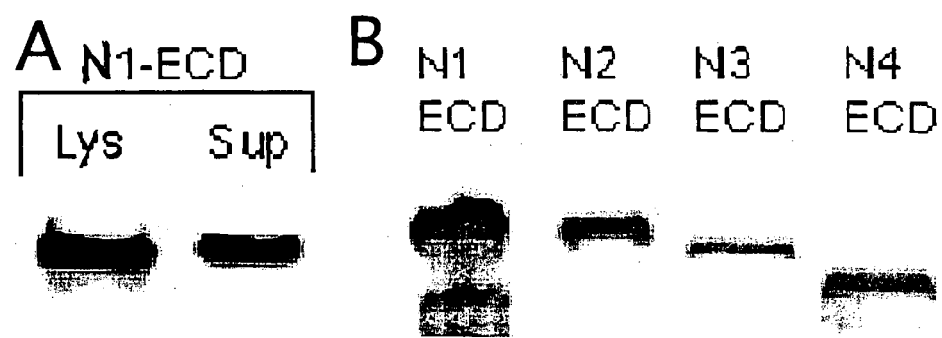

We have made CHO and HeLa cell lines expressing Notch-ECD/FCs using retroviral vectors for the purpose of protein purification. N1ECD/Fc proteins are secreted (FIG. 5); as shown in conditioned media collected from HeLa-Notch-ECD/Fc lines and purified with Protein-A(pA) agarose. The pA purified sample (Sup) and whole cell lysates (Lys) were immunoblotted with α-Fc antibody (FIG. 5, panel A) demonstrating that N1ECD/Fc is secreted into the media. Adenovirus vectors for NotchECD/Fc were used to infect HeLa cells and lysates from these cells were immunoblotted with α-Fc antibodies demonstrating that they express NotchECD/Fc(1, 2, 3, 4) proteins (FIG. 5, panel B). We are currently purifying N1ECD/Fc from CHO cell conditioned media using pA-affinity chromatography.

Defining Angiogenic Inhibition Using Notch Fusion Proteins

Activation of Notch signaling can be Detected by Using CBF1 Promoter Activity

Figure 6:
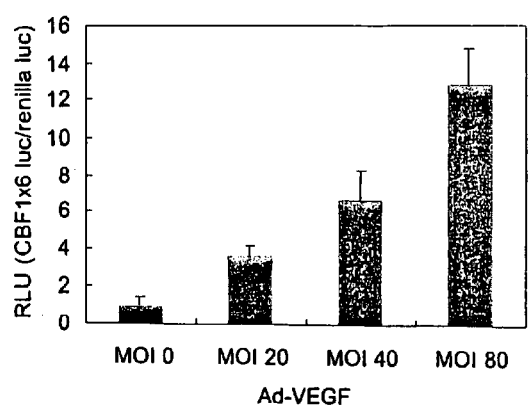

One can measure Notch signaling function by measuring transcriptional activity of CBF1 promoter, which is activated by binding of Notch-IC to CBF1. We measured CBF1 promoter activity in HUVEC which was infected with adenovirus encoding VEGF-165 at different MOI (FIG. 6). Induction of CBF1 promoter was clearly detected in Ad-VEGF-infected HUVEC, compared to Ad-LacZ-infected cells in the MOI dependent manner. This data showed over-expression of VEGF could activate Notch signaling in HUVEC. Thus VEGF induced Notch signaling activity.

We asked whether Notch fusion proteins could block VEGF-induced activation of Notch signaling. Co-infection of Ad-Notch fusion protein with Ad-VEGF clearly reduced activation of CBF1 promoter activity induced by Ad-VEGF infection alone (FIG. 7). In the case of infection at 40 MOI for each adenovirus in FIG. 7 (panel A), 60% inhibition at 24 hr and 90% inhibition at 48 hr after reporter gene transfection were detected also the inhibitory activity of Notch decoy was dependent on MOI of Ad-Notch fusion protein.

Notch Fusion Proteins Block Initiation of Angiogenic Sprouting Induced by VEGF

Figure 8:
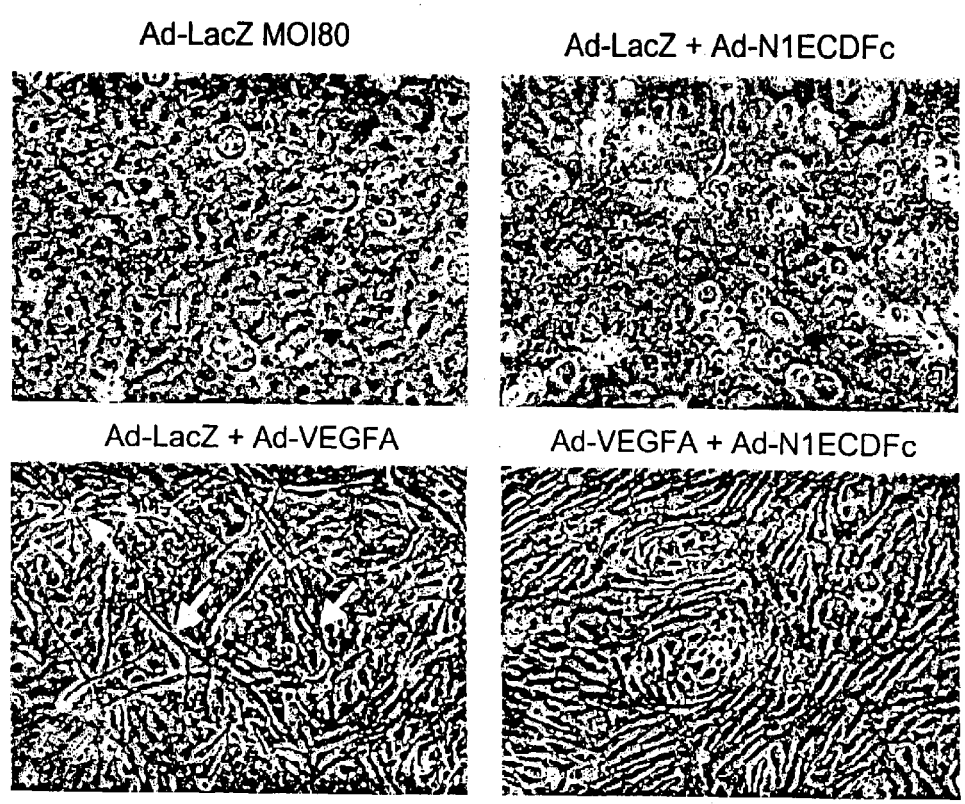

In this experiment, we evaluated the effect of Notch decoy on induction of budding (initiation of sprouting) by overexpressed VEGF-165 in HUVEC. When Ad-VEGF-infected HUVEC were cultured on type collagen gel for 8 days, budding was induced into collagen gel. This induction of budding by overexpressed VEGF was clearly inhibited by coinfection of adenoviral encoding Notch fusion protein (FIG. 8). Ad-Notch fusion protein itself had less effect on morphology.

Figure 9:
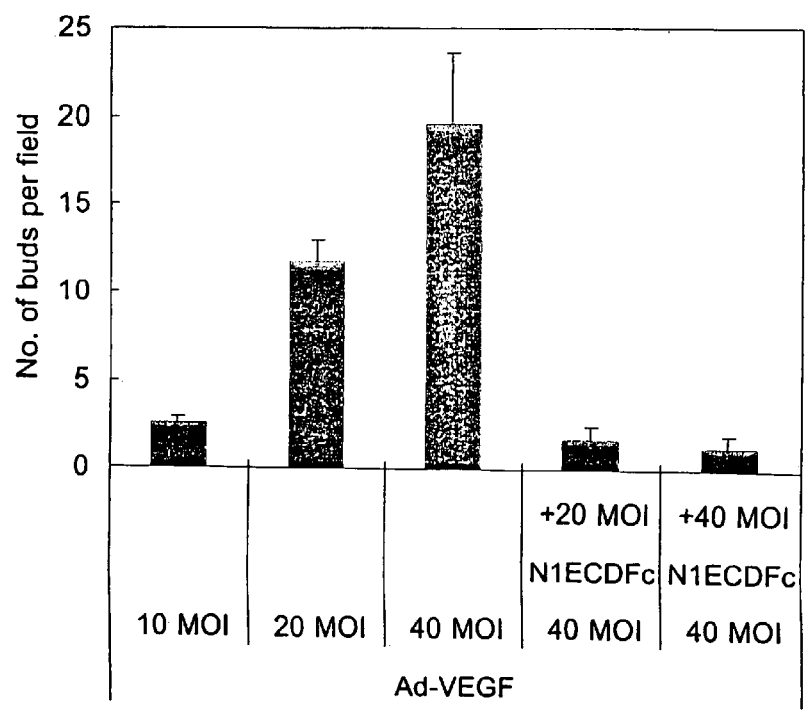

In FIG. 9 we counted buds per field using the microscope. Ad-VEGF-infection into HUVEC increased the number of buds depending on the MOI used. Ad-VEGF-induced budding was clearly inhibited. These data suggest that VEGF induced budding of HUVEC through activation of Notch signaling and that the Notch fusion protein could inhibit VEGF-induced budding.

REFERENCES CITED IN FIRST SERIES OF EXPERIMENTS

1. Artavanis-Tsakonas, S., K. Matsuno, and M. E. Fortini. 1995. Notch signaling. *Science* 268:225-232.
2. Bailey, A. M., and J. W. Posakony. 1995. Suppressor of hairless directly activates transcription of enhancer of split complex genes in response to Notch receptor activity. *Genes & Development* 9:2609-22.
3. Bettenhausen, B., M. Hrabe de Angelis, D. Simon, J. L. Guenet, and A. Gossler. 1995. Transient and restricted expression during mouse embryogenesis of Dll, a murine gene closely related to Drosophila Delta. *Development* 121:2407-18.
4. Blaumueller, C. M., H. Qi, P. Zagouras, and S. Artavanis-Tsakonas. 1997. Intracellular cleavage of Notch leads to a heterodimeric receptor on the plasma membrane. *Cell* 90:281-91.
5. Caronti, B., L. Calandriello, A. Francia, L. Scorretti, M. Manfredi, T. Sansolini, E. M. Pennisi, C. Calderaro, and G. Palladini. 1998. Cerebral autosomal dominant arteriopathy with subcortical infarcts and leucoencephalopathy (CADASIL). Neuropathological and in vitro studies of abnormal elastogenesis. *Acta Neurol Scand.* 98:259-67.
6. Desmond, D. W., J. T. Moroney, T. Lynch, S. Chan, S. S. Chin, D. C. Shungu, A. B. Naini, and J. P. Mohr. 1998. CADASIL in a North American family: clinical, pathologic, and radiologic findings [see comments]. *Neurology* 51:844-9.
7. Dunwoodie, S. L., D. Henrique, S. M. Harrison, and R. S. Beddington. 1997. Mouse Dll3: a novel divergent Delta gene which may complement the function of other Delta homologues during early pattern formation in the mouse embryo. *Development* 124:3065-76.
8. Eastman, D. S., R. Slee, E. Skoufos, L. Bangalore, S. Bray, and C. Delidakis. 1997. Synergy between suppressor of Hairless and Notch in regulation of Enhancer of split m gamma and m delta expression. *Mol Cell Biol.* 17:5620-5634.
9. Fortini, M. E., and S. Artavanis-Tsakonas. 1993. Notch: neurogenesis is only part of the picture. *Cell* 75:1245-7.
10. Gale, N. W., and G. D. Yancopoulos. 1999. Growth factors acting via endothelial cell-specific receptor tyrosine kinases: VEGFs, Angiopoietins, and ephrins in vascular development. *Genes and Development* 13:1055-1066.
11. Gallahan, D., and R. Callahan. 1997. The mouse mammary tumor associated gene INT3 is a unique member of the NOTCH gene family (NOTCH4). *Oncogene* 14:1883-90.
12. Greenwald, I. 1994. Structure/function studies of lin-12/Notch proteins. *Current Opinion in Genetics & Development* 4:556-62.
13. Greenwald, I. 1998. LIN-12/Notch signaling: lessons from worms and flies. *Genes Dev.* 12:1751-62.
14. Henderson, A. M., S. J. Wang, A. C. Taylor, M. Aitkenhead, and C. C. W. Hughes. 2001. The basic helix-loop-helix transcription factor HESR1 regulates endothelial cell tube formation. *J Biol. Chem.* 276:6169-6176.
15. Hicks, C., S. H. Johnston, G. diSibio, A. Collazo, T. F. Vogt, and G. Weinmaster. 2000. Fringe differentially modulates Jagged1 and Delta1 signalling through Notch1 and Notch2. *Nature Cell Biology* 2:515-520.
16. Hsieh, J. J., T. Henkel, P. Salmon, E. Robey, M. G. Peterson, and S. D. Hayward. 1996. Truncated mammalian Notch1 activates CBF1/RBPJk-repressed genes by a mechanism resembling that of Epstein-Barr virus EBNA2. *Molecular & Cellular Biology* 16:952-9.
17. Hsieh, J. J., D. E. Nofziger, G. Weinmaster, and S. D. Hayward. 1997. Epstein-Barr virus immortalization: Notch2 interacts with CBF1 and blocks differentiation. *J. Virol.* 71:1938-45.
18. Jarriault, S., C. Brou, F. Logeat, E. H. Schroeter, R. Kopan, and A. Israel. 1995. Signaling downstream of activated mammalian Notch. *Nature* 377:355-358.
19. Joutel, A., F. Andreux, S. Gaulis, V. Domenga, M. Cecillon, N. Battail, N. Piga, F. Chapon, C. Godfrain, and E. Tournier-Lasserve. 2000. The ectodomain of the Notch3 receptor accumulates within the cerebrovasculature of CADASIL patients [see comments]. *J Clin Invest.* 105:597-605.
20. Joutel, A., C. Corpechot, A. Ducros, K. Vahedi, H. Chabriat, P. Mouton, S. Alamowitch, V. Domenga, M. Cecillion, E. Marechal, J. Maciazek, C. Vayssiere, C. Cruaud, E. A. Cabanis, M. M. Ruchoux, J. Weissenbach, J. F. Bach, M. G. Bousser, and E. Tournier-Lasserve. 1996. Notch3 mutations in CADASIL, a hereditary adult-onset condition causing stroke and dementia. *Nature* 383:707-10.
21. Kopan, R., E. H. Schroeter, H. Weintraub, and J. S. Nye. 1996. Signal transduction by activated mNotch: importance of proteolytic processing and its regulation by the extracellular domain. *Proc Natl Acad Sci USA* 93:1683-8.
22. Krebs, L. T., Y. Xue, C. R. Norton, J. R. Shutter, M. Maguire, J. P. Sundberg, D. Gallahan, V. Closson, J. Kitajewski, R. Callahan, G. H. Smith, K. L. Stark, and T. Gridley. 2000. Notch signaling is essential for vascular morphogenesis in mice. *Genes and Development* 14:1343-1352.
23. Lardelli, M., J. Dahlstrand, and U. Lendahl. 1994. The novel Notch homologue mouse Notch3 lacks specific epidermal growth factor-repeats and is expressed in proliferating neuroepithelium. *Mechanism of Development* 46:123-136.
24. Lawson, N. D., N. Scheer, V. N. Pham, C. Kim, A. B. Chitnis, J. A. Campos-Ortega, and B. M. Weinstein. 2001. Notch signaling is required for arterial-venous differentiation during embryonic vascular development. *Development* 128:3675-3683.
25. Lewis, J. 1998. Notch signaling and the control of cell fate choices in vertebrates. *Semin Cell Dev Biol.* 9:583-589.
26. Lieber, T., S. Kidd, E. Alcomo, V. Corbin, and M. W. Young. 1993. Antineurogenic phenotypes induced by truncated Notch proteins indicate a role in signal transduction and may point to a novel function for Notch in nuclei. *Genes Dev.* 7:1949-1965.
27. Lindner, V., C. Booth, I. Prudovsky, D. Small, T. Maciag, and L. Liaw. 2001. Members of the Jagged/Notch gene familites are expressed in injured arteries and regulate cell phenotype via alteration in cell matrix and cell-cell interations. *Pathology* 159:875-883.
28. Lindsell, C. E., C. J. Shawber, J. Boulter, and G. Weinmaster. 1995. Jagged: A mammalian ligand that activates Notch1. *Cell* 80:909-917.
29. Logeat, F., C. Bessia, C. Brou, O. LeBail, S. Jarriault, N. G. Seidah, and A. Israel. 1998. The Notch1 receptor is cleaved constitutively by a furin-like convertase. *Proc Natl Acad Sci USA* 95:8108-12.
30. Lyman, D., and M. W. Young. 1993. Further evidence for function of the *Drosophila* Notch protein as a transmembrane receptor. *Proc Natl Acad Sci USA* 90:10395-10399.
31. Matsuno, K., M. J. Go, X. Sun, D. S. Eastman, and S. Artavanis-Tsakonas. 1997. Suppressor of Hairless-independent events in Notch signaling imply novel pathway elements. *Development* 124:4265-4273.
32. Nakagawa, O., D. G. McFadden, M. Nakagawa, H. Yanagisawa, T. Hu, D. Srivastava, and E. N. Olson. 2000. Members of the HRT family of basic helix-loop-helix proteins act as transcriptional repressors downstream of Notch signaling. *Proc Natl Acad Sci USA* 97:13655-13660.
33. Oberg, C., J. Li, A. Pauley, E. Wolf, M. Gurney, and U. Lendahl. 2001. The Notch intracellular domain is ubiquitinated and negatively regulated by the mammalian Sel-10 homolog. *J Biol. Chem.* 276:35847-35853.
34. Owens, G. K. 1995. Regulation of differentiation of vascular smooth muscle cells. *Physiol Rev.* 75:487-527.
35. Rebay, I., R. G. Fehon, and S. Artavanis-Tsakonas. 1993. Specific truncations of *Drosophila* Notch define dominant activated and dominant negative forms of the receptor. *Cell* 74:319-29.
36. Robey, E. 1997. Notch in vertebrates. *Curr Opin Genet Dev.* 7:551-7.
37. Roehl, H., M. Bosenberg, R. Blelloch, and J. Kimble. 1996. Roles of the RAM and ANK domains in signaling by the *C. elegans* GLP-1 receptor. *Embo J.* 15:7002-7012.
38. Rogers, S., R. Wells, and M. Rechsteiner. 1986. Amino acid sequences common to rapidly degrade proteins: The PEST hypothesis. *Science* 234:364-368.
39. Sasai, Y., R. Kageyama, Y. Tagawa, R. Shigemoto, and S. Nakanishi. 1992. Two mammalian helix-loop-helix factors structurally related to *Drosophila* hairy and Enhancer of split. *Genes & Dev.* 6:2620-2634.
40. Shawber, C., J. Boulter, C. E. Lindsell, and G. Weinmaster. 1996a. Jagged2: a serrate-like gene expressed during rat embryogenesis. *Dev Biol.* 180:370-6.
41. Shawber, C., D. Nofziger, J. J. Hsieh, C. Lindsell, O. Bogler, D. Hayward, and G. Weinmaster. 1996b. Notch signaling inhibits muscle cell differentiation through a CBF1-independent pathway. Development 122:3765-73.
42. Shimizu, K., S. Chiba, T. Saito, T. Takahashi, K. Kumano, H. Hamada, and H. Hirai. 2002. Integrity of intracellular domain of Notch ligand is indespensable for cleavage required for the release of the Notch2 intracellular domain. *Embo J.* 21:294-302.
43. Shutter, J. R., S. Scully, W. Fan, W. G. Richards, J. Kitajewski, G. A. Deblandre, C. R. Kintner, and K. L. Stark. 2000a. Dll4, a novel Notch ligand expressed in arterial endothelium. *Genes Dev.* 14:1313-1318.
44. Shutter, J. R., S. Scully, W. Fan, W. G. Richards, J. Kitajewski, G. A. Deblandre, C. R. Kitner, and K. L. Stark. 2000b. Dll4, a novel Notch ligand expressed in arterial endothelium. Genes and Development 14:1313-1318.
45. Struhl, G., K. Fitzgerald, and I. Greenwald. 1993. Intrinsic activity of the Lin-12 and Notch intracellular domains in vivo. *Cell* 74:331-45.
46. Swiatek, P. J., C. E. Lindsell, F. Franco del Amo, G. Weinmaster, and T. Gridley. 1994. Notch 1 is essential for postimplantation development in mice. *Genes & Development* 8:707-719.
47. Tamura, K., Y. Taniguchi, S. Minoguchi, T. Sakai, T. Tun, T. Furukawa, and T. Honjo. 1995. Physical interaction between a novel domain of the receptor Notch and the transcription factor RBP-J kappa/Su(H). *Curr Biol.* 5:1416-1423.
48. Tietze, K., N. Oellers, and E. Knust. 1992. Enhancer of splitD, a dominant mutation of *Drosophila*, and its use in the study of functional domains of a helix-loop-helix protein. *Proc Natl Acad Sci USA* 89:6152-6156.
49. Uyttendaele, H., J. Ho, J. Rossant, and J. Kitajewski. 2001. Vascular patterning defects associated with expression of activated Notch4 in embryonic endothelium. *PNAS.* 98:5643-5648.
50. Uyttendaele, H., G. Marazzi, G. Wu, Q. Yan, D. Sassoon, and J. Kitajewski. 1996. Notch4/int-3, a mammary proto-oncogene, is an endothelial cell-specific mammalian Notch gene. *Development* 122:2251-9.
51. Vervoort, M., C. Dambly-Chaudiere, and A. Ghysen. 1997. Cell fate determination in *Drosophila. Curr Opin Neurobiol.* 7:21-28.
52. Villa, N., L. Walker, C. E. Lindsell, J. Gasson, M. L. Iruela-Arispe, and G. Weinmaster. 2001. Vascular expression of Notch pathway receptors and ligands is restricted to arterial vessels. *Mechanisms of Development* 108:161-164.
53. Weinmaster, G. 1997. The Ins and Outs of Notch Signaling. *Mol Cel Neurosci.* 9:91-102.
54. Weinmaster, G. 1998. Notch signaling: direct or what? *Curr Opin Genet Dev.* 8:436-42.
55. Weinmaster, G., V. J. Roberts, and G. Lemke. 1992. Notch 2: a second mammalian Notch gene. *Development* 116: 931-941.
56. Weinmaster, G., V. J. Roberts, and G. A. Lemke. 1991. A homolog of *Drosophila* Notch expressed during mammalian development. *Development* 113:199-205.
57. Wettstein, D. A., D. L. Turner, and C. Kintner. 1997. The *Xenopus* homolog of *Drosophila* Suppressor of Hairless mediates Notch signaling during primary neurogenesis. *Development* 124:693-702.
58. Wu, G., E. J. Hubbard, J. K. Kitajewski, and I. Greenwald. 1998. Evidence for functional and physical association between *Caenorhabditis elegans* SEL-10, a Cdc4p-related protein, and SEL-12 presenilin. *Proc Natl Acad Sci USA* 95:15787-91.
59. Wu, G., S. A. Lyapina, I. Das, J. Li, M. Gurney, A. Pauley, I. Chui, R. J. Deshaies, and J. Kitajewski. 2001. SEL-10 is an inhibitor of notch signaling that targets notch for ubiquitin-mediated protein degradation. *Mol Cell Biol.* 21:7403-7015.
60. Xue, Y., X. Gao, C. E. Lindsell, C. R. Norton, B. Chang, C. Hicks, M. Gendron-Maguire, E. B. Rand, G. Weinmaster, and T. Gridley. 1999. Embryonic lethality and vascular defects in mice lacking the Notch ligand Jagged1. *Hum Mol Genet.* 8:723-30.

Second Series of Experiments

VEGF Initiates Angiogenesis via an Activation of Notch Signaling

Both the VEGF and Notch signaling pathways are critical for vascular development. Here we show that VEGF activates Notch signaling to initiate angiogenesis. VEGF increased the expression of Delta4 and Notch4 causing Notch signal activation and inducing filopodia in cultured primary endothelial cells. Studies using VEGF Receptor inhibitors show that Notch signal activation in turn enhances VEGF action by inducing VEGFR-1 (Flt-1) expression. Other elements of VEGF action, including the induction of MMP-9 and MT1-MMP, are mediated by Notch. Using in vivo assays to model VEGF-induced skin neovascularization, we found that a secreted Notch inhibitor (Notch-based fusion protein) blocks VEGF-induced neo-vascularization and induction of VEGFR-1 expression. Thus, Notch signaling is requisite for angiogenesis regulated by VEGF, likely at the level of initiation.

VEGF is a key regulator of angiogenesis progression consisting of multiple processes, such as degradation of ECM, budding (filopodia formation), proliferation, survival, and migration of endothelial cells. Although most of the steps might be co-operated with downstream molecules of VEGF signaling, it is not known how these steps are coordinately regulated to result in more complex morphogenetic events, such as angiogenic sprouting. Notch signaling is an evolutionarily conserved signaling mechanism that functions to regulate cell fate decisions (1). Upon binding by a ligand, such as Jagged and Delta-like, the cytoplasmic domain of Notch (NotchIC) is released by presenilin/γ-secretase, translocates to the nucleus, interacts with the transcriptional repressor CSL (CBF1/Su(H)/lag2), and converts it to a transcriptional activator (1). Roles of Notch signaling in vascular development were suggested by studies of mice with targeted mutation (2). Since Notch activation within the endothelium also disrupts vascular remodeling, proper Notch signaling is essential for vascular development (3). Although relevance of Notch to VEGF signaling is suggested (4-6), it is still unclear how Notch signaling has a role in VEGF-regulated angiogenesis and whether Notch signaling participates in physiological and pathological angiogenesis in the adult vasculature.

HUVEC (Human Umbilical Vein Endothelial cells) growth are dependent on VEGF (FIGS. 26A and 26B) and differentiation-related biological responses, such as sprouting, and can be evaluated at an early stage (7). At first, we examined whether adenovirally transduced VEGF induced both Notch and Notch ligand expression in HUVEC cultured with complete medium containing bFGF (FIG. 22A), as reported (5). RT-PCR analysis showed that both Dl4 and Notch4 mRNA was up-regulated in adenovirally-transduced VEGF HUVEC (Ad-VEGF-HUVEC), compared to adenovirally-transduced LacZ HUVEC (Ad-LacZ-HUVEC) (FIG. 22A). Transduced VEGF did not appear to induce Jagged1 and Notch1 expression. Transduced-VEGF also activated Notch signaling in a dose-dependent manner by measuring CSL-luciferase reporter activity (FIG. 22B), which was transactivated with Notch signaling (8). Notch signaling was activated at a higher dosage of Ad-VEGF, compared to proliferation (FIG. 26A). Since SU5416, which is an inhibitor of VEGFR kinases, decreased VEGF-induced CSL-luciferase reporter activity (FIG. 22C), VEGF induced Notch signaling through activation of receptor kinase. Since Notch mutants lacking both transmembrane and cytoplasmic domains functioned as dominant negative inhibitors against Notch signaling (9), we made a Notch-based fusion protein or decoy (N1ECDFc) to inhibit Notch signaling (FIG. 22D). Western blotting analysis of conditioned medium of Ad-N1ECDFc-transduced HUVEC (Ad-N1ECDFc-HUVEC) demonstrated that N1ECDFc was expressed and secreted well (FIG. 22E). By using a co-culture assay, in which Bosc cells expressing Notch ligands (either J1, Dl1 or Dl4) activated Notch signaling in HeLa cells expressing Notch1 compared to control Bosc cells, we determined inhibition of Notch signaling with transfection of a N1ECDFc-expression plasmid (FIG. 22F). Then, we examined whether N1ECDFc inhibited activation of Notch signaling by transduced VEGF in HUVEC (FIG. 22G). Co-transduction of Ad-N1ECDFc with Ad-VEGF into HUVEC clearly decreased CSL luciferase activity induced by VEGF. Gerhardt et al. reported that VEGF controlled angiogenesis in the early postnatal retina by guiding filopodia extension at the tips of the vascular sprouts (10). During angiogenic sprouting, the formation of a specialized endothelial cell making filopodia projections among quiescent endothelial cells, might be one of the early events. Here we mean formation of a single endothelial cell making filopodia protrusions as budding. Budding of the primary endothelial cells is induced by cultivating them 3-dimensionally on either fibrin or collagen gel (11). In the case where Ad-VEGF-HUVEC were cultured on collagen gel with complete medium, transduced-HUVEC made filopodia extensions into the collagen gel for 5 days (FIG. 22H) and the number of buds was increased in a dose-dependent manner (FIG. 27A). Activation of Notch signaling by adenovirus encoding the activated form of Notch4 (Ad-Notch4/int3) induced HUVEC budding (12) and that of Notch1 (Ad-N1IC) also induced HUVEC budding (FIGS. 23A & 27B). Since both VEGF and Notch signaling induce HUVEC budding, we examined whether N1ECDFc inhibited VEGF-induced HUVEC budding (FIG. 22H-I). Budding of Ad-VEGF-HUVEC was clearly inhibited by co-transduction of Ad-N1ECDFc. Neither Ad-LacZ or Ad-N1ECDFc-transduced HUVEC formed buds (FIG. 22H). N1ECDFc inhibited VEGF-induced HUVEC budding without affecting cell number (FIG. 22I). Transduced-N1ECDFc did not clearly alter proliferation of HUVEC, while that of Ad-N1IC-transduced HUVEC was inhibited in a dose-dependent manner (FIG. 28A), consistent with the inhibitory efficacy of Notch signaling against endothelial proliferation (13).

To test whether Notch signaling is down-stream of VEGF, we evaluated three distinct inhibitors for receptor tyrosine kinases, including VEGFR on N1IC-induced HUVEC budding, because three growth factors existed in complete medium (FIG. 23A-C). At a concentration of 1 μM, each compound showed selective inhibition against each kinase (data not shown). Neither PD166866 or ZD1893 affected budding of Ad-N1IC-HUVEC, while SU5416 clearly inhibited it (FIG. 23A-B). SU5416 selectively inhibited budding of Ad-N1IC-HUVEC with less reduction of viability at lower concentrations (FIG. 23C). Since Taylor et al. reported that Notch down-regulated Flk1/KDR/VEGFR2 expression (14), it was unlikely that Notch co-operated with Flk1 to promote budding. Thus, we examined whether activation of Notch signaling affected Flt1/VEGFR1 expression in HUVEC, because SU5416 inhibits both Flt1 and Flk1 kinase activity (15). RT-PCR analysis demonstrated that expression of Flt1 mRNA was up-regulated in Ad-N1IC-HUVEC, while expression of endothelial cell maker, CD31 mRNA, was not compared to that in Ad-LacZ-HUVEC (FIG. 23D). Western blotting analysis also showed that expression of Flt1 protein was up-regulated in Ad-N1IC-HUVEC (FIG. 23E). Thus, we examined whether PlGF, which is a selective ligand for Flt1, promoted budding of HUVEC in which Flt1 was up-regulated via activation of Notch signaling (FIG. 23F-G). PlGF increased the number of Ad-N1IC-HUVEC buds by 150%, compared to the absence of PlGF (FIG. 23F). Moreover, PlGF increased HUVEC buds containing multiple filopodia by 250% (FIG. 23G). While reduction of Flt1 expression using small interfering RNA (siRNA) for Flt1 inhibited budding of Ad-N1IC-HUVEC (FIG. 23J), transfection of which selectively decreased expression of Flt1 mRNA (FIG. 23H) and that of Flt1 protein (FIG. 23I). Although reduction of Flk1 expression with Flk1 siRNA also inhibited budding of Ad-N1IC-HUVEC (FIG. 30B), the inhibitory efficacy of Flk1 siRNA was less than that of Flt1 siRNA (FIG. 23J). Effects of Flk1 siRNA were more effective on budding of Ad-VEGF-HUVEC than that of Ad-N1IC-HUVEC (FIG. 30B-C). Transfection with Flt1 siRNA inhibited budding of both Ad-N1IC- and Ad-VEGF-HUVEC to a similar extent (data not shown).

Several studies demonstrated that VEGF regulated gelatinase activities in endothelial cells and the significance of gelatinase activity like MMP-2 and MMP-9 has been firmly established to induce angiogenic sprouting (16). We examined whether VEGF regulated gelatinase acitivity via Notch signaling in HUVEC.

In Gelatin zymography, conditioned medium of Ad-VEGF-HUVEC showed both induction and activation of MMP9, which started to be detected at day 6 (FIG. 24A) and activation of MMP2, which was detected at day 4 (FIG. 24B), compared to those of Ad-LacZ-HUVEC. Co-transduction of Ad-N1ECDFc with Ad-VEGF showed inhibition of both induction and activation of MMP9 (FIG. 24A) and an activation of MMP2 (FIG. 24B). RT-PCR analysis demonstrated that expression of MMP9 mRNA was up-regulated in Ad-N1IC-HUVEC, but expression of MMP2 mRNA was decreased in Ad-N1IC-HUVEC (FIG. 24C). Since induction of MMP2 activity was not detected in gelatin zymography (FIG. 24B), this result was a likely consequence. While expression of MT1-MMP, which is able to activate MMP2 at the cell surface (17), was up-regulated at both the transcript and protein levels in Ad-N1IC-HUVEC (FIG. 24D). As VEGF can regulate both gelatinase and MT1-MMP expression (16), RT-PCR analysis demonstrated that both MMP9 and MT1-MMP were up-regulated in Ad-VEGF-HUVEC, compared to Ad-LacZ-HUVEC and this induction was inhibited with co-transduction of Ad-N1ECDFc (FIG. 24E). Ad-N1ECDFc infection alone did not affect expression of either MMP9 or MT1-MMP in Ad-LacZ infected HUVEC (data not shown). Requisition of MMPs for angiogenic sprouting has been established by synthetic MMP inhibitors (16). GM6001 is one broad inhibitor against MMPs including MMP2, MMP9 and MT1-MMP (18). GM6001 clearly decreased budding of Ad-N1IC-HUVEC on both collagen (FIG. 31A-B) and fibrin gel (data not shown).

In the mouse Dorsa Air Sac (DAS) assay (19), stable transfectant of 293 cells over-expressing VEGF121 (293/VEGF) significantly induced in vivo angiogenesis (FIG. 25A, left panel). This VEGF-induced angiogenesis was clearly inhibited by coexpression of N1ECDFc, compared to 293/VEGF alone (FIG. 25A). Vessel density was measured and an index of angiogenesis given in FIG. 25B, demonstrating the 293/VEGF induced angiogenesis is inhibited by co-expression of 293/N1ECDFc (FIG. 25B).

Also, in the mouse Dorsa Air Sac (DAS) assay (19), the human breast cancer cell line, MDA-MB-231 significantly induced in vivo angiogenesis, presumably via the secretion of VEGF (FIG. 25C, left panel). This VEGF-induced angiogenesis was clearly inhibited by adenovirus mediated expression of N1ECDFc, compared to adenovirus expressing LacZ. (FIG. 25C). Vessel density was measured and an index of angiogenesis given in FIG. 25D, demonstrating the MDA-MB-231 induced angiogenesis is inhibited by expression of N1ECDFc.

Flk1 is a major positive signal transducer for angiogenesis through its strong tyrosine kinase activity in the embryo, while Flt1 is thought to be a negative signal transducer for angiogenesis. However, a positive role for Flt-1 was demonstrated in adult mice, as in vivo growth of LLC over-expressing PlGF2 was severely compromised in mice lacking the cytoplasmic Flt-1 kinase domain (20). Notch might function to alter VEGF signaling by inducing Flt-1 signaling and moderate Flk-1 signaling either to induce filopodia extension or potentiate angiogenic sprouting, since PlGF/Flt-1 signaling altered the phospholyration site of Flk-1 and potentiated ischemic myocardial angiogenesis (21). Interestingly, Notch signaling also up-regulated PlGF expression (FIG. 29). However, continuous activation of Notch signaling inhibits formation of multi-cellular lumen-containing angiogenic sprouts, as previously reported (22). Notch signaling should be turned off after budding/filopodia formation and transient activation of the Notch pathway might be required. In a transgenic mouse model of pancreatic beta-cell carcinogenesis (Rip1Tag2 mice) in which tumor angiogenesis is VEGF dependent, the level of VEGF expression is not increased, but mobilization of extracellular VEGF stored in the matrix to VEGF receptors occurs. MMP-9 is responsible for this mobilization and tumor progression was inhibited in Rip1Tag23MMP-9-null double-transgenic mice (23). Notch up-regulated MMP-9 expression and might increase local VEGF level at the site for angiogenic sprouting. While Notch also up-regulates MT1-MMP expression, extracellular MMP-2 might be targeted to the cell membrane of Notch-activated endothelial cells. Notch might determine the site for angiogenic sprouting by regulating gelatinase activity and VEGF concentration. Since endothelial MMP-9 was regulated by Flt-1 in lung specific metastasis (20), Flt-1 might participate in induction of MMP-9 indirectly.

REFERENCES CITED IN SECOND SERIES OF EXPERIMENTS

1. Artavanis-Tsakonas S, Rand M D, Lake R J. Notch Signaling: Cell Fate Control and Signal Integration in Development. Science 1999; 284(5415):770-776.
2. Shawber C J, J. K. Notch function in the vasculature: insights from zebrafish, mouse and man. Bioessays. 2004; 26(3):225-34.
3. Uyttendaele H, Ho J, Rossant J, J. K. Vascular patterning defects associated with expression of activated Notch4 in embryonic endothelium. Proc Natl Acad Sci USA. 2001; 98(10):5643-8.
4. Lawson N D, Vogel A M, B M. W. sonic hedgehog and vascular endothelial growth factor act upstream of the Notch pathway during arterial endothelial differentiation. Dev Cell 2002; 3(1):127-36.
5. Liu Z J, Shirakawa T, Li Y, Soma A, Oka M, Dotto G P, et al. Regulation of Notch1 and Dll4 by vascular endothelial growth factor in arterial endothelial cells: implications for modulating arteriogenesis and angiogenesis. Mol Cell Biol. 2003; 23(1):14-25.

6. Gale N W, Dominguez M G, Noguera I, Pan L, Hughes V, Valenzuela D M, et al. Haploinsufficiency of delta-like 4 ligand results in embryonic lethality due to major defects in arterial and vascular development. Proc Natl Acad Sci USA. 2004; 101(45):5949-54.
7. Montesano R, L. O. Phorbol esters induce angiogenesis in vitro from large-vessel endothelial cells. J Cell Physiol. 1987; 130(2):284-91.
8. Jarriault S, Brou C, Logeat F, Schroeter E H, Kopan R, A. I. Signalling downstream of activated mammalian Notch. Nature. 1995; 377(6547):355-8.
9. Small D, Kovalenko D, Kacer D, Liaw L, Landriscina M, Di Serio C, et al. Soluble Jagged 1 represses the function of its transmembrane form to induce the formation of the Src-dependent chord-like phenotype. J Biol Chem 2001; 276(34):32022-30.
10. Gerhardt H, Golding M, Fruttiger M, Ruhrberg C, Lundkvist A, Abramsson A, et al. VEGF guides angiogenic sprouting utilizing endothelial tip cell filopodia. J Cell Biol 2003; 161(6):1163-77.
11. Koolwijk P, van Erck M G, de Vree W J, Vermeer M A, Weich H A, Hanemaaijer R, et al. Cooperative effect of TNFalpha, bFGF, and VEGF on the formation of tubular structures of human microvascular endothelial cells in a fibrin matrix. Role of urokinase activity. J Cell Biol 1996; 132(6):1177-88.
12. Das I, Craig C, Funahashi Y, Jung K M, Kim T W, Byers R, et al. Notch oncoproteins depend on gamma-secretase/presenilin activity for processing and function. J Biol Chem 2004; 279(29):30771-80.
13. Noseda M, Chang L, McLean G, Grim J E, Clurman B E, Smith L L, et al. Notch activation induces endothelial cell cycle arrest and participates in contact inhibition: role of p21Cip1 repression. Mol Cell Biol 2004; 24(20):8813-22.
14. Taylor K L, Henderson A M, C C. H. Notch activation during endothelial cell network formation in vitro targets the basic HLH transcription factor HESR-1 and downregulates VEGFR-2/KDR expression. Microvasc Res 2002; 64(3):372-83.
15. Itokawa T, Nokihara H, Nishioka Y, Sone S, Iwamoto Y, Yamada Y, et al. Antiangiogenic effect by SU5416 is partly attributable to inhibition of Flt-1 receptor signaling. Mol Cancer Ther 2002; 1(5):295-302.
16. Pepper M S. Role of the matrix metalloproteinase and plasminogen activator-plasmin systems in angiogenesis. Arterioscler Thromb Vasc Biol 2001; 21(7):1104-17.
17. Seiki M, Koshikawa N, I. Y. Role of pericellular proteolysis by membrane-type 1 matrix metalloproteinase in cancer invasion and angiogenesis. Cancer Metastasis Rev 2003; 22(2-3):129-43.
18. Yamamoto M, Tsujishita H, Hori N, Ohishi Y, Inoue S, Ikeda S, et al. Inhibition of membrane-type 1 matrix metalloproteinase by hydroxamate inhibitors: an examination of the subsite pocket. J Med Chem 1998; 41(8):1209-17.
19. Funahashi Y, Wakabayashi T, Semba T, Sonoda J, Kitoh K, K. Y. Establishment of a quantitative mouse dorsal air sac model and its application to evaluate a new angiogenesis inhibitor. Oncol Res. 1999; 11(7):319-29.
20. Hiratsuka S, Nakamura K, Iwai S, Murakami M, Itoh T, Kijima H, et al. MMP9 induction by vascular endothelial growth factor receptor-1 is involved in lung-specific metastasis. Cancer Cell 2002; 2(4):289-300.
21. Autiero M, Waltenberger J, Communi D, Kranz A, Moons L, Lambrechts D, et al. Role of PlGF in the intra- and intermolecular cross talk between the VEGF receptors Flt1 and Flk1. Nat Med 2003; 9(7):936-43.
22. Leong K G, Hu X L L, Noseda M, Larrivee B, Hull C, Hood L, et al. Activated Notch4 inhibits angiogenesis: role of beta 1-integrin activation. Mol Cell Biol 2002; 22(8):2830-41.
23. Bergers G, Brekken R, McMahon G, Vu T H, Itoh T, Tamaki K, et al. Matrix metalloproteinase-9 triggers the angiogenic switch during carcinogenesis. Nat Cell Biol 2000; 2(10):737-44.

What is claimed is:

1. A fusion protein comprising an extracellular domain of a human Notch4 receptor protein including Notch EGF repeats linked at its carboxyl terminus to the amino terminus of an Fc portion of an antibody, wherein the extracellular domain of the Notch receptor protein comprises the EGF-repeats of the Notch4 receptor protein and is bound to the Fc portion of the antibody by means of a peptide linker, wherein the peptide linker comprises the consecutive amino acids DLGPG (SEQ ID NO:2).

2. The fusion protein of claim 1, wherein the extracellular domain of the Notch4 receptor protein is encoded by the consecutive nucleotides set forth in SEQ ID NO: 14.

3. A fusion protein comprising an extracellular domain of a human Notch receptor protein and an Fc portion of an antibody, wherein the extracellular domain of the Notch receptor protein comprises the EGF repeats of such Notch receptor protein and the extracellular domain is linked at its carboxyl terminus to the amino terminus of the Fc portion of an antibody by means of a peptide linker, wherein the Notch receptor protein is a human Notch1, Notch2, Notch3, or Notch4 receptor protein, the amino acid sequence of which is encoded by the nucleic acid sequence set forth in SEQ ID NOs. 11, 12, 13 and 14, respectively, and wherein the extracellular domain is bound to the Fc portion of the antibody by means of a peptide linker which comprises the consecutive amino acids DLGPG (SEQ ID NO:2).

4. The fusion protein of claim 3, wherein the human Notch receptor protein is human Notch1 receptor protein, the amino acid sequence of which is encoded by the nucleic acid sequence set forth in SEQ ID NO:11.

5. The fusion protein of claim 3, wherein the human Notch receptor protein is human Notch2 receptor protein, the amino acid sequence of which is encoded by the nucleic acid sequence set forth in SEQ ID NO:12.

6. The fusion protein of claim 3, wherein the human Notch receptor protein is human Notch3 receptor protein, the amino acid sequence of which is encoded by the nucleic acid sequence set forth in SEQ ID NO:13.

* * * * *